United States Patent
Türeci et al.

(12)

(10) Patent No.: US 8,637,006 B2
(45) Date of Patent: Jan. 28, 2014

(54) RECOMBINANT VACCINES AND USE THEREOF

(75) Inventors: Özlem Türeci, Mainz (DE); Ugur Sahin, Mainz (DE); Sebastian Kreiter, Mainz (DE)

(73) Assignee: BioNTech AG, Mainz (DE)

( * ) Notice: Subject to any disclaimer, the term of this patent is extended or adjusted under 35 U.S.C. 154(b) by 0 days.

(21) Appl. No.: 13/471,606

(22) Filed: May 15, 2012

(65) Prior Publication Data
US 2013/0011426 A1 Jan. 10, 2013

Related U.S. Application Data

(62) Division of application No. 10/575,640, filed as application No. PCT/EP2004/011512 on Oct. 13, 2004, now Pat. No. 8,178,653.

(30) Foreign Application Priority Data

Oct. 14, 2003 (DE) .................................. 103 47 710

(51) Int. Cl.
*A01N 63/00* (2006.01)
*C12N 1/20* (2006.01)
*A61K 48/00* (2006.01)
*C07H 21/04* (2006.01)
*A61K 39/00* (2006.01)

(52) U.S. Cl.
USPC ..................... 424/93.7; 435/252.3; 514/44 R; 536/23.4

(58) Field of Classification Search
None
See application file for complete search history.

*Primary Examiner* — Gerald R Ewoldt
*Assistant Examiner* — Marianne Dibrino
(74) *Attorney, Agent, or Firm* — Olson & Cepuritis, Ltd.

(57) ABSTRACT

The present invention relates to fusion molecules of antigens, the nucleic acids coding therefor and the use of such fusion molecules and nucleic acids. In particular, said invention relates to fusion molecules, comprising an antigen and the trans-membrane region and cytoplasmic region of a MHC molecule and/or the cytoplasmic region of a MHC or a SNARE molecule.

10 Claims, 17 Drawing Sheets

Fig. 2
cassettes containing cloning sites (MCS) for expression of MHC fusion proteins of the invention
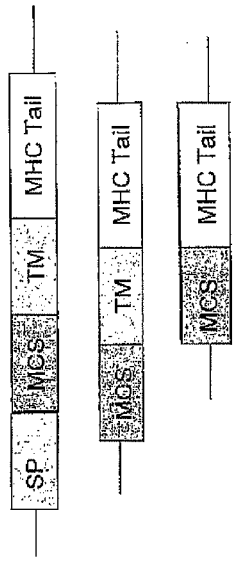
cassettes containing antigens cloned therein for expression of MHC fusion proteins of the invention
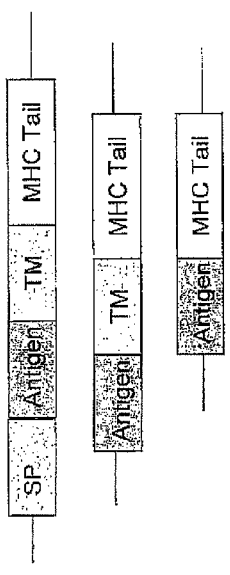

Fig. 7 cassettes containing cloning sites (CS) for expression of SNARE fusion proteins of the invention cassettes containing antigens cloned therein for expression of SNARE fusion proteins of the invention

Fig. 8A

| SEQ ID NO | | |
|---|---|---|
| 1 | signal peptide (SecSignal) | ATGCGGGTCACGGCGCCCGAACCCTCATCCTGCTGCTCCTCAGTCTCGGGGAGCCCTGGCCCTGACCG AGACCTGGGCCGGCTCC |
| 2 | signal peptide SecSignal | MRVTAPRTLILILSGALALTETWAGS |
| 3 | HLA class I TM-CM | ATCGTGGGCATTGTTGCTGGCCTGTCCTGGCTGTCCTAGCAGTTGTGGTCGCTACTGTGATGTGTAGGAGGAAGAG CTCAGGTGGAAAAGGAGGAGGGAGCTACTCTCAGGCTCGTCCAGGGACAGTGCCCAGGCTCTGATGTGTCTCACAGCTTGA |
| 4 | HLA class I TM-CM | IVGIVAGLAVLAVVVIGAVVATVMCRRKSSGKGGSYSQAASSDSAQGSDVSLTA |
| 5 | HLA class II TM-CM | CAGAGCAAGATGCTGAGTGAGTCGGGGGCTTTGTGCTGGGCCTGCTCTTCCTTGGGGCTGTTCATCTACTTCAGGAATCA GAAAGGACACTCTGGACTTCAGCCAAGAGATTCCTGAGCTGA |
| 6 | HLA class II TM-CM | QSKMLSGVGGFVLGLLFLGAGLFIYFRNQKGHSGLQPRGF LS |
| 7 | | CTGCAGGTCGACTCTAGAGGATCC |
| 8 | | LQVDSRGS |
| 9 | pp65 antigen | atggagtcgcgcggttcgcgttgcccgagaatgatatccgtactggtcccattcgggcacgtgctgaaagccgtgtttagtcg cggcgatacgccggtgctgcgcacgcgactcctgcagacgcgactcgtgagccagccaggtatccagtcagctgctgatcttgg tatcgcagtacacgcgcgactcgagtgccaatcagcgacgtcaggtgcagcacgtacttacggcagcag gtgagaacgtgtcggtcaacgtgaacatctgcccagcatctgccccagagcatctcgccgcgccaaccgaggagcatctcagagagcccaaccgccgactacctgctgc gctgcgctcaagatgctgaactcacgcgtgcaagcagatgtgtggcaagcgtctcggagtcgacgtgcctgacgcctgacgtcagcag aaccagtgcgaagagccgactgctatacacgctgccgtgttttccaccaaggacgtgcactgtgagtgaccagtcaaggtgataggtgacgtgtgacctgcagt gcacgagctgttgctcatgcgccctccgcccgcaacggccaagcctctttatgcacgtcacgctttggttgtgtccaaaaatatgataatcaaaacgggcaagat aacccgcaacctcatgccctccgcgcccaccagctgctgctgcccgccctgagctgctgcgccacgagctgtgaactgtcagtacgagaccgagacgcagcattc cagtaacctgctcgtctctttcatgctgataggaacgggcagacagcagatatcgactgcacacatcgactccgcagccgacctgctgcggcgggcctcctgacggcgcg cagtagtaacctgctgctctttcatgctgatgaacgggcagcagatatcgactcttcctgaggtacaaccatacgcagccgacgagacgcagaactgtggaactgcgcacctaccacgcacctcaccagcatc gtggtcgcgctcttctttcttttgatgaacgggcagcagatatcgactcttcctgctctgtctgggacgccgacgagcgcgtcagtacagcagctgtgctgcgtctagactcagccactgcgccgcgtgcgcgtgacgtgcgctcgctgctggcctcaacggcttgtatcgtccaactgtggtcgacc tcgcatccagggactcgacgtgagtcgtaaccaatcagcaatcagcatcagctgcgggcggcctgagcacgacgccgtccagaccgccgacctgctgcgctctgggcggctccatcgacttcaccagccca gcggatcggactgccgacatcctggctcgacgtgagtcgtaaccaatcagcaatcagcatcagctgcgggcggcctgagcacgacgccgtccagaccgccgacctgctgcgctctgggcggctccatcgacttcaccagcagta acttccgcgccgcaaacgcgacgcgtcgggcgtttatgacgcgggcacgtccgggctgacacgccgggccttaaggccga |

Fig. 8B

| | | |
|---|---|---|
| | | gtccaccgtcgcgcccgaagaggacaccgaggattccgacaacgaaatcccacaatccggccgtgttcacctgcgccctggc aggccggcatcctgcccgcccaactggtgcccatggtgctcaggtcgagttcaggtcagaatcagaatctctggac gccaacgacatctgcgccatcttcgcgacgctcgacgcctatgccgcccgctgcaaccccaaacgtcgccgcaccggaaga cgccttgcccggccatgcatcgcctcgacgcccaaaaagcaccgaggt |
| 10 | pp65 antigen | MESRGRRCPEMISVLGPISGHVLKAVFSRGDTPVLPHETRLLQTGIHVRVSQPSLILVSQ YTPDSTPCHRGDNQLQVQHTYFTGSEVENVSVNVHNPTGRSICPSQEPMSIYVYALPLKM LNIPSINVHHYPSAAERKHRHLPVADAVIHASGKQMWQARITVSGLAWTRQQNQWKEPDV YYTSAFVFPTKDVALRHVVCAHELVCSMENTRATRKMQVIGDQYVKVYLESFCEDVPSGKL FMHVTLGSDVEEDLTMTRNPQPFMRPHERNGFTVLCPKNMIIKPGKISHIMLDVAFTSHE HFGLLCPKSIPGLSISGNLLMNGQQIFLEVQAIRETVELRQYDPVAALFFFDIDLLLQRG PQYSEHPTFTSQYRIQGKLEYRHTWDRHDEGAAQGDDDVWTSGSDSDEELVTTERKTPRV TGGGAMAGASTSAGRKRKSASSATACTSGVMTRGRLKAESTVAPEEDTDEDSDNEIHNPA VETWPPWQAGILARNLVPMVATVQGQNLKYQEFFWDANDIYRIFAELEGVWQPAAQPKRR RHRQDALPGPCIASTPKKHRG |
| 11 | SecSignal-pp65 antigen-HLA class I TM-CM | atgcggtcacgcgccccgaccctcatcctgctctcggagccctgaccgagacctggccgctccctgcaggt cgactctagaggatccaccatgcggtcacgcgccccgaccctcatcctgctctcgggagccctgaccgagacctggccgctccctgcaggt tgaaagccgtgttagtcgcgatacgcagagactgcgactcctgcagacgcgactctttatgcacgtcacgctgggctgaaga cagccctcgctcgatctgtatctcgcagagagtggagaacgtgtcaaggcgccatgccaacatcagctgcccagccagtcagagcagagagcca gtactttacggcgcagcgagtggagaacgtgtccgctcaagatgctcaacatcccagcatcaacgtcaccactcccgtcgcgcgcagcgc tgtcgatctatgtgtaccgcgtgcccgtagctgacgctgtgattcaagcgtcggcaagcagatgtgcaggcgcgtctcacgtctcggact ggcctgaccgcgtcagtgcaaccagtgcaagaccccgaactggtttgctcaccatggaacacgcgcaacaagatgcaggtgacagtgacccac gtcaagttgtacctgcgcgagtccttctgccgaggacgtgcccgaggacgtgcccctggcaagtcacgcctgggctgtgtcccaaaatga gggaccgtgacaggatgaccccgcaaaccttcatgcgccaaccaaagcgagcgcacagcgccatttggcgtgtgctgttccaagagc taatcaaaccgggcacagatctcgcacatcatgctgactgacatcatgctgttgatgaacgggcagcagatctctgagtgagaacatacgagaccgtgga atcccgggcctgagcatctcagttgatcctgtgcctctcaggcaagcttagtaccgacaacaacctgtagtgatatcgacttgctgctgcagcgggact cccactcacgctgctgacagccgtatcgatccagggcaagctatgtagtaccgaccaacctggaacacaacgcagaaacgccctcggcctatgaact gacagagctgtgaccagcagactgtaaccagccaagctggaacacaacgcagaaacgccctcggcctatgaact gccatggcgggcctcacttccgcggccgcacgcatctcgcggccgacgaccgtgcacgtcggcgttatgacac cgcctggcgggcctcacttccgcggccgcacgcatctcgcggccgacgaccgtgcacgtcggcgttatgacac ttcacctgccctaaggcccgtcgaggccccgcatctcgcccgcaaccaaatggcgccaacctgttgcccaatggtgcctacggtcaggaatctgaagta ccagaatcttctctggacgccaaccacatctacccgcatcttcgccgaattgaagcgttatgcagccccgtcgcaaccaaac gtcgcgccaccgaacgtccttgcccagcagttgtgtccacgtgtccagtgtggtgcgctactgtgatgtgaggagaggcaccgaggtgatcatcgtgcatt gttgctggctgctgctgctctccagcgtcgctccagcgtcgccagcctctgatgttgttgttctcacagcttga aggaggagctactctccagcgtgccagcctctgatgttgttgttctcacagcttga |

Fig. 8C

| | | |
|---|---|---|
| 12 | SecSignal-pp65 antigen-HLA class I TM-CM | MRVTAPRTLILLLSGALALTETWAGSLQVDSRGSTMESRGRRCPEMISVLGPISGHVLKA<br>VFSRGDTPVLPHETRLLQTGIHVRVSQPSLILVSQYTPDSTPCHRGDNQLQVQHTYFTGS<br>EVENVSVNVHNPTGRSICPSQEPMSIYVYALPLKMLNIPSINVHHYPSAAERKHRHLPVA<br>DAVIHASGKQMWQARLTVSGLAWTRQQNQWKEPDVYYTSAFVFPTKDVALRHVVCAHELV<br>CSMENTRATKMQVIGDQYVKVYLESFCEDVPSGKLFMHVTLGSDVEEDLTMTRNPQPFMR<br>PHERNGFTVLCPKNMIIKPGKISHIMLDVAFTSHEHFGLLCPKSIPGLSISGNLLMNGQQ<br>IFLEVQAIRETVELRQYDPVAALFFFDIDLLLQRGPQYSEHPTFTSQYRIQGKLEYRHTW<br>DRHDEGAAQGDDDVWTSGSDSDEELVTTERKTPRVTGGGAMAGASTSAGRKRKSASSATA<br>CTSGVMTRGRLKAESTVAPEEDTDEDSDNEIHNPAVFTWPPWQAGILARNLVPMVATVQG<br>QNLKYQEFFWDANDIYRIFAELEGVWQPAAQPKRRRHRQDALPGPCIASTPKKHRGGSIV<br>GIVAGLAVLAVVVIGAVVATVMCRRKSSGGKGGSYSQAASSDSAQGSDVSLTA |
| 13 | SecSignal-pp65 antigen-HLA class II TM-CM | atgcgggtcacggcgccccgaaccctcatcctgctgctctcgggagccctggccctgaccgagacctgggccggctccctgcaggtcga<br>ctctagaggatccaccatggagtcgcgcggtcgccgttgtcccgaaatgatatccgtactgggtcccatttcggggcacgtgctgaaag<br>ccgtgtttagtcgcggcgatacgccggtgctgccgcacgagacgcgactcctgcagacgggtatccacgtacgcgtgagccagccctcg<br>ctgatcttggtatcgcagtacacgcccgactcgacgccatgccaccgcggcgacaatcagctgcaggtgcagcacacgtactttacggg<br>cagcgaggtggagaacgtgtcggtcaacgtgcacaaccccacgggccgaagcatctgccccagccaggagcccatgtcgatctatgtgt<br>acgcgctgccgctcaagatgctgaacatccccagcatcaacgtgcaccactacccgtcggcggccgagcgcaaacaccgacacctgccc<br>gtagctgacgctgtgattcacgcgtcgggcaagcagatgtggcaggcgcgtctcacggtctcgggactggcctggacgcgtcagcagaa<br>ccagtggaaagagcccgacgtctactacacgtcagcgttcgtgtttcccaccaaggacgtggcactgcggcacgtggtgtgcgcgcacg<br>agctggtttgctccatggagaacacgcgcgcaaccaagatgcaggtgataggtgaccagtacgtcaaggtgtacctggagtccttctgc<br>gaggacgtgccctccggcaagctctttatgcacgtcacgctgggctctgacgtggaagaggacctgacgatgacccgcaacccgcaacc<br>cttcatgcgcccccacgagcgcaacggctttacggtgttgtgtcccaaaaatatgataatcaaaccgggcaagatctcgcacatcatgc<br>tggatgtggcttttacctcacacgagcattttgggctgctgtgtcccaagagcatcccgggcctgagcatctcaggtaacctgttgatg<br>aacgggcagcagatcttcctggaggtacaagccatacgcgagaccgtggaactgcgtcagtacgatcccgtggctgcgctcttcttttt<br>cgatatcgacttgctgctgcagcgcgggcctcagtacagcgagcaccccaccttcaccagccagtatcgcatccagggcaagcttgagt<br>accgacacacctgggaccggcacgacgagggtgccgcccagggcgacgacgacgtctggaccagcggatcggactccgacgaagaactc<br>gtaaccaccgagcgcaagacgccccgcgtcaccggcggcggcgccatggcgggcgcctccacttccgcgggccgcaaacgcaaatcagc<br>atcctcggcgacggcgtgcacgtcgggcgttatgacacgcggccgccttaaggccgagtccaccgtcgcgcccgaagaggacaccgacg<br>aggattccgacaacgaaatccacaatccggccgtgttcacctggccgccctggcaggccggcatcctggcccgcaacctggtgcccatg<br>gtggctacggttcagggtcagaatctgaagtaccaggaattcttctgggacgccaacgacatctaccgcatcttcgccgaattggaagg<br>cgtatggcagcccgctgcgcaacccaaacgtcgccgccaccggcaagacgccttgcccgggccatgcatcgcctcgacgcccaaaaagc<br>accgaggtggatcccagagcaagatgctgagtggagtcgggggctttgtgctgggcctgctcttccttggggccggctgttcatctac<br>ttcaggaatcagaaaggacactctggacttcagccaagaggattcctgagctga |
| 14 | SecSignal-pp65 antigen-HLA class II TM-CM | MRVTAPRTLILLLSGALALTETWAGSLQVDSRGSTMESRGRRCPEMISVLGPISGHVLKA<br>VFSRGDTPVLPHETRLLQTGIHVRVSQPSLILVSQYTPDSTPCHRGDNQLQVQHTYFTGS<br>EVENVSVNVHNPTGRSICPSQEPMSIYVYALPLKMLNIPSINVHHYPSAAERKHRHLPVA<br>DAVIHASGKQMWQARLTVSGLAWTRQQNQWKEPDVYYTSAFVFPTKDVALRHVVCAHELV |

Fig. 8D

| | | |
|---|---|---|
| 64 | PRAME variant 1 | CSMENTRATKMQVIGDQYVKVLESFCEDVPSGKLFMHVTLGSDVEEDLTMTRNPQPFMR<br>PHERNGFTVLCPKNMLIKPGKISHIMLDVAFTSHEHFGLLCPKSIPGLSISGNLLMNGQQ<br>IFLEVQAIRETVELRQYDEVAALEEFDIDLLLQRGPQYSEHPTFSQYRIQGKLEYRHTW<br>DRHDEGAAQGDDDVWTSGSDSDEELVTTERKTPRVTGGGANAGASTSAGRKRKSASSATA<br>CTSGVMTRGRLKAESTVAPEEDTDEDSDNEIHNPAVFTWFPWQAGILARNIVPMVATVQG<br>QNLKYQEFFWDANDIYRIFAELEGVWQPAAQPKRRRHRQDALPGPCIASTPEKKHRGGSQS<br>KMLSGVGGFVLGLLFLGAGLFIYFRNQKGHSGLQPRGFLS<br><br>1 atggaacgaa ggcgtttgtg gggttccatt cagagccgat acatcagcat gagtgtgtgg<br>61 acaagcccac ggagacttgt ggagctggca gggcagagcc tgctgaagga tgaggccctg<br>121 gccattgccg ccctggagtt gctgcccagg gagctcttcc cgccactctt catgcagcc<br>181 tttgacggga gacacagcca gaccctgaag gcaatggtgc aggcctgcc cttcacctgc<br>241 ctcccctctgg gagtgctgat gaaggacaa catcttcacc tggagacctt caaagctgtg<br>301 cttgatggac ttgatgtgct ccttgccag gaggttcgcc ccaggagtg gaaacttcaa<br>361 gtgctggatt tacggaagaa ctctcatcag gacttctgga ctgtatgtc tggaaacagg<br>421 gccagtctgt actcattcc agcagccaga gcagctcagc ccatgacaga gaagcgaaaa<br>481 gtagatggtt tgagcacaga ggcagagcag cccttcattc cagtagaggt gctcgtagac<br>541 ctgttcctca aggaaggtgc ctgtgctgt ttgttctcct acctcattga gaaagtgaag<br>601 cgaaagaaaa atgtactacg cctgctgact aagaagctga agattttgc aatgcccatg<br>661 caggatatca agatgatcct gaaaatggtg cagctggact ctattgaaga tttgaagtg<br>721 acttgtacct ggaagctacc cacctggcg aaattttctc cttacctggg ccagatgatt<br>781 aatctgcgta atctcctcct ctcccaatc catgcatctt cctacattc cccggaaag<br>841 gaagagcagt atatcgccca gttcacctct cagttcctca gtcagttgt cctgcagtct<br>901 ctctatgtgt actctttatt tttccttaga ggccgcctgg atcagttgct caggcacgtg<br>961 atgaacccct tggaaaccct ctcaataact aactgccgg tttcggaagg ggatgtgatg<br>1021 catctgtcc agagctgtcc cgtcagtcag ctaagtgtcc tgagtctaag tgggtcatg<br>1081 ctgaccgatg taagtcccga gcccctccaa gtctgctgg agagagcctc tgccaccctc<br>1141 caggacctgg tctttgatga gtgtggatc acggatgatc agctcctgc cctcctgcct<br>1201 tcccctgagcc actgctccca gcttacaacc ttaagcttct acgggaattc catctccata<br>1261 tctgccttgc agagtctcct cagtcacctc gcagcacctc atcggctga gcaatctgac ccacgtgctg<br>1321 tatcctgtcc cctggagag ttatgaggac atccatggta cctccacct ggagaggctt<br>1381 gcctatctgc atgccaggct cagggagttg ctgtgtgagt tgggcgcc cagcatggtc<br>1441 tgcttagtg ccaacccctg tcctcactgt gggacagaa cctttcatga ccggagccc<br>1501 atcctgtgcc cctgtttcat gcctaac |
| 65 | WT1 variant C | 1 atgggctccg acgtgcggga cctgaaccg ctgctgcccg ccgtccctc cctgggtggc<br>61 ggcgcggct gtgccctgcc tgtgagcggc tgtgagcggc tgggcgggcc ccgcgccgcc accggctccg<br>121 gcgccccccg gcgcttcggc ttacggtcg gccttcactcc ttcatcaaac aggagccgag ctggggcggc<br>181 cggcaactcc cgccgcgcc gcctcactcc gcctcactg gccttcactg tcaacttttc cggcagttc<br>241 gcggagccgc acgaggagca gtgcctgagc gccggcacc cctgcagcc cccagccgc<br>301 actggcacag ccggagctg tgctacggg cccttcggtc tgctaccgg aggcaaggcg |

Fig. 8E

|  | 361 tcatccgcc agccaggat ttcgcaatcc ttcgcacgc gtttcctaac gcgccctacc tgccagctg cctcgagagc |
|  | 421 cagcccgcta ttcgcaatcc gggttacagc acggtcacct tcgacgggac gccagctac |
|  | 481 ggtcacacgc cctcgcaca tgcggcgcag ttcccaaacc actcattcaa gcatgaggat |
|  | 541 cccatgggcc agcaggctc gctggtgag cagcagtact cggtgccgcc ccgtgtctat |
|  | 601 ggctgcaca ccccacga cagctgcacc gcagccagg ctttgctgct gaggacgcc |
|  | 661 tacagcagtg acaattata ccaaatgaca tccagcttg aatgcatgac ctgaatcag |
|  | 721 atgaacttag gagccacctt aaaggccaca acacaggt acgagagcga taaccacaca |
|  | 781 acgcccatcc tctgcgagc ccaatacaga atacacacgc acggtgtctt caggcatt |
|  | 841 caggatgtgc gacgtgtgc tggagtagcc cgactcttg tacgtcggc atctagacc |
|  | 901 agtgagaaac gcccttcat gtgtgcttca ccaggctgca ataagagata ttttaagctg |
|  | 961 tcccacttac agatgcacag caggaagcac actggtgaga accatacca gtgtgacttc |
|  | 1021 aaggactgtg aacgaagtt ttctcgttca gaccagctca aaagacacca aaggagacat |
|  | 1081 acaggtgtga aaccattcca gtgtaaaact tgtcagcgaa agttctcccg gtccgaccac |
|  | 1141 ctgaagaccc acaccagac tcatacagt caaacaagtg aaaagcctt cagctgtcgg |
|  | 1201 tggcaagtt gtcagaaaaa gtttgcccgg tcagatgaat tagtccgcca tcacaacatg |
|  | 1261 catcagagaa acatgaccaa actccagctg gcgctt |

| 66 | p53 | 1 atggaggagc cgcagtcaga tcctagcgtc gagcccctc tgagtcagga aacattttca |
|  |  | 61 gacctatgga aactacttcc tgaaaacaac gttctgtccc cctgccgtc ccaagcaatg |
|  |  | 121 gatgatttga tgctgtcccc ggacgatatt gaacaatggt tcactgtgaa cccaggtcca |
|  |  | 181 gatgaagctc ccagatgcc agaggctgct ccccgcgtgg ccctgcacc agcagctcct |
|  |  | 241 acaccggcgg ccccctgcacc agcccctcc tggcccctgt ctggcttct catcttctgt ccttcccag |
|  |  | 301 aaaacctacc aggcagcta cggtttccgt cctgccctc tgcattctgg gacagccaag |
|  |  | 361 tctgtgactt gcacgtactc cctgccctc aacagatgt tttgccaact ggccaagacc |
|  |  | 421 tgccctgtgc agctgtgggt tgattccaca ccccgcccg gcaccgcgt ccgcgccatg |
|  |  | 481 gccatctaca agcagtcaca gcacatgacg gaggttgtga ggcgctgccc ccaccatgag |
|  |  | 541 cgctgctcaa atagcgatgg tctggcccct cctcagcatc cctcagcagt ttatccgagt |
|  |  | 601 ttgcgtgtgg agtattgga tgtttttgga ctttttcgac actttcgac atagtgtgt ggtgcctat |
|  |  | 661 gagccgcctg aggttgcctc tgactgtgcc tgactgtacc accatccact acactacat gtgtaacagt |
|  |  | 721 tcctgcatgg gcggcatgaa ccggaggcc atcctcacca tcatcacact ggaagactcc |
|  |  | 781 agtggtaatc tactgggacg gaacagcttt gaggtgcggt tttgtgcctg tcctgggaga |
|  |  | 841 gaccggcgca cagagagaca gaatctccgc aagaaagggg agcctcacca cgacctgccc |
|  |  | 901 ccagggagca ctaaggagc actgccaaac aacaccagct cctctcccca gccaaagaag |
|  |  | 961 aaaccactgg atggagaata tttcaccctt cagatccgtg ggcgtgagcg cttcgagatg |
|  |  | 1021 ttccgagagc tgaatgaggc cttgaactc aaggatgcc aaggatgccc ggagccaggg |
|  |  | 1081 gggagcaggg ctcactccag ccacctgaag tccaaaaagg gtcagtctac ctcccgccat |
|  |  | 1141 aaaaactca tgttcaagac agaagggcct gactcagac |

Fig. 9

| SEQ ID NO | Type | Name | Sequence |
|---|---|---|---|
| 15 | MHC | HLA-A | PSSQPTIPIVGIIAGLVLFGAVITGAVVAAVMWRRKSSDRKGGSYSQAASSDSAQGSDVSLTACKV |
| 16 | MHC | | GSYSQAASSDSAQGSDVSLTACKV |
| 17 | MHC | HLA-B | PSSQSTVPIVGIVAGLAVLAVVVIGAVVAAVMCRRKSSGGKGGSYSQAACSDSAQGSDVSLTA |
| 18 | MHC | | GSYSQAACSDSAQGSDVSLTA |
| 19 | MHC | HLA-C | PSSQPTIPIVGIVAGLAVLAVLGAMVAVVMCRRKSSGGRGGSCSQAASSNSAQGSDESLIACKA |
| 20 | MHC | | SAQGSDESLIACKA |
| 21 | MHC | HLA-E | PASQPTIPIVGIIAGLVLLGSVVSGAVVAAVIWRKKSSGGKGGSYSKAEWSDSAQGSESHSL |
| 22 | MHC | | GSYSKAEWSDSAQGSESHSL |
| 23 | MHC | HLA-F | QSPQPTIPIVGIVAGLIVLGAVVTGAVVAAVMWRKKSSDRNRGSYSQAAVTDSAQGSGVSLTANKV |
| 24 | MHC | | RNRGSYSQAAVTDSAQGSGVSLTANKV |
| 25 | MHC | HLA-Dra | VVCALGLTVGLVGIIIGTIFLIKGLRKSNAAERRGPL |
| 26 | MHC | | RKSNAAERRGPL |
| 27 | MHC | HLA-DRb | MLSGVGGFVLGLLFLAGLLFLYFRNQKGHSGLQPRGFLS |
| 28 | MHC | | GHSGLQPRGFLS |
| 29 | MHC | HLA-Dqa | VVCALGLSVGIMGIVVGIVVFIIQGLRSVGASRHQGPL |
| 30 | MHC | | VGASRHQGPL |
| 31 | MHC | HLA-DQb | MLSGIGGFVLGLIFLGLGLIIHHRSQKGLLH |
| 32 | MHC | | RSQKGLLH |
| 33 | MHC | HLA-DPa | VLCALGLIVLGLVGIIVGIIVGTVLIIKSLRSGHDPRAQTL |
| 34 | MHC | | RSGHDPRAQTL |
| 35 | MHC | HLA-DPb | TLTGAGGFVLGLIICGVGITMRRSKKVQRGSA |
| 36 | MHC | | SKKVQRGSA |
| 37 | MHC | CD1a | FIILAVIVPLLLLIGLALWFRKRCFC |
| 38 | MHC | | RKRCFC |
| 39 | MHC | CD1b | IVLAIIVPSLLLLLCLALWYMRRRSYQNIP |
| 40 | MHC | | RRRSYQNIP |
| 41 | MHC | CD1c | WIALVIVPLVILIVLVLWFKKHCSYQDIL |
| 42 | MHC | | KKHCSYQDIL |

Fig. 10A

| SEQ ID NO | Type | Name | Sequence |
|---|---|---|---|
| 43 | SNARE | Cis-golgi SNARE p28 | MAAGTSSYWE DLRKQARQLE NELDLKLVSF SKLCTSYSHS STRDGRRDRY SSDTTPLLNG SSQDRMFETM AIEIEQLLAR LTGVNDKMAE YTNSAGVPSL NAALMHTLQR HRDILQDYTH EFHKTKANFM AIRERENLMG SVRKDIESYK SGSGVNNRRT ELFLKEHDHL RNSDRLIEET ISIAMATKEN MTSQRGMLKS IHSKMNTLAN REPAVNSLIQ RINLRKRRDS LLLGGVIGIC TILLLLYAFH |
| 44 | SNARE | VTI1b | MGASLTSPGT QEKLIRDFDE KQQEANKMLT QMEEELHYAP VSFHNPMMSK LQDYQKDLAQ FHLEARTMPG DRGDMKYGTY AVENEHMNRL QSQRAMLLQG TKSLGRATQE TDQIGSEISE ELGNQRDQ |
| 45 | SNARE | Membrin | MDPLFQQTHK QVHEIQSCMG RLETADKQSV HIVENEIQAS IDQIFSRLER LEILSSKEPP NKRQNARLRV DQIKYDVQHL QTALRNFQHR RHAREQQERQ REELLSRTFT TNDSDTTIPM DESLQFNSSL QKVHNGMDDL ILDGHNILDG LRTQRLTLKG TQKKILDIAN MLGLSNTVMR LIEKRAFQDK YFMIGGMLLT CVVMFLVVQY LT |
| 46 | SNARE | Pallidin | MSVPGPSSPD GALTRPPYCL EAGEPTPGLS DTSPDEGLIE DLTIEDKAVE QLAEGILSHY LPDLQRSKQA LQELTQNQVV LLDTLEQEIS KFKECHSMLD INALFAEAKH YHAKLVNIRK EMLMLHEKTS KLKKRALKLQ QKRQKEELER EQQREKEFER EKQLTARPAK RM |
| 47 | SNARE | Syntaxin-5 | MSCRDRTQEF LSACKSLQTR QNGIQTNKPA LRAVRQRSEF TLMAKRIGKD LSNTFAKLEK LTILAKRKSL FDDKAVEIEE LTYIIKQDIN SLNKQIAQLQ DFVRAKGSQS GRHLQTHSNT IVVSLQSKLA SMSNDFKSVL EVRTENLKQQ RSRREQFSRA PVSALPLAPN HLGGAVVLG AESHASKDVA IDMMDSRTSQ QLQLIDEQDS YIQSRADTMQ NIESTIVELG SIFQQLAHMV KEQEETIQRI DENVLGAQLD VEAAHSEILK YFQSVTSNRW LMVKIELILI VFFIEVVFL A |
| 48 | SNARE | Syntaxin-6 | MSMEDPFFVV KGEVQKAVNT AQGLFQRWTE LLQDPSTATR EEIDWTTNEL RNNLRSIEWD LEDLDETISI VEANPRKFNL DATELSIRKA FITSTRQVVR DMKDQMSTSS VQALAERKNR QALLGDSGSQ NWSTGTTDKY GRLDRELQRA NSHFIEEQQA QQQLIVEQQD EQLELVSGSI GVLKNMSQRI GGELEEQAVM LEDFSHELES TQSRLDNVMK KLAKVSHMTS DRRQWCAIAI LFAVLLVVLI LFIVL |
| 49 | SNARE | Syntaxin-7 | MSYTPGVGGD PAQLAQRISS NIQKITQCSV EIQRTLNQLG TPQDSPELRQ QLQQKQQYTN QLAKETDKYI KEFGSLPTTP SEQRQRKIQK DRLVAEFTTS LTNEQKVQRQ AAEREKEFVA RVRASSRVSG SFPEDSSKER NLVSWESQTQ PQVVQDEEI TEDDLRLIHE RESSIRQLEA DIMDINEIFK DLGMMIHEQG DVIDSIEANV ENAEVHVQQA NQQLSRAADY QRKSRKTLCI IILLIIGVA IISLIIWGLN H |

Fig. 10B

| | | | |
|---|---|---|---|
| 50 | SNARE | Syntaxin-8 | MAPDPWFSTY DSTCQIAQEI AEKIQQRNQY ERKGEKAPKL TVTIRALLQN LKEKIALLKD LLLRAVSTHQ ITQLEGDRRQ NLLDDLVTRE RLLLASFKNE GAEPDLIRSS LMSEEAKRGA PNPWLFEEPE ETRGLGFDEI RQQQQKIIQE QDAGLDALSS IISRQKQMGQ EIGNELDEQN EIIDDLANLV ENTDEKLRNE TREVNMVDRK SASCGMIMVI LLLLVAIVVV AVWPTN |
| 51 | SNARE | Syntaxin-10 | MSLEDPFFVV RGEVQKAVNT ARGLYQRWCE LLQESAAVGR EELDWTTNEL RNGLRSIEWD LEDLEETIGI VEANPGKPAA QKSPSDLLDA SAVSATSRYI BEQQATQQLI MDEQDQQLEM VSGSIQVLKH MSGRVGEELD EQGIMLDAFA QEMDHTQSRM DGVLRKLAKV SHMTSDRRQW CAIAVIVGVL LIVLILLFSL |
| 52 | SNARE | SYNTAXIN-10a | MSLEDPFFVV RGEVQKAVNT ARGLYQRWCE LLQESAAVGR EELDWTTNEL RNGLRSIEWD LEDLEETIGI VEANPGKFKL PAGDLQERKV FVERMREAVQ EMKDHMVSPT AVAFLERNNR EILAGKPAAQ KSPSDLLDAS AVSATSRYIE EQQATQQLIM DEQDQQLEMV SGSIQVLKHM SGRVGEELDE QGIMLDAFAQ EMDHTQSRMD GVLRKLAKVS HMTSDRRQWC AIAVLVGVLL LVLILLFSL |
| 53 | SNARE | Syntaxin-11 | MKDRLAELLD LSKQYDQQFP DGDDEFDSPH EDIVFETDHI LESLYRDIRD IQDENQLLVA DVKRLGKQNA RFLTSMRRLS SIKRDTNSIA KAFRARGEVI HCKLRAMKEL SEAAEAQHGP HSAVARISRA QYNALTLTFQ RAMHDYNQAE MKQRDNCKIR IQRQLEIMGK EVSGDQIEDM FEQGKWDVFS ENLLADVKGR GPFTTRSRAA TANCCAWRAA IRDVHELFLQ MAVLVEKQAD TLNVIELNVQ KTVDYTGQAK AQVRKAVQYE EKNPCRTLCC FCCPCLK |
| 54 | SNARE | Syntaxin-12 | MSYGPLDMYR NPGPSGPQLR DFSSIIQTCS GNIQRISQAT AQIKNLMSQL GTKQDSSKLQ ENLQQLQHST NQLAKETNEL IKELGSLPLP LSTSEQRQQR LQKERLMNDF SAALNNFQAV QRRVSEKEKE SIARARAGSR LSAEERQREE QLVSFDSHEE WNQMQSQEDE VAITEQDLEL IKERETAIRQ LEADILDVNQ IFKDLAMMIH DQGDLIDSIE ANVESSEVHV ERATEQLQRA AYYQKKSRKK MCILVLVLSV IILILGLIIW IVYKTK |
| 55 | | Syntaxin-17 | MSEDEEKVKL RRLEPAIQKF IKIVIPTNLE RLRKHQINIE KYQRCRIWDK LHEEHINAGR TVQQLRSNIR EIEKLCLKVR KDDLVLLKRM IDPVKEEASA ATAEFLQLHL ESVEELKKQF NDEETLLQPP LTRSMTVGGA FHTTEAEASS QSLTQIYALP EIPQDQNAAE SRETLEADLI ELSQLVTDFS LLVNSQQEKI DSIADHVNSA AVNVEEGTKN LGKAAKYKLA ALPVAGALIG GMVGGPIGLL ACFKVAGIAA ALGGGVLGFT GGKLIQRKKQ KMMEKLTSSC PDLPSQTDKK CS |
| 56 | SNARE | VAMP-2 | MSATAATAPP AAPAGEGGPP APPPNLTSNR RLQQTQAQVD EVVDIMRVNV DKVLERDQKL SELDDRADAL QAGASQFETS AAKLKRKYWW KNLKMMIILG VICAIILIII IVYFSS |
| 57 | SNARE | VAMP-3 | MSTGPTAATG SNRRLQQTQN QVDEVVDIMR VNVDKVLERD QKLSELDDRA DALQAGASQF ETSAAKLKRK YWWKNCKMWA IGITVLVIFI IIIIVWVVSS |

Fig. 10C

| | | | |
|---|---|---|---|
| 58 | SNARE | VAMP-4 | MPPKFKRHLN DDDVTGSVKS ERRNLLEDDS DEEEDFELRG PSGPREGPRN DKIKHVQNQV DEVIDVMPEN ITKVIERGER LDELQDKSES LSDNATAFSN RSKQLRRQMW WRGCKIKAIM ALVAAILLLV IILILIVMKYR T |
| 59 | SNARE | VAMP-7 | MAILFAVVAR GTTILAKHAW CGGNFLEVTE QILAKIPSEN NKLTYSHGNY LFHYICQDRI VYLCITDDDF ERSRAFNFLN EIKKRFQTTY GSRAQTALPY AMNSEFSSVL AAQLKHHSEN KGLDKVMETQ AQVDELKGIM VRNIDLVAQR GERLELLIDK TENLVDSSVT FKTTSRNLAR AMCMKNLKLT IIIIVSIVF IYIIVSPLCG GFTWPSCVKK |
| 60 | SNARE | VAMP8 | MEEASEGGGN DRVRNLQSEV EGVKNIMTQN VERILARGEN LEHLRNKTED LEATSEHFKT TSQKVARKFW WKNVKMIVLI CVIVEIILF IVLFATGAFS |
| 61 | SNARE | VTT1-a-beta | MSSDFEGYEQ DFAVLTAEIT SKIARVPRLP PDEKKQMVAN VEKQLEEAKE LLEQMDLEVR EIPPQSRGMY SNRMRSYKQE MGKLETDFKR SRIAYSDEVR NELLGDDGNS SENQRAHLLD NTERLERSSR RLEAGYQIAV ETEQIGQEML ENLSHDREKI QRARERLRET DANLGKSSRI LTGMLRRGCS VKKQCNLSLA PKA |
| 62 | SNARE | XP350893 | MRDRLPDLTA CRKNDDGDTV VVVEKDHFMD DFFHQVEEIR NSIDKITQYV EEVKKNHSII LSAPNPEGKI KEELEDLNKE IKKTANKIRA KLKAIEQSFD QDESGNRISV DLRIRRTQHS VLSRKFVEAM AEYNEAQTLF RERSKGRIQR QLEITGRTTT DDELEEMLES GKPSIFTSDI ISDSQITRQA LNEIESRHKD IMKLETSIRE LHEMEMDMAM FVETQGEMIN NIERNVMNAT DYVEHAKEET RKAIKYQSKA RRVSLASKN |
| 63 | SNARE | LIP5 | QMAALAPLPP LPAQFKSIQH HLRTAQEHDK RDPVVAYYCR LYAMQTGMKI DSKTPECRKF LSKLMDQLEA LKKQLGDNEA ITQEIVGCAX LENYALKMFL YADNEDRAGR FHKNMIKSFY TASLLIDVIT VFGELTDENV KHRKYARWKA TYIHNCLKEW GDSSSRPCWE LKKIMILKKM KMLEQPLCPL SQLSHHHLQL MTQQHAIRQL YWNTDSSGCT RSS |

SEQUENCE LISTING

```
<160> NUMBER OF SEQ ID NOS: 66

<210> SEQ ID NO 1
<211> LENGTH: 78
<212> TYPE: DNA
<213> ORGANISM: Homo sapiens

<400> SEQUENCE: 1
atgcgggtca cggcgccccg aaccctcatc ctgctgctct cgggagccct ggccctgacc      60
gagacctggg ccggctcc                                                    78

<210> SEQ ID NO 2
<211> LENGTH: 26
<212> TYPE: PRT
<213> ORGANISM: Homo sapiens

<400> SEQUENCE: 2

Met Arg Val Thr Ala Pro Arg Thr Leu Ile Leu Leu Leu Ser Gly Ala
1               5                   10                  15

Leu Ala Leu Thr Glu Thr Trp Ala Gly Ser
            20                  25

<210> SEQ ID NO 3
<211> LENGTH: 168
<212> TYPE: DNA
<213> ORGANISM: Homo sapiens

<400> SEQUENCE: 3
atcgtgggca ttgttgctgg cctggctgtc ctagcagttg tggtcatcgg agctgtggtc      60
gctactgtga tgtgtaggag gaagagctca ggtggaaaag gagggagcta ctctcaggct     120
gcgtccagcg acagtgccca gggctctgat gtgtctctca cagcttga                 168

<210> SEQ ID NO 4
<211> LENGTH: 55
<212> TYPE: PRT
<213> ORGANISM: Homo sapiens

<400> SEQUENCE: 4

Ile Val Gly Ile Val Ala Gly Leu Ala Val Leu Ala Val Val Val Ile
1               5                   10                  15

Gly Ala Val Val Ala Thr Val Met Cys Arg Arg Lys Ser Ser Gly Gly
            20                  25                  30
```

Lys Gly Gly Ser Tyr Ser Gln Ala Ala Ser Ser Asp Ser Ala Gln Gly
            35                  40                  45

Ser Asp Val Ser Leu Thr Ala
        50                  55

<210> SEQ ID NO 5
<211> LENGTH: 129
<212> TYPE: DNA
<213> ORGANISM: Homo sapiens

<400> SEQUENCE: 5
cagagcaaga tgctgagtgg agtcgggggc tttgtgctgg gcctgctctt ccttggggcc      60
gggctgttca tctacttcag gaatcagaaa ggacactctg gacttcagcc aagaggattc     120
ctgagctga                                                             129

<210> SEQ ID NO 6
<211> LENGTH: 42
<212> TYPE: PRT
<213> ORGANISM: Homo sapiens

<400> SEQUENCE: 6

Gln Ser Lys Met Leu Ser Gly Val Gly Gly Phe Val Leu Gly Leu Leu
1               5                   10                  15

Phe Leu Gly Ala Gly Leu Phe Ile Tyr Phe Arg Asn Gln Lys Gly His
            20                  25                  30

Ser Gly Leu Gln Pro Arg Gly Phe Leu Ser
        35                  40

<210> SEQ ID NO 7
<211> LENGTH: 24
<212> TYPE: DNA
<213> ORGANISM: Artificial Sequence
<220> FEATURE:
<223> OTHER INFORMATION: DNA of restriction site in human HLA class I
      domains

<400> SEQUENCE: 7
ctgcaggtcg actctagagg atcc                                            24

<210> SEQ ID NO 8
<211> LENGTH: 8
<212> TYPE: PRT
<213> ORGANISM: Artificial Sequence
<220> FEATURE:
<223> OTHER INFORMATION: Restriction site in human HLA class I domains

<400> SEQUENCE: 8

Leu Gln Val Asp Ser Arg Gly Ser
1               5

<210> SEQ ID NO 9
<211> LENGTH: 1683
<212> TYPE: DNA
<213> ORGANISM: Human cytomegalovirus

<400> SEQUENCE: 9
atggagtcgc gcggtcgccg ttgtcccgaa atgatatccg tactgggtcc catttcgggg      60
cacgtgctga aagccgtgtt tagtcgcggc gatacgccgg tgctgccgca cgagacgcga     120
ctcctgcaga cgggtatcca cgtacgcgtg agccagccct cgctgatctt ggtatcgcag     180
tacacgcccg actcgacgcc atgccaccgc ggcgacaatc agctgcaggt gcagcacacg     240

-continued

```
tactttacgg gcagcgaggt ggagaacgtg tcggtcaacg tgcacaaccc cacgggccga      300
agcatctgcc ccagccagga gcccatgtcg atctatgtgt acgcgctgcc gctcaagatg      360
ctgaacatcc ccagcatcaa cgtgcaccac tacccgtcgg cggccgagcg caaacaccga      420
cacctgcccg tagctgacgc tgtgattcac gcgtcgggca gcagatgtg gcaggcgcgt       480 ctcacggtct cgggactggc ctggacgcgt cagcagaacc agtggaaaga gcccgacgtc      540
tactacacgt cagcgttcgt gtttcccacc aaggacgtgg cactgcggca cgtggtgtgc      600
gcgcacgagc tggtttgctc catggagaac acgcgcgcaa ccaagatgca ggtgataggt      660
gaccagtacg tcaaggtgta cctggagtcc ttctgcgagg acgtgccctc cggcaagctc      720
tttatgcacg tcacgctggg ctctgacgtg aagaggacc tgacgatgac ccgcaacccg       780 caaccttca tgcgccccca cgagcgcaac ggctttacgg tgttgtgtcc caaaaatatg       840
ataatcaaac cgggcaagat ctcgcacatc atgctggatg tggcttttac ctcacacgag      900
cattttgggc tgctgtgtcc caagagcatc ccggggcctga gcatctcagg taacctgttg      960
atgaacgggc agcagatctt cctggaggta caagccatac gcgagaccgt ggaactgcgt      1020
cagtacgatc ccgtggctgc gctcttcttt ttcgatatcg acttgctgct gcagcgcggg      1080
cctcagtaca gcgagcaccc caccttcacc agccagtatc gcatccaggg caagcttgag      1140
taccgacaca cctgggaccg gcacgacgag ggtgccgccc agggcgacga cgacgtctgg      1200
accagcggat cggactccga cgaagaactc gtaaccaccg agcgcaagac gccccgcgtc      1260
accggcggcg cgccatggc gggcgcctcc acttccgcgg ccgcaaacg caaatcagca       1320 tcctcggcga cggcgtgcac gtcgggcgtt atgacacgcg gccgcttaa ggccgagtcc       1380 accgtcgcgc ccgaagagga caccgacgag gattccgaca cgaaatcca caatccggcc      1440 gtgttcacct ggccgccctg gcaggccggc atcctggccc gcaacctggt gcccatggtg      1500
gctacggttc agggtcagaa tctgaagtac caggaattct tctgggacgc caacgacatc      1560
taccgcatct tcgccgaatt ggaaggcgta tggcagcccg ctgcgcaacc caaacgtcgc      1620
cgccaccggc aagacgcctt gcccgggcca tgcatcgcct cgacgcccaa aaagcaccga      1680
ggt                                                                    1683
```

<210> SEQ ID NO 10
<211> LENGTH: 561
<212> TYPE: PRT
<213> ORGANISM: Human cytomegalovirus

<400> SEQUENCE: 10

```
Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
```

```
                  115                 120                 125
His His Tyr Pro Ser Ala Ala Glu Arg Lys His Arg His Leu Pro Val
             130                 135                 140
Ala Asp Ala Val Ile His Ala Ser Gly Lys Gln Met Trp Gln Ala Arg
145                 150                 155                 160
Leu Thr Val Ser Gly Leu Ala Trp Thr Arg Gln Gln Asn Gln Trp Lys
                 165                 170                 175
Glu Pro Asp Val Tyr Tyr Thr Ser Ala Phe Val Phe Pro Thr Lys Asp
                 180                 185                 190
Val Ala Leu Arg His Val Val Cys Ala His Glu Leu Val Cys Ser Met
                 195                 200                 205
Glu Asn Thr Arg Ala Thr Lys Met Gln Val Ile Gly Asp Gln Tyr Val
             210                 215                 220
Lys Val Tyr Leu Glu Ser Phe Cys Glu Asp Val Pro Ser Gly Lys Leu
225                 230                 235                 240
Phe Met His Val Thr Leu Gly Ser Asp Val Glu Glu Asp Leu Thr Met
                 245                 250                 255
Thr Arg Asn Pro Gln Pro Phe Met Arg Pro His Glu Arg Asn Gly Phe
             260                 265                 270
Thr Val Leu Cys Pro Lys Asn Met Ile Ile Lys Pro Gly Lys Ile Ser
             275                 280                 285
His Ile Met Leu Asp Val Ala Phe Thr Ser His Glu His Phe Gly Leu
             290                 295                 300
Leu Cys Pro Lys Ser Ile Pro Gly Leu Ser Ile Ser Gly Asn Leu Leu
305                 310                 315                 320
Met Asn Gly Gln Gln Ile Phe Leu Glu Val Gln Ala Ile Arg Glu Thr
                 325                 330                 335
Val Glu Leu Arg Gln Tyr Asp Pro Val Ala Ala Leu Phe Phe Phe Asp
                 340                 345                 350
Ile Asp Leu Leu Leu Gln Arg Gly Pro Gln Tyr Ser Glu His Pro Thr
             355                 360                 365
Phe Thr Ser Gln Tyr Arg Ile Gln Gly Lys Leu Glu Tyr Arg His Thr
             370                 375                 380
Trp Asp Arg His Asp Glu Gly Ala Ala Gln Gly Asp Asp Val Trp
385                 390                 395                 400
Thr Ser Gly Ser Asp Ser Asp Glu Glu Leu Val Thr Thr Glu Arg Lys
                 405                 410                 415
Thr Pro Arg Val Thr Gly Gly Gly Ala Met Ala Gly Ala Ser Thr Ser
                 420                 425                 430
Ala Gly Arg Lys Arg Lys Ser Ala Ser Ser Ala Thr Ala Cys Thr Ser
             435                 440                 445
Gly Val Met Thr Arg Gly Arg Leu Lys Ala Glu Ser Thr Val Ala Pro
             450                 455                 460
Glu Glu Asp Thr Asp Glu Asp Ser Asp Asn Glu Ile His Asn Pro Ala
465                 470                 475                 480
Val Phe Thr Trp Pro Pro Trp Gln Ala Gly Ile Leu Ala Arg Asn Leu
                 485                 490                 495
Val Pro Met Val Ala Thr Val Gln Gly Gln Asn Leu Lys Tyr Gln Glu
                 500                 505                 510
Phe Phe Trp Asp Ala Asn Asp Ile Tyr Arg Ile Phe Ala Glu Leu Glu
             515                 520                 525
Gly Val Trp Gln Pro Ala Ala Gln Pro Lys Arg Arg His Arg Gln
530                 535                 540
```

Asp Ala Leu Pro Gly Pro Cys Ile Ala Ser Thr Pro Lys Lys His Arg
545                 550                 555                 560

Gly

<210> SEQ ID NO 11
<211> LENGTH: 1962
<212> TYPE: DNA
<213> ORGANISM: Artificial Sequence
<220> FEATURE:
<223> OTHER INFORMATION: DNA encoding human HLA class I domains and CMV
      pp65

<400> SEQUENCE: 11

| | | | | | |
|---|---|---|---|---|---|
| atgcgggtca | cggcgcccg | aaccctcatc | ctgctgctct | cgggagccct | ggccctgacc | 60 |
| gagacctggg | ccggctccct | gcaggtcgac | tctagaggat | ccaccatgga | gtcgcgcggt | 120 |
| cgccgttgtc | ccgaaatgat | atccgtactg | ggtcccattt | cggggcacgt | gctgaaagcc | 180 |
| gtgtttagtc | gcgcgatac | gccggtgctg | ccgcacgaga | cgcgactcct | gcagacgggt | 240 |
| atccacgtac | gcgtgagcca | gccctcgctg | atcttggtat | cgcagtacac | gcccgactcg | 300 |
| acgccatgcc | accgcggcga | caatcagctg | caggtcagc | acgtactt | tacgggcagc | 360 |
| gaggtggaga | cgtgtcggt | caacgtgcac | aaccccacgg | gccgaagcat | ctgccccagc | 420 |
| caggagccca | tgtcgatcta | tgtgtacgcg | ctgccgctca | agatgctgaa | catccccagc | 480 |
| atcaacgtgc | accactaccc | gtcggcggcc | gagcgcaaac | accgacacct | gcccgtagct | 540 |
| gacgctgtga | ttcacgcgtc | gggcaagcag | atgtggcagg | cgcgtctcac | ggtctcggga | 600 |
| ctggcctgga | cgcgtcagca | gaaccagtgg | aaagagcccg | acgtctacta | cacgtcagcg | 660 |
| ttcgtgtttc | ccaccaagga | cgtggcactg | cggcacgtgg | tgtgcgcgca | cgagctggtt | 720 |
| tgctccatgg | agaacacgcg | cgcaaccaag | atgcaggtga | taggtgacca | gtacgtcaag | 780 |
| gtgtacctgg | agtccttctg | cgaggacgtg | ccctccggca | agctctttat | gcacgtcacg | 840 |
| ctgggctctg | acgtggaaga | ggacctgacg | atgacccgca | accgcaaacc | cttcatgcgc | 900 |
| ccccacgagc | gcaacggctt | tacggtgttg | tgtcccaaaa | atatgataat | caaaccgggc | 960 |
| aagatctcgc | acatcatgct | ggatgtggct | tttacctcac | acgagcattt | tgggctgctg | 1020 |
| tgtcccaaga | gcatcccggg | cctgagcatc | tcaggtaacc | tgttgatgaa | cgggcagcag | 1080 |
| atcttcctgg | aggtacaagc | catacgcgag | accgtgaac | tgcgtcagta | cgatcccgtg | 1140 |
| gctgcgctct | tctttttcga | tatcgacttg | ctgctgcagc | gcgggcctca | gtacagcgag | 1200 |
| caccccacct | tcaccagcca | gtatcgcatc | cagggcaagc | ttgagtaccg | acacacctgg | 1260 |
| gaccggcacg | acgagggtgc | cgcccagggc | gacgacgacg | tctggaccag | cggatcggac | 1320 |
| tccgacgaag | aactcgtaac | caccgagcgc | aagacgcccc | gcgtcaccgg | cggcggcgcc | 1380 |
| atggcgggcg | cctccacttc | cgcgggccgc | aaacgcaaat | cagcatcctc | ggcgacggcg | 1440 |
| tgcacgtcgg | gcgttatgac | acggcggcgc | cttaaggccg | agtccaccgt | cgcgcccgaa | 1500 |
| gaggacaccg | acgaggattc | cgacaacgaa | atccacaatc | cggccgtgtt | cacctggccg | 1560 |
| ccctggcagg | ccggcatcct | ggcccgcaac | ctggtgccca | tggtggctac | ggttcagggt | 1620 |
| cagaatctga | agtaccagga | attcttctgg | gacgccaacg | acatctaccg | catcttcgcc | 1680 |
| gaattggaag | gctatggca | gccgctgcg | caacccaaac | gtcgccgcca | ccggcaagac | 1740 |
| gccttgcccg | ggccatgcat | cgcctcgacg | cccaaaaagc | accgaggtgg | atccatcgtg | 1800 |
| ggcattgttg | ctggcctggc | tgtcctagca | gttgtggtca | tcggagctgt | ggtcgctact | 1860 |
| gtgatgtgta | ggaggaagag | ctcaggtgga | aaggaggga | gctactctca | ggctgcgtcc | 1920 | agcgacagtg cccagggctc tgatgtgtct ctcacagctt ga                1962

<210> SEQ ID NO 12
<211> LENGTH: 653
<212> TYPE: PRT
<213> ORGANISM: Artificial Sequence
<220> FEATURE:
<223> OTHER INFORMATION: Fusion protein of human HLA class I domains and CMV pp65

<400> SEQUENCE: 12

```
Met Arg Val Thr Ala Pro Arg Thr Leu Ile Leu Leu Ser Gly Ala
1               5                   10                  15

Leu Ala Leu Thr Glu Thr Trp Ala Gly Ser Leu Gln Val Asp Ser Arg
            20                  25                  30

Gly Ser Thr Met Glu Ser Arg Gly Arg Arg Cys Pro Glu Met Ile Ser
                35                  40                  45

Val Leu Gly Pro Ile Ser Gly His Val Leu Lys Ala Val Phe Ser Arg
50                  55                  60

Gly Asp Thr Pro Val Leu Pro His Glu Thr Arg Leu Leu Gln Thr Gly
65                  70                  75                  80

Ile His Val Arg Val Ser Gln Pro Ser Leu Ile Leu Val Ser Gln Tyr
                85                  90                  95

Thr Pro Asp Ser Thr Pro Cys His Arg Gly Asp Asn Gln Leu Gln Val
            100                 105                 110

Gln His Thr Tyr Phe Thr Gly Ser Glu Val Glu Asn Val Ser Val Asn
        115                 120                 125

Val His Asn Pro Thr Gly Arg Ser Ile Cys Pro Ser Gln Glu Pro Met
130                 135                 140

Ser Ile Tyr Val Tyr Ala Leu Pro Leu Lys Met Leu Asn Ile Pro Ser
145                 150                 155                 160

Ile Asn Val His His Tyr Pro Ser Ala Ala Glu Arg Lys His Arg His
                165                 170                 175

Leu Pro Val Ala Asp Ala Val Ile His Ala Ser Gly Lys Gln Met Trp
            180                 185                 190

Gln Ala Arg Leu Thr Val Ser Gly Leu Ala Trp Thr Arg Gln Gln Asn
        195                 200                 205

Gln Trp Lys Glu Pro Asp Val Tyr Tyr Thr Ser Ala Phe Val Phe Pro
210                 215                 220

Thr Lys Asp Val Ala Leu Arg His Val Val Cys Ala His Glu Leu Val
225                 230                 235                 240

Cys Ser Met Glu Asn Thr Arg Ala Thr Lys Met Gln Val Ile Gly Asp
                245                 250                 255

Gln Tyr Val Lys Val Tyr Leu Glu Ser Phe Cys Glu Asp Val Pro Ser
            260                 265                 270

Gly Lys Leu Phe Met His Val Thr Leu Gly Ser Asp Val Glu Glu Asp
        275                 280                 285

Leu Thr Met Thr Arg Asn Pro Gln Pro Phe Met Arg Pro His Glu Arg
290                 295                 300

Asn Gly Phe Thr Val Leu Cys Pro Lys Asn Met Ile Ile Lys Pro Gly
305                 310                 315                 320

Lys Ile Ser His Ile Met Leu Asp Val Ala Phe Thr Ser His Glu His
                325                 330                 335

Phe Gly Leu Leu Cys Pro Lys Ser Ile Pro Gly Leu Ser Ile Ser Gly
            340                 345                 350

Asn Leu Leu Met Asn Gly Gln Gln Ile Phe Leu Glu Val Gln Ala Ile
```

-continued

```
                355                 360                 365
Arg Glu Thr Val Glu Leu Arg Gln Tyr Asp Pro Val Ala Ala Leu Phe
        370                 375                 380

Phe Phe Asp Ile Asp Leu Leu Leu Gln Arg Gly Pro Gln Tyr Ser Glu
385                 390                 395                 400

His Pro Thr Phe Thr Ser Gln Tyr Arg Ile Gln Gly Lys Leu Glu Tyr
                405                 410                 415

Arg His Thr Trp Asp Arg His Asp Glu Gly Ala Ala Gln Gly Asp Asp
            420                 425                 430

Asp Val Trp Thr Ser Gly Ser Asp Ser Asp Glu Glu Leu Val Thr Thr
                435                 440                 445

Glu Arg Lys Thr Pro Arg Val Thr Gly Gly Gly Ala Met Ala Gly Ala
            450                 455                 460

Ser Thr Ser Ala Gly Arg Lys Arg Lys Ser Ala Ser Ser Ala Thr Ala
465                 470                 475                 480

Cys Thr Ser Gly Val Met Thr Arg Gly Arg Leu Lys Ala Glu Ser Thr
                485                 490                 495

Val Ala Pro Glu Glu Asp Thr Asp Glu Asp Ser Asp Asn Glu Ile His
            500                 505                 510

Asn Pro Ala Val Phe Thr Trp Pro Pro Trp Gln Ala Gly Ile Leu Ala
        515                 520                 525

Arg Asn Leu Val Pro Met Val Ala Thr Val Gln Gly Gln Asn Leu Lys
    530                 535                 540

Tyr Gln Glu Phe Phe Trp Asp Ala Asn Asp Ile Tyr Arg Ile Phe Ala
545                 550                 555                 560

Glu Leu Glu Gly Val Trp Gln Pro Ala Ala Gln Pro Lys Arg Arg Arg
                565                 570                 575

His Arg Gln Asp Ala Leu Pro Gly Pro Cys Ile Ala Ser Thr Pro Lys
            580                 585                 590

Lys His Arg Gly Gly Ser Ile Val Gly Ile Val Ala Gly Leu Ala Val
        595                 600                 605

Leu Ala Val Val Val Ile Gly Ala Val Val Ala Thr Val Met Cys Arg
    610                 615                 620

Arg Lys Ser Ser Gly Gly Lys Gly Gly Ser Tyr Ser Gln Ala Ala Ser
625                 630                 635                 640

Ser Asp Ser Ala Gln Gly Ser Asp Val Ser Leu Thr Ala
                645                 650

<210> SEQ ID NO 13
<211> LENGTH: 1923
<212> TYPE: DNA
<213> ORGANISM: Artificial Sequence
<220> FEATURE:
<223> OTHER INFORMATION: DNA encoding human HLA class I/II domains and
      CMV pp65

<400> SEQUENCE: 13
atgcgggtca cggcgccccg aaccctcatc ctgctgctct cgggagccct ggccctgacc      60
gagacctggg ccggctccct gcaggtcgac tctagaggat ccaccatgga gtcgcgcggt     120
cgccgttgtc ccgaaatgat atccgtactg gtcccatttt cggggcacgt gctgaaagcc     180
gtgtttagtc gcggcgatac gccggtgctg ccgcacgaga cgcgactcct gcagacgggt     240
atccacgtac gcgtgagcca gccctcgctg atcttggtat cgcagtacac gcccgactcg     300
acgccatgcc accgcggcga caatcagctg caggtgcagc acacgtactt tacgggcagc     360
gaggtggaga acgtgtcggt caacgtgcac aaccccacgg ccgaagcat ctgccccagc     420
```

```
caggagccca tgtcgatcta tgtgtacgcg ctgccgctca agatgctgaa catccccagc    480
atcaacgtgc accactaccc gtcggcggcc gagcgcaaac accgacacct gcccgtagct    540
gacgctgtga ttcacgcgtc gggcaagcag atgtggcagg cgcgtctcac ggtctcggga    600
ctggcctgga cgcgtcagca gaaccagtgg aaagagcccg acgtctacta cacgtcagcg    660
ttcgtgtttc ccaccaagga cgtggcactg cggcacgtgg tgtgcgcgca cgagctggtt    720
tgctccatgg agaacacgcg cgcaaccaag atgcaggtga taggtgacca gtacgtcaag    780
gtgtacctgg agtccttctg cgaggacgtg ccctccggca agctctttat gcacgtcacg    840
ctgggctctg acgtggaaga ggacctgacg atgacccgca acccgcaacc cttcatgcgc    900
ccccacgagc gcaacggctt tacggtgttg tgtcccaaaa atatgataat caaaccgggc    960
aagatctcgc acatcatgct ggatgtggct tttacctcac acgagcattt tgggctgctg   1020
tgtcccaaga gcatcccggg cctgagcatc tcaggtaacc tgttgatgaa cgggcagcag   1080
atcttcctgg aggtacaagc catacgcgag accgtggaac tgcgtcagta cgatcccgtg   1140
gctgcgctct ctttttcga tatcgacttg ctgctgcagc gcgggcctca gtacagcgag   1200 cacccccacct tcaccagcca gtatcgcatc cagggcaagc ttgagtaccg acacacctgg   1260
gaccggcacg acgagggtgc cgcccagggc gacgacgacg tctggaccag cggatcggac   1320
tccgacgaag aactcgtaac caccgagcgc aagacgcccc gcgtcaccgg cggcggcgcc   1380
atggcgggcg cctccacttc cgcgggccgc aaacgcaaat cagcatcctc ggcgacggcg   1440
tgcacgtcgg gcgttatgac acgcggccgc cttaaggccg agtccaccgt cgcgcccgaa   1500
gaggacaccg acgaggattc cgacaacgaa atccacaatc cggccgtgtt cacctggccg   1560
ccctggcagg ccggcatcct ggcccgcaac ctggtgccca tggtggctac ggttcagggt   1620
cagaatctga agtaccagga attcttctgg gacgccaacg acatctaccg catcttcgcc   1680
gaattggaag cgtatggca gcccgctgcg caacccaaac gtcgccgcca ccggcaagac   1740
gccttgcccg ggccatgcat cgcctcgacg cccaaaaagc accgaggtgg atcccagagc   1800
aagatgctga gtggagtcgg gggctttgtg ctgggcctgc tcttccttgg ggccgggctg   1860
ttcatctact tcaggaatca gaaaggacac tctggacttc agccaagagg attcctgagc   1920
tga                                                                 1923
```

<210> SEQ ID NO 14
<211> LENGTH: 640
<212> TYPE: PRT
<213> ORGANISM: Artificial Sequence
<220> FEATURE:
<223> OTHER INFORMATION: Human HLA class I/II domains and CMV pp65
      fusion protein

<400> SEQUENCE: 14

Met Arg Val Thr Ala Pro Arg Thr Leu Ile Leu Leu Leu Ser Gly Ala
1               5                   10                  15

Leu Ala Leu Thr Glu Thr Trp Ala Gly Ser Leu Gln Val Asp Ser Arg
            20                  25                  30

Gly Ser Thr Met Glu Ser Arg Gly Arg Arg Cys Pro Glu Met Ile Ser
        35                  40                  45

Val Leu Gly Pro Ile Ser Gly His Val Leu Lys Ala Val Phe Ser Arg
    50                  55                  60

Gly Asp Thr Pro Val Leu Pro His Glu Thr Arg Leu Leu Gln Thr Gly
65                  70                  75                  80

Ile His Val Arg Val Ser Gln Pro Ser Leu Ile Leu Val Ser Gln Tyr

```
              85                  90                  95
Thr Pro Asp Ser Thr Pro Cys His Arg Gly Asp Asn Gln Leu Gln Val
            100                 105                 110
Gln His Thr Tyr Phe Thr Gly Ser Glu Val Glu Asn Val Ser Val Asn
            115                 120                 125
Val His Asn Pro Thr Gly Arg Ser Ile Cys Pro Ser Gln Glu Pro Met
            130                 135                 140
Ser Ile Tyr Val Tyr Ala Leu Pro Leu Lys Met Leu Asn Ile Pro Ser
145                 150                 155                 160
Ile Asn Val His His Tyr Pro Ser Ala Ala Glu Arg Lys His Arg His
                165                 170                 175
Leu Pro Val Ala Asp Ala Val Ile His Ala Ser Gly Lys Gln Met Trp
            180                 185                 190
Gln Ala Arg Leu Thr Val Ser Gly Leu Ala Trp Thr Arg Gln Gln Asn
            195                 200                 205
Gln Trp Lys Glu Pro Asp Val Tyr Tyr Thr Ser Ala Phe Val Phe Pro
            210                 215                 220
Thr Lys Asp Val Ala Leu Arg His Val Cys Ala His Glu Leu Val
225                 230                 235                 240
Cys Ser Met Glu Asn Thr Arg Ala Thr Lys Met Gln Val Ile Gly Asp
                245                 250                 255
Gln Tyr Val Lys Val Tyr Leu Glu Ser Phe Cys Glu Asp Val Pro Ser
            260                 265                 270
Gly Lys Leu Phe Met His Val Thr Leu Gly Ser Asp Val Glu Glu Asp
            275                 280                 285
Leu Thr Met Thr Arg Asn Pro Gln Pro Phe Met Arg Pro His Glu Arg
            290                 295                 300
Asn Gly Phe Thr Val Leu Cys Pro Lys Asn Met Ile Ile Lys Pro Gly
305                 310                 315                 320
Lys Ile Ser His Ile Met Leu Asp Val Ala Phe Thr Ser His Glu His
                325                 330                 335
Phe Gly Leu Leu Cys Pro Lys Ser Ile Pro Gly Leu Ser Ile Ser Gly
            340                 345                 350
Asn Leu Leu Met Asn Gly Gln Gln Ile Phe Leu Glu Val Gln Ala Ile
            355                 360                 365
Arg Glu Thr Val Glu Leu Arg Gln Tyr Asp Pro Val Ala Ala Leu Phe
            370                 375                 380
Phe Phe Asp Ile Asp Leu Leu Leu Gln Arg Gly Pro Gln Tyr Ser Glu
385                 390                 395                 400
His Pro Thr Phe Thr Ser Gln Tyr Arg Ile Gln Gly Lys Leu Glu Tyr
            405                 410                 415
Arg His Thr Trp Asp Arg His Asp Glu Gly Ala Ala Gln Gly Asp Asp
            420                 425                 430
Asp Val Trp Thr Gly Ser Asp Ser Asp Glu Leu Val Thr Thr
            435                 440                 445
Glu Arg Lys Thr Pro Arg Val Thr Gly Gly Ala Met Ala Gly Ala
            450                 455                 460
Ser Thr Ser Ala Gly Arg Lys Arg Lys Ser Ala Ser Ser Ala Thr Ala
465                 470                 475                 480
Cys Thr Ser Gly Val Met Thr Arg Gly Arg Leu Lys Ala Glu Ser Thr
                485                 490                 495
Val Ala Pro Glu Glu Asp Thr Asp Glu Asp Ser Asp Asn Glu Ile His
            500                 505                 510
```

```
Asn Pro Ala Val Phe Thr Trp Pro Trp Gln Ala Gly Ile Leu Ala
        515                 520                 525

Arg Asn Leu Val Pro Met Val Ala Thr Val Gln Gly Gln Asn Leu Lys
    530                 535                 540

Tyr Gln Glu Phe Phe Trp Asp Ala Asn Asp Ile Tyr Arg Ile Phe Ala
545                 550                 555                 560

Glu Leu Glu Gly Val Trp Gln Pro Ala Ala Gln Pro Lys Arg Arg Arg
                565                 570                 575

His Arg Gln Asp Ala Leu Pro Gly Pro Cys Ile Ala Ser Thr Pro Lys
            580                 585                 590

Lys His Arg Gly Gly Ser Gln Ser Lys Met Leu Ser Gly Val Gly Gly
        595                 600                 605

Phe Val Leu Gly Leu Leu Phe Leu Gly Ala Gly Leu Phe Ile Tyr Phe
    610                 615                 620

Arg Asn Gln Lys Gly His Ser Gly Leu Gln Pro Arg Gly Phe Leu Ser
625                 630                 635                 640

<210> SEQ ID NO 15
<211> LENGTH: 66
<212> TYPE: PRT
<213> ORGANISM: Homo sapiens

<400> SEQUENCE: 15

Pro Ser Ser Gln Pro Thr Ile Pro Ile Val Gly Ile Ile Ala Gly Leu
1               5                   10                  15

Val Leu Phe Gly Ala Val Ile Thr Gly Ala Val Val Ala Ala Val Met
            20                  25                  30

Trp Arg Arg Lys Ser Ser Asp Arg Lys Gly Gly Ser Tyr Ser Gln Ala
        35                  40                  45

Ala Ser Ser Asp Ser Ala Gln Gly Ser Asp Val Ser Leu Thr Ala Cys
    50                  55                  60

Lys Val
65

<210> SEQ ID NO 16
<211> LENGTH: 24
<212> TYPE: PRT
<213> ORGANISM: Homo sapiens

<400> SEQUENCE: 16

Gly Ser Tyr Ser Gln Ala Ala Ser Ser Asp Ser Ala Gln Gly Ser Asp
1               5                   10                  15

Val Ser Leu Thr Ala Cys Lys Val
            20

<210> SEQ ID NO 17
<211> LENGTH: 63
<212> TYPE: PRT
<213> ORGANISM: Homo sapiens

<400> SEQUENCE: 17

Pro Ser Ser Gln Ser Thr Val Pro Ile Val Gly Ile Ala Gly Leu
1               5                   10                  15

Ala Val Leu Ala Val Val Ile Gly Ala Val Ala Ala Val Met
            20                  25                  30

Cys Arg Arg Lys Ser Gly Gly Lys Gly Gly Ser Tyr Ser Gln Ala
        35                  40                  45

Ala Cys Ser Asp Ser Ala Gln Gly Ser Asp Val Ser Leu Thr Ala
    50                  55                  60
```

```
-continued

<210> SEQ ID NO 18
<211> LENGTH: 21
<212> TYPE: PRT
<213> ORGANISM: Homo sapiens

<400> SEQUENCE: 18

Gly Ser Tyr Ser Gln Ala Ala Cys Ser Asp Ser Ala Gln Gly Ser Asp
1               5                   10                  15

Val Ser Leu Thr Ala
            20

<210> SEQ ID NO 19
<211> LENGTH: 67
<212> TYPE: PRT
<213> ORGANISM: Homo sapiens

<400> SEQUENCE: 19

Pro Ser Ser Gln Pro Thr Ile Pro Ile Val Gly Ile Val Ala Gly Leu
1               5                   10                  15

Ala Val Leu Ala Val Leu Ala Val Leu Gly Ala Met Val Ala Val Val
            20                  25                  30

Met Cys Arg Arg Lys Ser Ser Gly Gly Lys Gly Gly Ser Cys Ser Gln
        35                  40                  45

Ala Ala Ser Ser Asn Ser Ala Gln Gly Ser Asp Glu Ser Leu Ile Ala
    50                  55                  60

Cys Lys Ala
65

<210> SEQ ID NO 20
<211> LENGTH: 14
<212> TYPE: PRT
<213> ORGANISM: Homo sapiens

<400> SEQUENCE: 20

Ser Ala Gln Gly Ser Asp Glu Ser Leu Ile Ala Cys Lys Ala
1               5                   10

<210> SEQ ID NO 21
<211> LENGTH: 62
<212> TYPE: PRT
<213> ORGANISM: Homo sapiens

<400> SEQUENCE: 21

Pro Ala Ser Gln Pro Thr Ile Pro Ile Val Gly Ile Ile Ala Gly Leu
1               5                   10                  15

Val Leu Leu Gly Ser Val Val Ser Gly Ala Val Val Ala Ala Val Ile
            20                  25                  30

Trp Arg Lys Lys Ser Ser Gly Gly Lys Gly Gly Ser Tyr Ser Lys Ala
        35                  40                  45

Glu Trp Ser Asp Ser Ala Gln Gly Ser Glu Ser His Ser Leu
    50                  55                  60

<210> SEQ ID NO 22
<211> LENGTH: 20
<212> TYPE: PRT
<213> ORGANISM: Homo sapiens

<400> SEQUENCE: 22

Gly Ser Tyr Ser Lys Ala Glu Trp Ser Asp Ser Ala Gln Gly Ser Glu
1               5                   10                  15
```

```
Ser His Ser Leu
            20

<210> SEQ ID NO 23
<211> LENGTH: 66
<212> TYPE: PRT
<213> ORGANISM: Homo sapiens

<400> SEQUENCE: 23

Gln Ser Pro Gln Pro Thr Ile Pro Ile Val Gly Ile Val Ala Gly Leu
1               5                   10                  15

Val Val Leu Gly Ala Val Val Thr Gly Ala Val Val Ala Ala Val Met
            20                  25                  30

Trp Arg Lys Lys Ser Ser Asp Arg Asn Arg Gly Ser Tyr Ser Gln Ala
        35                  40                  45

Ala Val Thr Asp Ser Ala Gln Gly Ser Gly Val Ser Leu Thr Ala Asn
    50                  55                  60

Lys Val
65

<210> SEQ ID NO 24
<211> LENGTH: 27
<212> TYPE: PRT
<213> ORGANISM: Homo sapiens

<400> SEQUENCE: 24

Arg Asn Arg Gly Ser Tyr Ser Gln Ala Ala Val Thr Asp Ser Ala Gln
1               5                   10                  15

Gly Ser Gly Val Ser Leu Thr Ala Asn Lys Val
            20                  25

<210> SEQ ID NO 25
<211> LENGTH: 37
<212> TYPE: PRT
<213> ORGANISM: Homo sapiens

<400> SEQUENCE: 25

Val Val Cys Ala Leu Gly Leu Thr Val Gly Leu Val Gly Ile Ile Ile
1               5                   10                  15

Gly Thr Ile Phe Ile Ile Lys Gly Leu Arg Lys Ser Asn Ala Ala Glu
            20                  25                  30

Arg Arg Gly Pro Leu
        35

<210> SEQ ID NO 26
<211> LENGTH: 12
<212> TYPE: PRT
<213> ORGANISM: Homo sapiens

<400> SEQUENCE: 26

Arg Lys Ser Asn Ala Ala Glu Arg Arg Gly Pro Leu
1               5                   10

<210> SEQ ID NO 27
<211> LENGTH: 38
<212> TYPE: PRT
<213> ORGANISM: Homo sapiens

<400> SEQUENCE: 27

Met Leu Ser Gly Val Gly Gly Phe Val Leu Gly Leu Phe Leu
1               5                   10                  15

Gly Leu Phe Ile Tyr Phe Arg Asn Gln Lys Gly His Ser Gly Leu Gln
```

```
                    20                  25                  30

Pro Arg Gly Phe Leu Ser
        35

<210> SEQ ID NO 28
<211> LENGTH: 12
<212> TYPE: PRT
<213> ORGANISM: Homo sapiens

<400> SEQUENCE: 28

Gly His Ser Gly Leu Gln Pro Arg Gly Phe Leu Ser
1               5                   10

<210> SEQ ID NO 29
<211> LENGTH: 37
<212> TYPE: PRT
<213> ORGANISM: Homo sapiens

<400> SEQUENCE: 29

Val Val Cys Ala Leu Gly Leu Ser Val Gly Leu Met Gly Ile Val Val
1               5                   10                  15

Gly Thr Val Phe Ile Ile Gln Gly Leu Arg Ser Val Gly Ala Ser Arg
            20                  25                  30

His Gln Gly Pro Leu
        35

<210> SEQ ID NO 30
<211> LENGTH: 10
<212> TYPE: PRT
<213> ORGANISM: Homo sapiens

<400> SEQUENCE: 30

Val Gly Ala Ser Arg His Gln Gly Pro Leu
1               5                   10

<210> SEQ ID NO 31
<211> LENGTH: 31
<212> TYPE: PRT
<213> ORGANISM: Homo sapiens

<400> SEQUENCE: 31

Met Leu Ser Gly Ile Gly Gly Phe Val Leu Gly Leu Ile Phe Leu Gly
1               5                   10                  15

Leu Gly Leu Ile Ile His His Arg Ser Gln Lys Gly Leu Leu His
            20                  25                  30

<210> SEQ ID NO 32
<211> LENGTH: 8
<212> TYPE: PRT
<213> ORGANISM: Homo sapiens

<400> SEQUENCE: 32

Arg Ser Gln Lys Gly Leu Leu His
1               5

<210> SEQ ID NO 33
<211> LENGTH: 37
<212> TYPE: PRT
<213> ORGANISM: Homo sapiens

<400> SEQUENCE: 33

Val Leu Cys Ala Leu Gly Leu Val Leu Gly Leu Val Gly Ile Ile Val
1               5                   10                  15
```

Gly Thr Val Leu Ile Ile Lys Ser Leu Arg Ser Gly His Asp Pro Arg
            20                  25                  30

Ala Gln Gly Thr Leu
            35

<210> SEQ ID NO 34
<211> LENGTH: 12
<212> TYPE: PRT
<213> ORGANISM: Homo sapiens

<400> SEQUENCE: 34

Arg Ser Gly His Asp Pro Arg Ala Gln Gly Thr Leu
1               5                   10

<210> SEQ ID NO 35
<211> LENGTH: 33
<212> TYPE: PRT
<213> ORGANISM: Homo sapiens

<400> SEQUENCE: 35

Thr Leu Thr Gly Ala Gly Gly Phe Val Leu Gly Leu Ile Ile Cys Gly
1               5                   10                  15

Val Gly Ile Phe Met His Arg Arg Ser Lys Lys Val Gln Arg Gly Ser
            20                  25                  30

Ala

<210> SEQ ID NO 36
<211> LENGTH: 9
<212> TYPE: PRT
<213> ORGANISM: Homo sapiens

<400> SEQUENCE: 36

Ser Lys Lys Val Gln Arg Gly Ser Ala
1               5

<210> SEQ ID NO 37
<211> LENGTH: 26
<212> TYPE: PRT
<213> ORGANISM: Homo sapiens

<400> SEQUENCE: 37

Phe Ile Ile Leu Ala Val Ile Val Pro Leu Leu Leu Ile Gly Leu
1               5                   10                  15

Ala Leu Trp Phe Arg Lys Arg Cys Phe Cys
            20                  25

<210> SEQ ID NO 38
<211> LENGTH: 6
<212> TYPE: PRT
<213> ORGANISM: Homo sapiens

<400> SEQUENCE: 38

Arg Lys Arg Cys Phe Cys
1               5

<210> SEQ ID NO 39
<211> LENGTH: 30
<212> TYPE: PRT
<213> ORGANISM: Homo sapiens

<400> SEQUENCE: 39

Ile Val Leu Ala Ile Ile Val Pro Ser Leu Leu Leu Leu Cys Leu
1               5                   10                  15

```
Ala Leu Trp Tyr Met Arg Arg Ser Tyr Gln Asn Ile Pro
            20                  25                  30

<210> SEQ ID NO 40
<211> LENGTH: 9
<212> TYPE: PRT
<213> ORGANISM: Homo sapiens

<400> SEQUENCE: 40

Arg Arg Arg Ser Tyr Gln Asn Ile Pro
1               5

<210> SEQ ID NO 41
<211> LENGTH: 30
<212> TYPE: PRT
<213> ORGANISM: Homo sapiens

<400> SEQUENCE: 41

Trp Ile Ala Leu Val Val Ile Val Pro Leu Val Ile Leu Ile Val Leu
1               5                   10                  15

Val Leu Trp Phe Lys Lys His Cys Ser Tyr Gln Asp Ile Leu
            20                  25                  30

<210> SEQ ID NO 42
<211> LENGTH: 10
<212> TYPE: PRT
<213> ORGANISM: Homo sapiens

<400> SEQUENCE: 42

Lys Lys His Cys Ser Tyr Gln Asp Ile Leu
1               5                   10

<210> SEQ ID NO 43
<211> LENGTH: 250
<212> TYPE: PRT
<213> ORGANISM: Homo sapiens

<400> SEQUENCE: 43

Met Ala Ala Gly Thr Ser Ser Tyr Trp Glu Asp Leu Arg Lys Gln Ala
1               5                   10                  15

Arg Gln Leu Glu Asn Glu Leu Asp Leu Lys Leu Val Ser Phe Ser Lys
            20                  25                  30

Leu Cys Thr Ser Tyr Ser His Ser Ser Thr Arg Asp Gly Arg Arg Asp
            35                  40                  45

Arg Tyr Ser Ser Asp Thr Thr Pro Leu Leu Asn Gly Ser Ser Gln Asp
        50                  55                  60

Arg Met Phe Glu Thr Met Ala Ile Glu Ile Glu Gln Leu Leu Ala Arg
65                  70                  75                  80

Leu Thr Gly Val Asn Asp Lys Met Ala Glu Tyr Thr Asn Ser Ala Gly
                85                  90                  95

Val Pro Ser Leu Asn Ala Ala Leu Met His Thr Leu Gln Arg His Arg
            100                 105                 110

Asp Ile Leu Gln Asp Tyr Thr His Glu Phe His Lys Thr Lys Ala Asn
            115                 120                 125

Phe Met Ala Ile Arg Glu Arg Glu Asn Leu Met Gly Ser Val Arg Lys
        130                 135                 140

Asp Ile Glu Ser Tyr Lys Ser Gly Ser Gly Val Asn Asn Arg Arg Thr
145                 150                 155                 160

Glu Leu Phe Leu Lys Glu His Asp His Leu Arg Asn Ser Asp Arg Leu
                165                 170                 175
```

```
Ile Glu Glu Thr Ile Ser Ile Ala Met Ala Thr Lys Glu Asn Met Thr
                180                 185                 190

Ser Gln Arg Gly Met Leu Lys Ser Ile His Ser Lys Met Asn Thr Leu
            195                 200                 205

Ala Asn Arg Phe Pro Ala Val Asn Ser Leu Ile Gln Arg Ile Asn Leu
        210                 215                 220

Arg Lys Arg Arg Asp Ser Leu Ile Leu Gly Val Ile Gly Ile Cys
225                 230                 235                 240

Thr Ile Leu Leu Leu Leu Tyr Ala Phe His
                245                 250

<210> SEQ ID NO 44
<211> LENGTH: 128
<212> TYPE: PRT
<213> ORGANISM: Homo sapiens

<400> SEQUENCE: 44

Met Gly Ala Ser Leu Thr Ser Pro Gly Thr Gln Glu Lys Leu Ile Arg
1               5                   10                  15

Asp Phe Asp Glu Lys Gln Gln Glu Ala Asn Lys Met Leu Thr Gln Met
                20                  25                  30

Glu Glu Glu Leu His Tyr Ala Pro Val Ser Phe His Asn Pro Met Met
            35                  40                  45

Ser Lys Leu Gln Asp Tyr Gln Lys Asp Leu Ala Gln Phe His Leu Glu
        50                  55                  60

Ala Arg Thr Met Pro Gly Asp Arg Gly Asp Met Lys Tyr Gly Thr Tyr
65                  70                  75                  80

Ala Val Glu Asn Glu His Met Asn Arg Leu Gln Ser Gln Arg Ala Met
                85                  90                  95

Leu Leu Gln Gly Thr Lys Ser Leu Gly Arg Ala Thr Gln Glu Thr Asp
            100                 105                 110

Gln Ile Gly Ser Glu Ile Ser Glu Glu Leu Gly Asn Gln Arg Asp Gln
        115                 120                 125

<210> SEQ ID NO 45
<211> LENGTH: 212
<212> TYPE: PRT
<213> ORGANISM: Homo sapiens

<400> SEQUENCE: 45

Met Asp Pro Leu Phe Gln Gln Thr His Lys Gln Val His Glu Ile Gln
1               5                   10                  15

Ser Cys Met Gly Arg Leu Glu Thr Ala Asp Lys Gln Ser Val His Ile
                20                  25                  30

Val Glu Asn Glu Ile Gln Ala Ser Ile Asp Gln Ile Phe Ser Arg Leu
            35                  40                  45

Glu Arg Leu Glu Ile Leu Ser Ser Lys Glu Pro Pro Asn Lys Arg Gln
        50                  55                  60

Asn Ala Arg Leu Arg Val Asp Gln Leu Lys Tyr Asp Val Gln His Leu
65                  70                  75                  80

Gln Thr Ala Leu Arg Asn Phe Gln His Arg Arg His Ala Arg Glu Gln
                85                  90                  95

Gln Glu Arg Gln Arg Glu Glu Leu Leu Ser Arg Thr Phe Thr Thr Asn
            100                 105                 110

Asp Ser Asp Thr Thr Ile Pro Met Asp Glu Ser Leu Gln Phe Asn Ser
        115                 120                 125

Ser Leu Gln Lys Val His Asn Gly Met Asp Asp Leu Ile Leu Asp Gly
```

```
            130                 135                 140
His Asn Ile Leu Asp Gly Leu Arg Thr Gln Arg Leu Thr Leu Lys Gly
145                 150                 155                 160

Thr Gln Lys Lys Ile Leu Asp Ile Ala Asn Met Leu Gly Leu Ser Asn
                165                 170                 175

Thr Val Met Arg Leu Ile Glu Lys Arg Ala Phe Gln Asp Lys Tyr Phe
            180                 185                 190

Met Ile Gly Gly Met Leu Leu Thr Cys Val Val Met Phe Leu Val Val
            195                 200                 205

Gln Tyr Leu Thr
    210

<210> SEQ ID NO 46
<211> LENGTH: 172
<212> TYPE: PRT
<213> ORGANISM: Homo sapiens

<400> SEQUENCE: 46

Met Ser Val Pro Gly Pro Ser Pro Asp Gly Ala Leu Thr Arg Pro
1               5                   10                  15

Pro Tyr Cys Leu Glu Ala Gly Glu Pro Thr Pro Gly Leu Ser Asp Thr
                20                  25                  30

Ser Pro Asp Glu Gly Leu Ile Glu Asp Leu Thr Ile Glu Asp Lys Ala
            35                  40                  45

Val Glu Gln Leu Ala Glu Gly Leu Leu Ser His Tyr Leu Pro Asp Leu
        50                  55                  60

Gln Arg Ser Lys Gln Ala Leu Gln Glu Leu Thr Gln Asn Gln Val Val
65                  70                  75                  80

Leu Leu Asp Thr Leu Gln Glu Ile Ser Lys Phe Lys Glu Cys His
                85                  90                  95

Ser Met Leu Asp Ile Asn Ala Leu Phe Ala Glu Ala Lys His Tyr His
                100                 105                 110

Ala Lys Leu Val Asn Ile Arg Lys Glu Met Leu Met Leu His Glu Lys
            115                 120                 125

Thr Ser Lys Leu Lys Lys Arg Ala Leu Lys Leu Gln Gln Lys Arg Gln
130                 135                 140

Lys Glu Glu Leu Glu Arg Glu Gln Gln Arg Glu Lys Glu Phe Glu Arg
145                 150                 155                 160

Glu Lys Gln Leu Thr Ala Arg Pro Ala Lys Arg Met
                165                 170

<210> SEQ ID NO 47
<211> LENGTH: 301
<212> TYPE: PRT
<213> ORGANISM: Homo sapiens

<400> SEQUENCE: 47

Met Ser Cys Arg Asp Arg Thr Gln Glu Phe Leu Ser Ala Cys Lys Ser
1               5                   10                  15

Leu Gln Thr Arg Gln Asn Gly Ile Gln Thr Asn Lys Pro Ala Leu Arg
                20                  25                  30

Ala Val Arg Gln Arg Ser Glu Phe Thr Leu Met Ala Lys Arg Ile Gly
            35                  40                  45

Lys Asp Leu Ser Asn Thr Phe Ala Lys Leu Glu Lys Leu Thr Ile Leu
        50                  55                  60

Ala Lys Arg Lys Ser Leu Phe Asp Asp Lys Ala Val Glu Ile Glu Glu
65                  70                  75                  80
```

```
Leu Thr Tyr Ile Ile Lys Gln Asp Ile Asn Ser Leu Asn Lys Gln Ile
                85                  90                  95

Ala Gln Leu Gln Asp Phe Val Arg Ala Lys Gly Ser Gln Ser Gly Arg
            100                 105                 110

His Leu Gln Thr His Ser Asn Thr Ile Val Val Ser Leu Gln Ser Lys
            115                 120                 125

Leu Ala Ser Met Ser Asn Asp Phe Lys Ser Val Leu Glu Val Arg Thr
    130                 135                 140

Glu Asn Leu Lys Gln Gln Arg Ser Arg Arg Glu Gln Phe Ser Arg Ala
145                 150                 155                 160

Pro Val Ser Ala Leu Pro Leu Ala Pro Asn His Leu Gly Gly Gly Ala
                165                 170                 175

Val Val Leu Gly Ala Glu Ser His Ala Ser Lys Asp Val Ala Ile Asp
            180                 185                 190

Met Met Asp Ser Arg Thr Ser Gln Gln Leu Gln Leu Ile Asp Glu Gln
            195                 200                 205

Asp Ser Tyr Ile Gln Ser Arg Ala Asp Thr Met Gln Asn Ile Glu Ser
    210                 215                 220

Thr Ile Val Glu Leu Gly Ser Ile Phe Gln Gln Leu Ala His Met Val
225                 230                 235                 240

Lys Glu Gln Glu Glu Thr Ile Gln Arg Ile Asp Glu Asn Val Leu Gly
                245                 250                 255

Ala Gln Leu Asp Val Glu Ala Ala His Ser Glu Ile Leu Lys Tyr Phe
            260                 265                 270

Gln Ser Val Thr Ser Asn Arg Trp Leu Met Val Lys Ile Phe Leu Ile
            275                 280                 285

Leu Ile Val Phe Phe Ile Ile Phe Val Val Phe Leu Ala
    290                 295                 300

<210> SEQ ID NO 48
<211> LENGTH: 255
<212> TYPE: PRT
<213> ORGANISM: Homo sapiens

<400> SEQUENCE: 48

Met Ser Met Glu Asp Pro Phe Phe Val Val Lys Gly Glu Val Gln Lys
1               5                   10                  15

Ala Val Asn Thr Ala Gln Gly Leu Phe Gln Arg Trp Thr Glu Leu Leu
            20                  25                  30

Gln Asp Pro Ser Thr Ala Thr Arg Glu Glu Ile Asp Trp Thr Thr Asn
        35                  40                  45

Glu Leu Arg Asn Asn Leu Arg Ser Ile Glu Trp Asp Leu Glu Asp Leu
    50                  55                  60

Asp Glu Thr Ile Ser Ile Val Glu Ala Asn Pro Arg Lys Phe Asn Leu
65                  70                  75                  80

Asp Ala Thr Glu Leu Ser Ile Arg Lys Ala Phe Ile Thr Ser Thr Arg
                85                  90                  95

Gln Val Val Arg Asp Met Lys Asp Gln Met Ser Thr Ser Ser Val Gln
            100                 105                 110

Ala Leu Ala Glu Arg Lys Asn Arg Gln Ala Leu Leu Gly Asp Ser Gly
            115                 120                 125

Ser Gln Asn Trp Ser Thr Gly Thr Thr Asp Lys Tyr Gly Arg Leu Asp
    130                 135                 140

Arg Glu Leu Gln Arg Ala Asn Ser His Phe Ile Glu Glu Gln Gln Ala
145                 150                 155                 160
```

```
Gln Gln Gln Leu Ile Val Glu Gln Asp Glu Gln Leu Glu Leu Val
                165                 170                 175

Ser Gly Ser Ile Gly Val Leu Lys Asn Met Ser Gln Arg Ile Gly Gly
            180                 185                 190

Glu Leu Glu Glu Gln Ala Val Met Leu Glu Asp Phe Ser His Glu Leu
            195                 200                 205

Glu Ser Thr Gln Ser Arg Leu Asp Asn Val Met Lys Lys Leu Ala Lys
210                 215                 220

Val Ser His Met Thr Ser Asp Arg Arg Gln Trp Cys Ala Ile Ala Ile
225                 230                 235                 240

Leu Phe Ala Val Leu Leu Val Val Leu Ile Leu Phe Leu Val Leu
                245                 250                 255

<210> SEQ ID NO 49
<211> LENGTH: 261
<212> TYPE: PRT
<213> ORGANISM: Homo sapiens

<400> SEQUENCE: 49

Met Ser Tyr Thr Pro Gly Val Gly Gly Asp Pro Ala Gln Leu Ala Gln
1               5                   10                  15

Arg Ile Ser Ser Asn Ile Gln Lys Ile Thr Gln Cys Ser Val Glu Ile
            20                  25                  30

Gln Arg Thr Leu Asn Gln Leu Gly Thr Pro Gln Asp Ser Pro Glu Leu
        35                  40                  45

Arg Gln Gln Leu Gln Gln Lys Gln Gln Tyr Thr Asn Gln Leu Ala Lys
    50                  55                  60

Glu Thr Asp Lys Tyr Ile Lys Glu Phe Gly Ser Leu Pro Thr Thr Pro
65                  70                  75                  80

Ser Glu Gln Arg Gln Arg Lys Ile Gln Lys Asp Arg Leu Val Ala Glu
                85                  90                  95

Phe Thr Thr Ser Leu Thr Asn Phe Gln Lys Val Gln Arg Gln Ala Ala
            100                 105                 110

Glu Arg Glu Lys Glu Phe Val Ala Arg Val Arg Ala Ser Ser Arg Val
        115                 120                 125

Ser Gly Ser Phe Pro Glu Asp Ser Ser Lys Glu Arg Asn Leu Val Ser
    130                 135                 140

Trp Glu Ser Gln Thr Gln Pro Gln Val Gln Val Gln Asp Glu Glu Ile
145                 150                 155                 160

Thr Glu Asp Asp Leu Arg Leu Ile His Glu Arg Glu Ser Ser Ile Arg
                165                 170                 175

Gln Leu Glu Ala Asp Ile Met Asp Ile Asn Glu Ile Phe Lys Asp Leu
            180                 185                 190

Gly Met Met Ile His Glu Gln Gly Asp Val Ile Asp Ser Ile Glu Ala
        195                 200                 205

Asn Val Glu Asn Ala Glu Val His Val Gln Gln Ala Asn Gln Gln Leu
    210                 215                 220

Ser Arg Ala Ala Asp Tyr Gln Arg Lys Ser Arg Lys Thr Leu Cys Ile
225                 230                 235                 240

Ile Ile Leu Ile Leu Val Ile Gly Val Ala Ile Ile Ser Leu Ile Ile
                245                 250                 255

Trp Gly Leu Asn His
            260

<210> SEQ ID NO 50
```

```
<211> LENGTH: 236
<212> TYPE: PRT
<213> ORGANISM: Homo sapiens

<400> SEQUENCE: 50

Met Ala Pro Asp Pro Trp Phe Ser Thr Tyr Asp Ser Thr Cys Gln Ile
1               5                   10                  15

Ala Gln Glu Ile Ala Glu Lys Ile Gln Gln Arg Asn Gln Tyr Glu Arg
            20                  25                  30

Lys Gly Glu Lys Ala Pro Lys Leu Thr Val Thr Ile Arg Ala Leu Leu
        35                  40                  45

Gln Asn Leu Lys Glu Lys Ile Ala Leu Leu Lys Asp Leu Leu Leu Arg
50                  55                  60

Ala Val Ser Thr His Gln Ile Thr Gln Leu Glu Gly Asp Arg Arg Gln
65                  70                  75                  80

Asn Leu Leu Asp Asp Leu Val Thr Arg Glu Arg Leu Leu Leu Ala Ser
                85                  90                  95

Phe Lys Asn Glu Gly Ala Glu Pro Asp Leu Ile Arg Ser Ser Leu Met
            100                 105                 110

Ser Glu Glu Ala Lys Arg Gly Ala Pro Asn Pro Trp Leu Phe Glu Glu
        115                 120                 125

Pro Glu Glu Thr Arg Gly Leu Gly Phe Asp Glu Ile Arg Gln Gln Gln
130                 135                 140

Gln Lys Ile Ile Gln Glu Gln Asp Ala Gly Leu Asp Ala Leu Ser Ser
145                 150                 155                 160

Ile Ile Ser Arg Gln Lys Gln Met Gly Gln Ile Gly Asn Glu Leu
                165                 170                 175

Asp Glu Gln Asn Glu Ile Ile Asp Asp Leu Ala Asn Leu Val Glu Asn
            180                 185                 190

Thr Asp Glu Lys Leu Arg Asn Glu Thr Arg Arg Val Asn Met Val Asp
        195                 200                 205

Arg Lys Ser Ala Ser Cys Gly Met Ile Met Val Ile Leu Leu Leu Leu
210                 215                 220

Val Ala Ile Val Val Ala Val Trp Pro Thr Asn
225                 230                 235

<210> SEQ ID NO 51
<211> LENGTH: 200
<212> TYPE: PRT
<213> ORGANISM: Homo sapiens

<400> SEQUENCE: 51

Met Ser Leu Glu Asp Pro Phe Phe Val Val Arg Gly Glu Val Gln Lys
1               5                   10                  15

Ala Val Asn Thr Ala Arg Gly Leu Tyr Gln Arg Trp Cys Glu Leu Leu
            20                  25                  30

Gln Glu Ser Ala Ala Val Gly Arg Glu Glu Leu Asp Trp Thr Thr Asn
        35                  40                  45

Glu Leu Arg Asn Gly Leu Arg Ser Ile Glu Trp Asp Leu Glu Asp Leu
50                  55                  60

Glu Glu Thr Ile Gly Ile Val Glu Ala Asn Pro Gly Lys Pro Ala Ala
65                  70                  75                  80

Gln Lys Ser Pro Ser Asp Leu Leu Asp Ala Ser Ala Val Ser Ala Thr
                85                  90                  95

Ser Arg Tyr Ile Glu Glu Gln Gln Ala Thr Gln Gln Leu Ile Met Asp
            100                 105                 110
```

```
Glu Gln Asp Gln Gln Leu Glu Met Val Ser Gly Ser Ile Gln Val Leu
            115                 120                 125

Lys His Met Ser Gly Arg Val Gly Glu Glu Leu Asp Glu Gln Gly Ile
    130                 135                 140

Met Leu Asp Ala Phe Ala Gln Glu Met Asp His Thr Gln Ser Arg Met
145                 150                 155                 160

Asp Gly Val Leu Arg Lys Leu Ala Lys Val Ser His Met Thr Ser Asp
                165                 170                 175

Arg Arg Gln Trp Cys Ala Ile Ala Val Leu Val Gly Val Leu Leu Leu
                180                 185                 190

Val Leu Ile Leu Leu Phe Ser Leu
            195                 200

<210> SEQ ID NO 52
<211> LENGTH: 249
<212> TYPE: PRT
<213> ORGANISM: Homo sapiens

<400> SEQUENCE: 52

Met Ser Leu Glu Asp Pro Phe Phe Val Val Arg Gly Glu Val Gln Lys
1               5                   10                  15

Ala Val Asn Thr Ala Arg Gly Leu Tyr Gln Arg Trp Cys Glu Leu Leu
            20                  25                  30

Gln Glu Ser Ala Ala Val Gly Arg Glu Glu Leu Asp Trp Thr Thr Asn
        35                  40                  45

Glu Leu Arg Asn Gly Leu Arg Ser Ile Glu Trp Asp Leu Glu Asp Leu
    50                  55                  60

Glu Glu Thr Ile Gly Ile Val Glu Ala Asn Pro Gly Lys Phe Lys Leu
65                  70                  75                  80

Pro Ala Gly Asp Leu Gln Glu Arg Lys Val Phe Val Glu Arg Met Arg
                85                  90                  95

Glu Ala Val Gln Glu Met Lys Asp His Met Val Ser Pro Thr Ala Val
            100                 105                 110

Ala Phe Leu Glu Arg Asn Asn Arg Glu Ile Leu Ala Gly Lys Pro Ala
        115                 120                 125

Ala Gln Lys Ser Pro Ser Asp Leu Leu Asp Ala Ser Ala Val Ser Ala
    130                 135                 140

Thr Ser Arg Tyr Ile Glu Gln Gln Ala Thr Gln Gln Leu Ile Met
145                 150                 155                 160

Asp Glu Gln Asp Gln Gln Leu Glu Met Val Ser Gly Ser Ile Gln Val
                165                 170                 175

Leu Lys His Met Ser Gly Arg Val Gly Glu Glu Leu Asp Glu Gln Gly
                180                 185                 190

Ile Met Leu Asp Ala Phe Ala Gln Glu Met Asp His Thr Gln Ser Arg
            195                 200                 205

Met Asp Gly Val Leu Arg Lys Leu Ala Lys Val Ser His Met Thr Ser
        210                 215                 220

Asp Arg Arg Gln Trp Cys Ala Ile Ala Val Leu Val Gly Val Leu Leu
225                 230                 235                 240

Leu Val Leu Ile Leu Leu Phe Ser Leu
                245

<210> SEQ ID NO 53
<211> LENGTH: 287
<212> TYPE: PRT
<213> ORGANISM: Homo sapiens
```

<400> SEQUENCE: 53

```
Met Lys Asp Arg Leu Ala Glu Leu Leu Asp Leu Ser Lys Gln Tyr Asp
1               5                   10                  15

Gln Gln Phe Pro Asp Gly Asp Glu Phe Asp Ser Pro His Glu Asp
            20                  25                  30

Ile Val Phe Glu Thr Asp His Ile Leu Glu Ser Leu Tyr Arg Asp Ile
        35                  40                  45

Arg Asp Ile Gln Asp Glu Asn Gln Leu Leu Val Ala Asp Val Lys Arg
50                  55                  60

Leu Gly Lys Gln Asn Ala Arg Phe Leu Thr Ser Met Arg Arg Leu Ser
65                  70                  75                  80

Ser Ile Lys Arg Asp Thr Asn Ser Ile Ala Lys Ala Phe Arg Ala Arg
                85                  90                  95

Gly Glu Val Ile His Cys Lys Leu Arg Ala Met Lys Glu Leu Ser Glu
            100                 105                 110

Ala Ala Glu Ala Gln His Gly Pro His Ser Ala Val Ala Arg Ile Ser
        115                 120                 125

Arg Ala Gln Tyr Asn Ala Leu Thr Leu Thr Phe Gln Arg Ala Met His
130                 135                 140

Asp Tyr Asn Gln Ala Glu Met Lys Gln Arg Asp Asn Cys Lys Ile Arg
145                 150                 155                 160

Ile Gln Arg Gln Leu Glu Ile Met Gly Lys Glu Val Ser Gly Asp Gln
                165                 170                 175

Ile Glu Asp Met Phe Glu Gln Gly Lys Trp Asp Val Phe Ser Glu Asn
            180                 185                 190

Leu Leu Ala Asp Val Lys Gly Arg Gly Pro Pro Thr Thr Arg Ser Arg
        195                 200                 205

Ala Ala Thr Ala Asn Cys Cys Ala Trp Arg Ala Ala Ile Arg Asp Val
210                 215                 220

His Glu Leu Phe Leu Gln Met Ala Val Leu Val Glu Lys Gln Ala Asp
225                 230                 235                 240

Thr Leu Asn Val Ile Glu Leu Asn Val Gln Lys Thr Val Asp Tyr Thr
                245                 250                 255

Gly Gln Ala Lys Ala Gln Val Arg Lys Ala Val Gln Tyr Glu Glu Lys
            260                 265                 270

Asn Pro Cys Arg Thr Leu Cys Cys Phe Cys Cys Pro Cys Leu Lys
        275                 280                 285
```

<210> SEQ ID NO 54
<211> LENGTH: 276
<212> TYPE: PRT
<213> ORGANISM: Homo sapiens

<400> SEQUENCE: 54

```
Met Ser Tyr Gly Pro Leu Asp Met Tyr Arg Asn Pro Gly Pro Ser Gly
1               5                   10                  15

Pro Gln Leu Arg Asp Phe Ser Ser Ile Ile Gln Thr Cys Ser Gly Asn
            20                  25                  30

Ile Gln Arg Ile Ser Gln Ala Thr Ala Gln Ile Lys Asn Leu Met Ser
        35                  40                  45

Gln Leu Gly Thr Lys Gln Asp Ser Ser Lys Leu Gln Glu Asn Leu Gln
50                  55                  60

Gln Leu Gln His Ser Thr Asn Gln Leu Ala Lys Glu Thr Asn Glu Leu
65                  70                  75                  80

Leu Lys Glu Leu Gly Ser Leu Pro Leu Pro Leu Ser Thr Ser Glu Gln
```

```
                    85                  90                  95
Arg Gln Gln Arg Leu Gln Lys Glu Arg Leu Met Asn Asp Phe Ser Ala
            100                 105                 110

Ala Leu Asn Asn Phe Gln Ala Val Gln Arg Arg Val Ser Glu Lys Glu
        115                 120                 125

Lys Glu Ser Ile Ala Arg Ala Arg Ala Gly Ser Arg Leu Ser Ala Glu
    130                 135                 140

Glu Arg Gln Arg Glu Glu Gln Leu Val Ser Phe Asp Ser His Glu Glu
145                 150                 155                 160

Trp Asn Gln Met Gln Ser Gln Glu Asp Glu Val Ala Ile Thr Glu Gln
                165                 170                 175

Asp Leu Glu Leu Ile Lys Glu Arg Glu Thr Ala Ile Arg Gln Leu Glu
            180                 185                 190

Ala Asp Ile Leu Asp Val Asn Gln Ile Phe Lys Asp Leu Ala Met Met
        195                 200                 205

Ile His Asp Gln Gly Asp Leu Ile Asp Ser Ile Glu Ala Asn Val Glu
    210                 215                 220

Ser Ser Glu Val His Val Glu Arg Ala Thr Glu Gln Leu Gln Arg Ala
225                 230                 235                 240

Ala Tyr Tyr Gln Lys Lys Ser Arg Lys Lys Met Cys Ile Leu Val Leu
                245                 250                 255

Val Leu Ser Val Ile Ile Leu Ile Leu Gly Leu Ile Ile Trp Leu Val
            260                 265                 270

Tyr Lys Thr Lys
        275

<210> SEQ ID NO 55
<211> LENGTH: 302
<212> TYPE: PRT
<213> ORGANISM: Homo sapiens

<400> SEQUENCE: 55

Met Ser Glu Asp Glu Glu Lys Val Lys Leu Arg Arg Leu Glu Pro Ala
1               5                   10                  15

Ile Gln Lys Phe Ile Lys Ile Val Ile Pro Thr Asn Leu Glu Arg Leu
            20                  25                  30

Arg Lys His Gln Ile Asn Ile Glu Lys Tyr Gln Arg Cys Arg Ile Trp
        35                  40                  45

Asp Lys Leu His Glu His Ile Asn Ala Gly Arg Thr Val Gln Gln
    50                  55                  60

Leu Arg Ser Asn Ile Arg Glu Ile Glu Lys Leu Cys Leu Lys Val Arg
65                  70                  75                  80

Lys Asp Asp Leu Val Leu Leu Lys Arg Met Ile Asp Pro Val Lys Glu
                85                  90                  95

Glu Ala Ser Ala Ala Thr Ala Glu Phe Leu Gln Leu His Leu Glu Ser
            100                 105                 110

Val Glu Glu Leu Lys Lys Gln Phe Asn Asp Glu Glu Thr Leu Leu Gln
        115                 120                 125

Pro Pro Leu Thr Arg Ser Met Thr Val Gly Gly Ala Phe His Thr Thr
    130                 135                 140

Glu Ala Glu Ala Ser Ser Gln Ser Leu Thr Gln Ile Tyr Ala Leu Pro
145                 150                 155                 160

Glu Ile Pro Gln Asp Gln Asn Ala Ala Glu Ser Arg Glu Thr Leu Glu
                165                 170                 175

Ala Asp Leu Ile Glu Leu Ser Gln Leu Val Thr Asp Phe Ser Leu Leu
```

```
                    180                 185                 190
Val Asn Ser Gln Gln Glu Lys Ile Asp Ser Ile Ala Asp His Val Asn
                195                 200                 205

Ser Ala Ala Val Asn Val Glu Glu Gly Thr Lys Asn Leu Gly Lys Ala
            210                 215                 220

Ala Lys Tyr Lys Leu Ala Leu Pro Val Ala Gly Ala Leu Ile Gly
225                 230                 235                 240

Gly Met Val Gly Gly Pro Ile Gly Leu Leu Ala Cys Phe Lys Val Ala
                245                 250                 255

Gly Ile Ala Ala Leu Gly Gly Val Leu Gly Phe Thr Gly Gly
            260                 265                 270

Lys Leu Ile Gln Arg Lys Lys Gln Lys Met Met Glu Lys Leu Thr Ser
                275                 280                 285

Ser Cys Pro Asp Leu Pro Ser Gln Thr Asp Lys Lys Cys Ser
            290                 295                 300

<210> SEQ ID NO 56
<211> LENGTH: 116
<212> TYPE: PRT
<213> ORGANISM: Homo sapiens

<400> SEQUENCE: 56

Met Ser Ala Thr Ala Thr Ala Pro Pro Ala Pro Ala Gly Glu
1               5                   10                  15

Gly Gly Pro Pro Ala Pro Pro Pro Asn Leu Thr Ser Asn Arg Arg Leu
                20                  25                  30

Gln Gln Thr Gln Ala Gln Val Asp Glu Val Val Asp Ile Met Arg Val
            35                  40                  45

Asn Val Asp Lys Val Leu Glu Arg Asp Gln Lys Leu Ser Glu Leu Asp
        50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
                100                 105                 110

Tyr Phe Ser Ser
        115

<210> SEQ ID NO 57
<211> LENGTH: 100
<212> TYPE: PRT
<213> ORGANISM: Homo sapiens

<400> SEQUENCE: 57

Met Ser Thr Gly Pro Thr Ala Ala Thr Gly Ser Asn Arg Arg Leu Gln
1               5                   10                  15

Gln Thr Gln Asn Gln Val Asp Glu Val Val Asp Ile Met Arg Val Asn
                20                  25                  30

Val Asp Lys Val Leu Glu Arg Asp Gln Lys Leu Ser Glu Leu Asp Asp
            35                  40                  45

Arg Ala Asp Ala Leu Gln Ala Gly Ala Ser Gln Phe Glu Thr Ser Ala
        50                  55                  60

Ala Lys Leu Lys Arg Lys Tyr Trp Trp Lys Asn Cys Lys Met Trp Ala
65                  70                  75                  80

Ile Gly Ile Thr Val Leu Val Ile Phe Ile Ile Ile Ile Val Trp
                85                  90                  95
```

```
Val Val Ser Ser
            100

<210> SEQ ID NO 58
<211> LENGTH: 141
<212> TYPE: PRT
<213> ORGANISM: Homo sapiens

<400> SEQUENCE: 58

Met Pro Pro Lys Phe Lys Arg His Leu Asn Asp Asp Val Thr Gly
1               5                   10                  15

Ser Val Lys Ser Glu Arg Arg Asn Leu Leu Asp Asp Ser Asp Glu
                20                  25                  30

Glu Glu Asp Phe Phe Leu Arg Gly Pro Ser Gly Pro Arg Phe Gly Pro
            35                  40                  45

Arg Asn Asp Lys Ile Lys His Val Gln Asn Gln Val Asp Glu Val Ile
    50                  55                  60

Asp Val Met Pro Glu Asn Ile Thr Lys Val Ile Glu Arg Gly Glu Arg
65                  70                  75                  80

Leu Asp Glu Leu Gln Asp Lys Ser Glu Ser Leu Ser Asp Asn Ala Thr
                85                  90                  95

Ala Phe Ser Asn Arg Ser Lys Gln Leu Arg Arg Gln Met Trp Trp Arg
                100                 105                 110

Gly Cys Lys Ile Lys Ala Ile Met Ala Leu Val Ala Ala Ile Leu Leu
            115                 120                 125

Leu Val Ile Ile Ile Leu Ile Val Met Lys Tyr Arg Thr
        130                 135                 140

<210> SEQ ID NO 59
<211> LENGTH: 220
<212> TYPE: PRT
<213> ORGANISM: Homo sapiens

<400> SEQUENCE: 59

Met Ala Ile Leu Phe Ala Val Val Ala Arg Gly Thr Thr Ile Leu Ala
1               5                   10                  15

Lys His Ala Trp Cys Gly Gly Asn Phe Leu Glu Val Thr Glu Gln Ile
                20                  25                  30

Leu Ala Lys Ile Pro Ser Glu Asn Asn Lys Leu Thr Tyr Ser His Gly
            35                  40                  45

Asn Tyr Leu Phe His Tyr Ile Cys Gln Asp Arg Ile Val Tyr Leu Cys
    50                  55                  60

Ile Thr Asp Asp Asp Phe Glu Arg Ser Arg Ala Phe Asn Phe Leu Asn
65                  70                  75                  80

Glu Ile Lys Lys Arg Phe Gln Thr Thr Tyr Gly Ser Arg Ala Gln Thr
                85                  90                  95

Ala Leu Pro Tyr Ala Met Asn Ser Glu Phe Ser Ser Val Leu Ala Ala
                100                 105                 110

Gln Leu Lys His His Ser Glu Asn Lys Gly Leu Asp Lys Val Met Glu
            115                 120                 125

Thr Gln Ala Gln Val Asp Glu Leu Lys Gly Ile Met Val Arg Asn Ile
        130                 135                 140

Asp Leu Val Ala Gln Arg Gly Glu Arg Leu Glu Leu Leu Ile Asp Lys
145                 150                 155                 160

Thr Glu Asn Leu Val Asp Ser Ser Val Thr Phe Lys Thr Thr Ser Arg
                165                 170                 175
```

```
Asn Leu Ala Arg Ala Met Cys Met Lys Asn Leu Lys Leu Thr Ile Ile
            180                 185                 190

Ile Ile Ile Val Ser Ile Val Phe Ile Tyr Ile Ile Val Ser Pro Leu
        195                 200                 205

Cys Gly Gly Phe Thr Trp Pro Ser Cys Val Lys Lys
    210                 215                 220
```

<210> SEQ ID NO 60
<211> LENGTH: 100
<212> TYPE: PRT
<213> ORGANISM: Homo sapiens

<400> SEQUENCE: 60

```
Met Glu Glu Ala Ser Glu Gly Gly Asn Asp Arg Val Arg Asn Leu
1               5                   10                  15

Gln Ser Glu Val Glu Gly Val Lys Asn Ile Met Thr Gln Asn Val Glu
            20                  25                  30

Arg Ile Leu Ala Arg Gly Glu Asn Leu Glu His Leu Arg Asn Lys Thr
        35                  40                  45

Glu Asp Leu Glu Ala Thr Ser Glu His Phe Lys Thr Thr Ser Gln Lys
    50                  55                  60

Val Ala Arg Lys Phe Trp Trp Lys Asn Val Lys Met Ile Val Leu Ile
65                  70                  75                  80

Cys Val Ile Val Phe Ile Ile Ile Leu Phe Ile Val Leu Phe Ala Thr
                85                  90                  95

Gly Ala Phe Ser
            100
```

<210> SEQ ID NO 61
<211> LENGTH: 203
<212> TYPE: PRT
<213> ORGANISM: Homo sapiens

<400> SEQUENCE: 61

```
Met Ser Ser Asp Phe Glu Gly Tyr Glu Gln Asp Phe Ala Val Leu Thr
1               5                   10                  15

Ala Glu Ile Thr Ser Lys Ile Ala Arg Val Pro Arg Leu Pro Pro Asp
            20                  25                  30

Glu Lys Lys Gln Met Val Ala Asn Val Glu Lys Gln Leu Glu Glu Ala
        35                  40                  45

Lys Glu Leu Leu Glu Gln Met Asp Leu Glu Val Arg Glu Ile Pro Pro
    50                  55                  60

Gln Ser Arg Gly Met Tyr Ser Asn Arg Met Arg Ser Tyr Lys Gln Glu
65                  70                  75                  80

Met Gly Lys Leu Glu Thr Asp Phe Lys Arg Ser Arg Ile Ala Tyr Ser
                85                  90                  95

Asp Glu Val Arg Asn Glu Leu Leu Gly Asp Asp Gly Asn Ser Ser Glu
            100                 105                 110

Asn Gln Arg Ala His Leu Leu Asp Asn Thr Glu Arg Leu Glu Arg Ser
        115                 120                 125

Ser Arg Arg Leu Glu Ala Gly Tyr Gln Ile Ala Val Glu Thr Glu Gln
    130                 135                 140

Ile Gly Gln Glu Met Leu Glu Asn Leu Ser His Asp Arg Glu Lys Ile
145                 150                 155                 160

Gln Arg Ala Arg Glu Arg Leu Arg Glu Thr Asp Ala Asn Leu Gly Lys
                165                 170                 175

Ser Ser Arg Ile Leu Thr Gly Met Leu Arg Arg Gly Cys Ser Val Lys
```

```
                    180                 185                 190
Lys Gln Cys Asn Leu Ser Leu Ala Pro Lys Ala
            195                 200

<210> SEQ ID NO 62
<211> LENGTH: 269
<212> TYPE: PRT
<213> ORGANISM: Homo sapiens

<400> SEQUENCE: 62

Met Arg Asp Arg Leu Pro Asp Leu Thr Ala Cys Arg Lys Asn Asp Asp
1               5                   10                  15

Gly Asp Thr Val Val Val Glu Lys Asp His Phe Met Asp Asp Phe
            20                  25                  30

Phe His Gln Val Glu Glu Ile Arg Asn Ser Ile Asp Lys Ile Thr Gln
        35                  40                  45

Tyr Val Glu Glu Val Lys Lys Asn His Ser Ile Ile Leu Ser Ala Pro
    50                  55                  60

Asn Pro Glu Gly Lys Ile Lys Glu Glu Leu Glu Asp Leu Asn Lys Glu
65                  70                  75                  80

Ile Lys Lys Thr Ala Asn Lys Ile Arg Ala Lys Leu Lys Ala Ile Glu
                85                  90                  95

Gln Ser Phe Asp Gln Asp Glu Ser Gly Asn Arg Thr Ser Val Asp Leu
            100                 105                 110

Arg Ile Arg Arg Thr Gln His Ser Val Leu Ser Arg Lys Phe Val Glu
        115                 120                 125

Ala Met Ala Glu Tyr Asn Glu Ala Gln Thr Leu Phe Arg Glu Arg Ser
    130                 135                 140

Lys Gly Arg Ile Gln Arg Gln Leu Glu Ile Thr Gly Arg Thr Thr Thr
145                 150                 155                 160

Asp Asp Glu Leu Glu Glu Met Leu Glu Ser Gly Lys Pro Ser Ile Phe
                165                 170                 175

Thr Ser Asp Ile Ile Ser Asp Ser Gln Ile Thr Arg Gln Ala Leu Asn
            180                 185                 190

Glu Ile Glu Ser Arg His Lys Asp Ile Met Lys Leu Glu Thr Ser Ile
        195                 200                 205

Arg Glu Leu His Glu Met Phe Met Asp Met Ala Met Phe Val Glu Thr
    210                 215                 220

Gln Gly Glu Met Ile Asn Asn Ile Glu Arg Asn Val Met Asn Ala Thr
225                 230                 235                 240

Asp Tyr Val Glu His Ala Lys Glu Glu Thr Lys Lys Ala Ile Lys Tyr
                245                 250                 255

Gln Ser Lys Ala Arg Arg Val Ser Leu Ala Ser Lys Asn
            260                 265

<210> SEQ ID NO 63
<211> LENGTH: 222
<212> TYPE: PRT
<213> ORGANISM: Homo sapiens

<400> SEQUENCE: 63

Gln Met Ala Ala Leu Ala Pro Leu Pro Pro Leu Pro Ala Gln Phe Lys
1               5                   10                  15

Ser Ile Gln His His Leu Arg Thr Ala Gln Glu His Asp Lys Arg Asp
            20                  25                  30

Pro Val Ala Tyr Tyr Cys Arg Leu Tyr Ala Met Gln Thr Gly Met
        35                  40                  45
```

```
Lys Ile Asp Ser Lys Thr Pro Glu Cys Arg Lys Phe Leu Ser Lys Leu
 50                  55                  60
Met Asp Gln Leu Glu Ala Leu Lys Lys Gln Leu Gly Asp Asn Glu Ala
 65                  70                  75                  80
Ile Thr Gln Glu Ile Val Gly Cys Ala Leu Glu Asn Tyr Ala Leu Lys
                 85                  90                  95
Met Phe Leu Tyr Ala Asp Asn Glu Asp Arg Ala Gly Arg Phe His Lys
                100                 105                 110
Asn Met Ile Lys Ser Phe Tyr Thr Ala Ser Leu Leu Ile Asp Val Ile
            115                 120                 125
Thr Val Phe Gly Glu Leu Thr Asp Glu Asn Val Lys His Arg Lys Tyr
130                 135                 140
Ala Arg Trp Lys Ala Thr Tyr Ile His Asn Cys Leu Lys Glu Trp Gly
145                 150                 155                 160
Asp Ser Ser Arg Pro Cys Trp Glu Leu Lys Lys Ile Met Ile Leu
                165                 170                 175
Lys Lys Met Lys Met Leu Glu Gln Pro Leu Cys Pro Leu Ser Gln Leu
            180                 185                 190
Ser His His Leu Gln Leu Met Thr Gln Gln His Ala Ile Arg Gln
        195                 200                 205
Leu Tyr Trp Asn Thr Asp Ser Ser Gly Cys Thr Arg Ser Ser
210                 215                 220

<210> SEQ ID NO 64
<211> LENGTH: 1527
<212> TYPE: DNA
<213> ORGANISM: Homo sapiens

<400> SEQUENCE: 64
atggaacgaa ggcgtttgtg gggttccatt cagagccgat acatcagcat gagtgtgtgg      60
acaagcccac ggagacttgt ggagctggca gggcagagcc tgctgaagga tgaggccctg     120
gccattgccg ccctggagtt gctgcccagg gagctcttcc cgccactctt catggcagcc     180
tttgacggga gacacagcca gaccctgaag gcaatggtgc aggcctggcc cttcacctgc     240
ctccctctgg gagtgctgat gaagggacaa catcttcacc tggagacctt caaagctgtg     300
cttgatggac ttgatgtgct ccttgcccag gaggttcgcc ccaggaggtg gaaacttcaa     360
gtgctggatt tacggaagaa ctctcatcag gacttctgga ctgtatggtc tggaaacagg     420
gccagtctgt actcatttcc agagccagaa gcagctcagc ccatgacaaa gaagcgaaaa     480
gtagatggtt tgagcacaga ggcagagcag cccttcattc agtagaggt gctcgtagac      540
ctgttcctca aggaaggtgc ctgtgatgaa ttgttctcct acctcattga aaagtgaag      600
cgaaagaaaa atgtactacg cctgtgctgt aagaagctga agattttgc aatgcccatg      660
caggatatca agatgatcct gaaaatggtg cagctggact ctattgaaga tttggaagtg     720
acttgtacct ggaagctacc caccttggcg aaattttctc cttacctggg ccagatgatt     780
aatctgcgta gactcctcct ctcccacatc atgcatcttc cctacatttc cccggagaag     840
gaagagcagt atatcgccca gttcacctct cagttcctca gtctgcagtg cctgcaggct     900
ctctatgtgg actcttttatt tttccttaga ggccgcctgg atcagttgct caggcacgtg     960
atgaaccct tggaaaccct ctcaataact aactgccggc tttcggaagg ggatgtgatg    1020
catctgtccc agagtcccag cgtcagtcag ctaagtgtcc tgagtctaag tggggtcatg    1080
ctgaccgatg taagtcccga gcccctccaa gctctgctgg agagagcctc tgccaccctc    1140
```

-continued

| | |
|---|---|
| caggacctgg tctttgatga gtgtgggatc acggatgatc agctccttgc cctcctgcct | 1200 |
| tccctgagcc actgctccca gcttacaacc ttaagcttct acgggaattc catctccata | 1260 |
| tctgccttgc agagtctcct gcagcacctc atcgggctga gcaatctgac ccacgtgctg | 1320 |
| tatcctgtcc ccctggagag ttatgaggac atccatggta ccctccacct ggagaggctt | 1380 |
| gcctatctgc atgccaggct cagggagttg ctgtgtgagt tggggcggcc cagcatggtc | 1440 |
| tggcttagtg ccaacccctg tcctcactgt ggggacagaa ccttctatga cccggagccc | 1500 |
| atcctgtgcc cctgtttcat gcctaac | 1527 |

<210> SEQ ID NO 65
<211> LENGTH: 1296
<212> TYPE: DNA
<213> ORGANISM: Homo sapiens

<400> SEQUENCE: 65

| | |
|---|---|
| atgggctccg acgtgcggga cctgaacgcg ctgctgcccg ccgtcccctc cctgggtggc | 60 |
| ggcggcggct gtgccctgcc tgtgagcggc gcggcgcagt gggcgccggt gctggacttt | 120 |
| gcgcccccgg gcgcttcggc ttacgggtcg ttgggcggcc ccgcgccgcc accggctccg | 180 |
| ccgccacccc cgccgccgcc gcctcactcc ttcatcaaac aggagccgag ctggggcggc | 240 |
| gcggagccgc acgaggagca gtgcctgagc gccttcactg tccactttc cggccagttc | 300 |
| actggcacag ccggagcctg tcgctacggg cccttcggtc ctcctccgcc cagccaggcg | 360 |
| tcatccggcc aggccaggat gtttcctaac gcgccctacc tgcccagctg cctcgagagc | 420 |
| cagcccgcta ttcgcaatca gggttacagc acggtcacct tcgacgggac gcccagctac | 480 |
| ggtcacacgc cctcgcacca tgcggcgcag ttccccaacc actcattcaa gcatgaggat | 540 |
| cccatgggcc agcagggctc gctgggtgag cagcagtact cggtgccgcc ccggtctat | 600 |
| ggctgccaca ccccccaccga cagctgcacc ggcagccagg ctttgctgct gaggacgccc | 660 |
| tacagcagtg acaatttata ccaaatgaca tcccagcttg aatgcatgac ctggaatcag | 720 |
| atgaacttag gagccacctt aaagggccac agcacagggt acgagagcga taaccacaca | 780 |
| acgcccatcc tctgcggagc ccaatacaga atacacacgc acggtgtctt cagaggcatt | 840 |
| caggatgtgc gacgtgtgcc tggagtagcc ccgactcttg tacggtcggc atctgagacc | 900 |
| agtgagaaac gccccttcat gtgtgcttac ccaggctgca ataagagata ttttaagctg | 960 |
| tcccacttac agatgcacag caggaagcac actggtgaga accataccag tgtgacttc | 1020 |
| aaggactgtg aacgaaggtt ttctcgttca gaccagctca aaagacacca aaggagacat | 1080 |
| acaggtgtga aaccattcca gtgtaaaact tgtcagcgaa agttctcccg gtccgaccac | 1140 |
| ctgaagaccc acaccaggac tcatacaggt aaaacaagtg aaaagccctt cagctgtcgg | 1200 |
| tggccaagtt gtcagaaaaa gtttgcccgg tcagatgaat tagtccgcca tcacaacatg | 1260 |
| catcagagaa acatgaccaa actccagctg gcgctt | 1296 |

<210> SEQ ID NO 66
<211> LENGTH: 1179
<212> TYPE: DNA
<213> ORGANISM: Homo sapiens

<400> SEQUENCE: 66

| | |
|---|---|
| atggaggagc cgcagtcaga tcctagcgtc gagccccctc tgagtcagga aacattttca | 60 |
| gacctatgga aactacttcc tgaaaacaac gttctgtccc ccttgccgtc ccaagcaatg | 120 |
| gatgatttga tgctgtcccc ggacgatatt gaacaatggt tcactgaaga cccaggtcca | 180 |

```
gatgaagctc ccagaatgcc agaggctgct ccccgcgtgg ccccctgcacc agcagctcct      240 acaccggcgg cccctgcacc agcccctcc tggccccctgt catcttctgt cccttcccag       300
aaaacctacc agggcagcta cggtttccgt ctgggcttct tgcattctgg gacagccaag       360
tctgtgactt gcacgtactc ccctgccctc aacaagatgt tttgccaact ggccaagacc       420
tgccctgtgc agctgtgggt tgattccaca ccccgcccg gcacccgcgt ccgcgccatg        480
gccatctaca agcagtcaca gcacatgacg gaggttgtga ggcgctgccc ccaccatgag       540
cgctgctcag atagcgatgg tctggcccct cctcagcatc ttatccgagt ggaaggaaat      600
ttgcgtgtgg agtatttgga tgacagaaac acttttcgac atagtgtggt ggtgccctat     660
gagccgcctg aggttggctc tgactgtacc accatccact acaactacat gtgtaacagt    720
tcctgcatgg gcggcatgaa ccggaggccc atcctcacca tcatcacact ggaagactcc     780
agtggtaatc tactgggacg gaacagcttt gaggtgcgtg tttgtgcctg tcctgggaga     840
gaccggcgca cagaggaaga gaatctccgc aagaaagggg agcctcacca cgagctgccc     900
ccagggagca ctaagcgagc actgcccaac aacaccagct cctctcccca gccaaagaag    960
aaaccactgg atggagaata tttcacccctt cagatccgtg ggcgtgagcg cttcgagatg   1020
ttccgagagc tgaatgaggc cttggaactc aaggatgccc aggctgggaa ggagccaggg   1080
gggagcaggg ctcactccag ccacctgaag tccaaaaagg gtcagtctac ctcccgccat   1140
aaaaaactca tgttcaagac agaagggcct gactcagac                          1179
```

RECOMBINANT VACCINES AND USE THEREOF

This application is a divisional of U.S. patent application Ser. No. 10/575,640, filed on Feb. 9, 2007, now U.S. Pat. No. 8,178,653, which is the National Stage of International Application No. PCT/EP2004/011512, filed on Oct. 13, 2004, each of which is incorporated herein by reference in its entirety.

This application includes biological sequence information, which is set forth in an ASCII text file having the file name "VOS-120-DIV1-SEQ.txt", created on Aug. 29, 2012, and having a file size of 80,864 bytes, which is incorporated herein by reference.

The present invention relates to fusion molecules of antigens, to the nucleic acids coding therefor and to the use of such fusion molecules and nucleic acids. The invention relates in particular to fusion molecules which comprise an antigen and the transmembrane region and cytoplasmic region of an MHC molecule or the cytoplasmic region of an MHC molecule or of a SNARE molecule.

Fusion molecules of the invention can be used for a large number of applications, including in methods for inducing an immune response in a mammal.

Antigen-specific T cell reactions are elicited by antigenic peptides which are bound to the binding groove of glycoproteins of the major histocompatibility complex (MHC), as part of the mechanism of the immune system in which foreign antigens are identified and a response to them is induced. The bound antigenic peptides interact with T cell receptors and thus modulate an immune response. The antigenic peptides are non-covalently bound to certain "binding pockets" formed by polymorphic residues of the binding groove of the MHC protein.

MHC class II molecules are heterodimeric glycoproteins consisting of α and β chains. The α1 and β1 domains of these molecules fold together and form a peptide-binding groove. Antigenic peptides bind to the MHC molecule through interaction between anchor amino acids on the peptide and α1 and β1 domains. The crystal structure of the human class II HLA DR1 complex with an influenza virus peptide shows that the N and C terminal ends of the bound peptide extend out of the binding groove, so that the C terminus of the peptide lies near to the N terminus of the β chain [Brown, J. H. et al., 1993, Nature 364:33-39; Stern, L. J. et al., 1994, Nature 368:215-221]. MHC class I molecules have different domain organizations than MHC class II molecules but generally a similar structure with a peptide-binding site or groove which is remote from the membrane domains [cf. for example Rudensky, A. Y. et al., 1991, Nature 353:622-627].

The initial step in the presentation of a foreign protein antigen is binding of the native antigen to an antigen-presenting cell (APC). After binding to APCs, antigens penetrate into the cells, either by phagocytosis, receptor-mediated endocytosis or pinocytosis. Such internalized antigens are located in intracellular membrane-bound vesicles called endosomes. Following endosome-lysosome fusion, the antigens are processed to small peptides by cellular proteases present in the lysosomes. The peptides associate with the α and β chains of MHC class II molecules within these lysosomes. These MHC class II molecules, which had previously been synthesized in the rough endoplasmic reticulum, are transported sequentially to the Golgi complexes and then to the lysosomal compartment. The peptide-MHC complex is presented on the surface of APCs for T- and B-cell activation. Therefore, the accessibility of proteolytic processing sites in the antigen, the stability of the resulting peptides in the lysosomes and the affinities of the peptides for MHC molecules are determining factors for the immunogenicity of a specific epitope.

Recombinant vaccines have particular importance in human and veterinary medicine as agents and medicaments for the prophylaxis and therapy of infectious diseases and cancers. The aim of vaccination with a recombinant vaccine is to induce a specific immune response to a defined antigen, which response has preventive or therapeutic activity against defined diseases.

A factor which is essential for the efficacy of a recombinant vaccine is optimal stimulation of T lymphocytes of the immunized organism. Thus, a number of animal-experimental investigations demonstrates that both optimal stimulation of $CD8^+$ and $CD4^+$ lymphocytes is necessary for effective immunotherapy of tumors. The known major types of recombinant vaccines are based on recombinant proteins, synthetic peptide fragments, recombinant viruses and nucleic acid vaccines based on DNA or RNA. In recent years, vaccines based on DNA and RNA nucleic acids have become increasingly important. However, only very poor or even no stimulation of $CD4^+$ lymphocytes can be achieved with recombinant vaccines based on nucleic acids for very many aims, inter alia tumour antigens. For this reason, a number of genetic modifications has been developed with the intention of increasing the immunogenicity of recombinant vaccines. Various methods have been tested in this connection to date, inter alia heterogenization of immunogens by altering the primary sequence or by fusion to foreign epitopes, e.g. from bacteria or viruses [Lowenadler, B. et al., 1990, Eur. J. Immunol. 20: 1541-45; Clarke, B. E. et al., 1987, Nature 330: 381-84] and preparation of chimeric products consisting of the actual antigen and immunomodulatory proteins such as cytokines [Ruckert, R. et al., 1998, Eur. J. Immunol. 28: 3312-20; Harvill, E. T., J. M. Fleming, and S. L. Morrison, 1996, J. Immunol. 157: 3165-70]. Although vaccines based on heterogenization induce enhanced immune responses, they have the great disadvantage that immunostimulation against the foreign epitope predominates and that immune responses against the actual vaccine target remain only moderate in some cases.

A further attractive possibility is fusion to sequences of proteins intended to permit translocation of the protein into degrading cell compartments. However, it is now known that these modifications lead to only a moderate improvement in stimulation of $CD4^+$ lymphocytes and to scarcely any enhancement of $CD8^+$ immune responses [Wu, T. C. et al., 1995, Proc. Natl. Acad. Sci. U.S.A. 92: 11671-11675; Bonini, C. et al., 2001, J. Immunol. 166: 5250-57, Su, Z. et al., 2002, Cancer Res. 62: 5041-5048].

It would thus be desirable for vaccines which distinctly increase antigen presentation and thus immunogenicity in relation to a particular antigen to be available. It would further be desirable for it to be possible to modify vaccines systematically in such a way that α maximum immune response by $CD4^+$ and $CD8^+$ lymphocytes results, without the need to introduce foreign epitopes.

This object is achieved according to the invention by the subject matter of the claims.

It has been possible to establish according to the invention that fusion molecules comprising antigen molecules and parts of histocompatibility antigens show, when used as vaccines, an immunogenicity which is increased >100-fold compared with the unmodified antigens, and that surprisingly both immune responses of $CD4^+$ and $CD8^+$ T lymphocytes are increased in a manner not previously described.

The present invention relates in general to fusion molecules of antigen molecules and to the use of such fusion molecules.

In one aspect, the invention relates to a fusion molecule which comprises an antigen and the cytoplasmic region of a chain of an MHC molecule, or an antigen, a transmembrane region and the cytoplasmic region of a chain of an MHC molecule. It is preferred for both the transmembrane region and the cytoplasmic region to be derived from a MHC molecule. In addition, the fusion molecule preferably comprises no MHC binding domain.

The invention further relates to a fusion molecule which comprises an antigen and a chain of an MHC molecule or a part thereof, where the part comprises at least the transmembrane region and the cytoplasmic region of the chain of the MHC molecule. The part of the chain of an MHC molecule preferably does not comprise the MHC binding domain or parts thereof. There is thus provided in particular a fusion molecule which comprises an antigen and a part of a chain of an MHC molecule, which part corresponds essentially to the sequence of the transmembrane region connected to the cytoplasmic region of an MHC molecule, where the expression "transmembrane region connected to the cytoplasmic region" relates to the segment of a chain of an MHC molecule which starts with the N-terminal end of the transmembrane region and terminates with the C-terminal end of the cytoplasmic region, in particular the C-terminal end of the complete chain of the MHC molecule. In this embodiment, the connection of the transmembrane region to the cytoplasmic region corresponds to the naturally occurring connection between these regions.

The invention further provides a fusion molecule which comprises an antigen and a chain of an MHC molecule or a part thereof, where the part essentially lacks the complete N-terminal extracellular domains of the MHC molecule.

In a particularly preferred embodiment, the fusion molecules of the invention consist of a fusion of an antigen, where appropriate with a leader sequence at its N-terminal end, to a transmembrane region, preferably a transmembrane region of a chain of an MHC molecule, at the C-terminal end of the antigen and of a cytoplasmic region of a chain of an MHC molecule at the C-terminal end of the transmembrane region.

In a particularly preferred embodiment, the fusion molecules of the invention comprise a leader sequence, preferably a peptide sequence having the properties of a secretion signal which is able in particular to control translocation of a protein or peptide through a membrane. It is possible to use as leader sequence the secretion signal of any type I transmembrane protein, where the expression "type I transmembrane protein" relates to those transmembrane proteins whose C terminus is located in the cytoplasm. In a particular embodiment, the leader sequence is derived from a chain of an MHC molecule. The leader sequence is preferably located at the N-terminal end of the fusion molecules of the invention.

In a further aspect, the invention relates to a fusion molecule where essentially the complete N-terminal extracellular domains of an MHC molecule are replaced by an antigen having a leader sequence at its N-terminal end.

It is preferred in a fusion molecule of the invention for the antigen to be covalently connected at its N terminus to the C terminus of a leader sequence, and the C terminus of the antigen molecule is connected to the N terminus of the transmembrane region which in turn is connected at the C terminus to the N terminus of the cytoplasmic region of an MHC molecule.

Thus, the fusion molecule of the invention preferably has the following arrangement: N terminus leader sequence/antigen/transmembrane region/cytoplasmic region C terminus.

In a particularly preferred embodiment, the fusion molecule of the invention consists essentially of the leader sequence, the antigen, the transmembrane region and the cytoplasmic region.

In a particularly preferred embodiment, the antigen is a peptide, polypeptide or protein, and the fusion molecule of the invention is a protein or polypeptide.

In one embodiment, a plurality of antigens which may be identical or different are present in the fusion molecule of the invention, i.e. at least 2, preferably 2 to 10, more preferably 2 to 5, even more preferably 2 to 3, in particular 2, antigens. These multiply coupled antigens may be present separate from one another or in series one after the other, where appropriate separated by a linker, as tandem constructs. It is preferred for an immune response to various antigens to be induced thereby on administration.

The antigen may be complete or truncated, i.e. it contains only a part of the natural protein or polypeptide which serves as antigen.

The leader sequence and/or the transmembrane region of the fusion molecules of the invention are preferably derived from MHC molecules, in particular of class I or II. It is more preferred for the leader sequence and/or the transmembrane region and/or the cytoplasmic region of the fusion molecules of the invention to be derived from MHC molecules, in particular of class I or II.

It is also possible according to the invention for one or more, preferably flexible, linker sequences (connecting sequences) to be present in the fusion molecule, possibly being located between the leader sequence and the antigen, between the antigen and the transmembrane region and/or between the transmembrane region and the cytoplasmic region. It is preferred according to the invention for a linker sequence to comprise about 7 to 20 amino acids, more preferably about 8 to 16 amino acids, and in particular about 8 to 12 amino acids.

The linker sequence in fusion molecules of the invention is preferably flexible and thus does not hold the peptide connected therewith in a single, unwanted conformation. The linker preferably comprises in particular amino acids having small side chains, such as glycine, alanine and serine, in order to make flexibility possible. The linker sequence preferably comprises no proline residue, which might inhibit the flexibility.

In a further embodiment, the leader sequence, the antigen, the transmembrane region and/or the cytoplasmic region are connected together directly without a linker.

The leader sequence preferably has the sequence shown in SEQ ID NO: 2 or a sequence derived therefrom, or is encoded by the sequence shown in SEQ ID NO: 1 or a sequence derived therefrom. The transmembrane-cytoplasmic region preferably has the sequence shown in SEQ ID NO: 4 or 6 or a sequence derived therefrom, or is encoded by the sequence shown in SEQ ID NO: 3 or 5 or a sequence derived therefrom.

In further preferred embodiments, the transmembrane-cytoplasmic or the exclusively cytoplasmic region is derived from sequence-related MHC molecules (inter alia HLA-A, HLA-B, HLA-C, HLA-E, HLA-F, HLA-DRa, HLA-Db, HLA-DQa, HLA-DQb, HLA-DPa, HLA-DPb, CD1a, CD1b, CD1c). Preferred transmembrane-cytoplasmic regions have a sequence selected from the group consisting of the sequences depicted in SEQ ID NO: 15, 17, 19, 21, 23, 25, 27, 29, 31, 33, 35, 37, 39, 41, and sequences derived therefrom. In further embodiments, the exclusively cytoplasmic regions have a sequence selected from the group consisting of the sequences depicted in SEQ ID NO: 16, 18, 20, 22, 24, 26, 28, 30, 32, 34, 36, 38, 40, 42, and sequences derived therefrom. Further embodiments also provide for the use of varied sequences, e.g. modified or orthologous sequences from different organisms. Sequences particularly preferred in this connection are those having at the C-terminal end a homology of more than 60% with the sequences shown in SEQ ID NO: 16, 18, 20, 22, 24, 26, 28, 30, 32, 34, 36, 38, 40, 42.

In a particularly preferred embodiment, the fusion molecule of the invention comprises the amino acid sequence shown in SEQ ID NO: 12 or 14, or a sequence derived therefrom.

The invention further relates to a fusion molecule comprising an antigen and a SNARE protein (in particular Cis-golgi SNARE p28, VTI1b, membrin, pallidin, syntaxin-5, syntaxin-6, syntaxin-7, syntaxin-8, syntaxin-10, syntaxin-10a, syntaxin-11, syntaxin-12, syntaxin-17, VAMP-2, VAMP-3, VAMP-4, VAMP-7, VAMP8, VTI1-a-beta, XP350893, LIP5 (SEQ ID NO: 43-63)) or a sequence which comprises one or more SNARE motifs. Targeted transport of the antigen into a defined compartment (e.g. lysosomes and endosomes) is possible by fusing an antigen to a SNARE protein or a SNARE motif (preferably at the C terminus of the SNARE protein or motif). A further possibility with such a targeted transport is for immunogenic epitopes of the antigen to be generated and presented in a compartment, as can be established experimentally.

SNARE proteins are membrane-associated proteins whose common feature is the SNARE motif which comprises 60-70 amino acids. SNARE proteins are functionally involved in the transport and fusion of vesicles in the cell. Eukaryotic organisms have a large number of different SNARE proteins which are associated with different vesicle membranes in the cell (inter alia endosomal, lysosomal, Golgi, plasma membranes). The cytoplasmic regions of the SNARE proteins have a dual function. Firstly, they serve as trafficking signals (address labels) which specify the destination of the protein and of the associated membrane. Secondly, the domains may contribute through hetero- and homoassociation (joining together) to fusion of different vesicles (e.g. endosomes with lysosomes).

It is also possible according to the invention for the SNARE-antigen fusion molecules to comprise linker sequences between the SNARE portion and the antigen portion. Also included in relation to the antigen and the linker sequence of the SNARE-antigen fusion molecules are all the embodiments described above. A linker in relation to the SNARE-antigen fusion molecules preferably comprises 80-120 amino acids. In a particular embodiment, the linker comprises a transmembrane region. The invention thus relates to fusion molecules which comprise a SNARE protein or a SNARE motif fused to an antigen or a transmembrane region and an antigen. Such fusion molecules are shown for example in FIG. 7.

In a further aspect, the invention relates to nucleic acids and derivatives thereof which code for the fusion molecules described above and are preferably able to express these fusion molecules. The term "nucleic acid" hereinafter also includes derivatives thereof.

In a particularly preferred embodiment, the nucleic acid which codes for a fusion molecule of the invention comprises the nucleic acid sequence shown in SEQ ID NO: 11 or 13, or a sequence derived therefrom.

The invention also relates to host cells which comprise a nucleic acid of the invention.

The host cell may moreover comprise a nucleic acid which codes for an HLA molecule. In one embodiment, the host cell expresses the HLA molecule endogenously. In a further embodiment, the host cell expresses the HLA molecule recombinantly. The host cell is preferably non-proliferative. In a preferred embodiment, the host cell is an antigen-presenting cell, in particular a dendritic cell, a monocyte or a macrophage.

In a further aspect, the invention relates to a pharmaceutical composition, in particular a vaccine, which comprises one or more of the fusion molecules of the invention and/or one or more of the nucleic acids coding therefor and/or one or more of the host cells of the invention.

In a further aspect, the invention provides a method for increasing the amount of MHC/peptide complexes in a cell, where the method comprises the provision of a fusion molecule of the invention or of a nucleic acid coding therefor for the cell. The cell is preferably present in a living creature, and the method comprises administering a fusion molecule of the invention or a nucleic acid coding therefor to the living creature. In a preferred embodiment, the cell is an antigen-presenting cell, in particular a dendritic cell, a monocyte or a macrophage.

In a further aspect, the invention provides a method for increasing the presentation of cell surface molecules on cells which are able to present antigens (such as B cells and macrophages, generally called "APC"). The antigen-presenting activity of such cells is enhanced by providing a fusion molecule of the invention or a nucleic acid coding therefor for the cells. Such an enhancement of the antigen-presenting activity in turn preferably enhances the primary activation of T cells, in particular of $CD4^+$ and $CD8^+$ lymphocytes, which respond to the antigen. The cell is preferably present in a living creature, and the method comprises administering a fusion molecule of the invention or a nucleic acid coding therefor to the living creature.

In a further aspect, the invention provides a method for inducing an immune response in a living creature, where the method comprises the administration of a fusion molecule of the invention and/or a nucleic acid coding therefor and/or a host cell of the invention to the living creature.

In a further aspect, the invention provides a method for stimulating or activating T cells, especially $CD4^+$ and $CD8^+$ lymphocytes, in vitro or in a living creature, in particular a patient, where the method comprises the provision for the T cells or administration to the living creature of a fusion molecule of the invention and/or a nucleic acid coding therefor and/or a host cell of the invention. Such a stimulation or activation is preferably expressed in an expansion, cytotoxic reactivity and/or cytokine release by the T cells.

A further aspect provides a method for the treatment, vaccination or immunization of a living creature, where the method comprises the administration a fusion molecule of the invention and/or a nucleic acid coding therefor and/or a host cell of the invention to the living creature. In this connection, the antigens employed in the fusion molecule of the invention or the nucleic acid coding therefor are in particular those which are known to be effective without the alteration according to the invention for the intended treatment, vaccination or immunization.

The methods described above are particularly suitable for a treatment or prophylaxis of infectious diseases caused for example by bacteria or viruses. In particular embodiments, the antigen used according to the invention is derived from an infectious agent such as hepatitis A, B, C, HIV, mycobacteria, malaria pathogens, SARS pathogens, herpesvirus, influenzavirus, poliovirus or from bacterial pathogens such as chlamydia and mycobacteria. A particularly beneficial application of the present invention is in cancer immunotherapy or vaccination, where there is in particular enhancement of activation of tumor antigen-reactive T cells, thus improving the prospects for T-cell immunotherapy or vaccination against tumor cells.

In specific embodiments, the antigen used according to the invention is selected from the group consisting of the following antigens: p53, preferably encoded by the sequence shown in SEQ ID NO: 66, ART-4, BAGE, ss-catenin/m, Bcr-abL CAMEL, CAP-1, CASP-8, CDC27/m, CDK4/m, CEA, CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11 or MAGE-A12, MAGE-B, MAGE-C, MART-1/melan-A, MC1R, myosin/m, MUC1, MUM-1, -2, -3, NA88-A, NF1, NY-ESO-1, NY-BR-1, p190 minor bcr-abL Pml/RARa, PRAME, proteinase-3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT, preferably WT-1, in particular encoded by the sequence shown in SEQ ID NO: 65.

DETAILED DESCRIPTION OF THE INVENTION

The terms "domain" or "region" relate to a particular part of an amino acid sequence which can preferably be connected to a specific function or structure. For example, the α and β polypeptides of an MHC class II molecule have two domains, α1, α2, and β1, β2, respectively, a transmembrane region and a cytoplasmic region. In a similar manner, the α chain of MHC class I molecules has three domains, α1, α2 and α3, a transmembrane region and a cytoplasmic region.

In one embodiment, the complete domain or region is included in a selection of the sequence of a particular domain or region for deletion or incorporation into a fusion molecule of the invention. In order to ensure this, the sequence of the relevant domain or region can be extended in order to comprise parts of a linker or even parts of the adjacent domain or region. The term "essentially" in relation to a domain or region is to be understood in this sense.

The term "transmembrane region" relates to the part of a protein which essentially accounts for the portion present in a cellular membrane and preferably serves to anchor the protein in the membrane. A transmembrane region is preferably according to the invention an amino acid sequence which spans the membrane once. However, it is also possible in certain embodiments to use a transmembrane region which spans the membrane more than once. The transmembrane region will generally have 15-25 preferably hydrophobic uncharged amino acids which assume for example an α-helical conformation. The transmembrane region is preferably derived from a protein selected from the group consisting of MHC molecules, immunoglobulins, CD4, CD8, the CD3 ζ chain, the CD3 γ chain, the CD3 δ chain and the CD3ε chain.

The transmembrane region typically consists in the case of the α and β chains of the MHC class II molecule of about 20 hydrophobic amino acids which are connected to the carboxy-terminal end of the antigen. These residues allow the protein to span the membrane. The transmembrane region terminates with about 6-32 residues which comprise the cytoplasmic tail at the carboxy-terminal end of each of these chains. It has been shown that these transmembrane and cytoplasmic regions can be replaced by sequences which signal a GPI binding, and that the chimeric GPI-anchored class II molecules are membrane-bound (Wettstein, D. A., J. J. Boniface, P. A. Reay, H. Schild and M. M. Davis, 1991, J. Exp. Med. 174: 219-228). Such embodiments are encompassed by the term "transmembrane region" according to the invention. GPI-bound membrane anchor domains have been defined in a number of proteins, including decay-accelerating factor (DAF), CD59 and human placental alkaline phosphatase (HPAP) (Wettstein, D. A., J. J. et al., 1991, J. Exp. Med. 174:219-228). For example, the 38 carboxy-terminal amino acids of HPAP are sufficient for functioning as signal sequence for GPI binding. If the DNA sequence coding for this domain is connected to a secreted molecule, such as the soluble part of the MHC class II α or β chain, there is formation of a membrane-bound chimeric molecule (Wettstein, D. A. et al., 1991, J. Exp. Med. 174: 219-228), and a method of this type can be employed to anchor fusion molecules of the invention to a cell membrane.

The term "major histocompatibility complex" and the abbreviation "MHC" relate to a complex of genes which occurs in all vertebrates. The function of MHC proteins or molecules in signaling between lymphocytes and antigen-presenting cells in normal immune responses involves them binding peptides and presenting them for possible recognition by T-cell receptors (TCR). MHC molecules bind peptides in an intracellular processing compartment and present these peptides on the surface of antigen-presenting cells to T cells. The human MHC region, also referred to as HLA, is located on chromosome 6 and comprises the class I region and the class II region.

The term "MHC class I" or "class I" relates to the major histocompatibility complex class I proteins or genes. Within the human MHC class I region there are the HLA-A, HLA-B, HLA-C, HLA-E, HLA-F, CD1a, CD1b and CD1c subregions.

The class I α chains are glycoproteins having a molecular weight of about 44 kDa. The polypeptide chain has a length of somewhat more than 350 amino acid residues. It can be divided into three functional regions: an external, a transmembrane and a cytoplasmic region. The external region has a length of 283 amino acid residues and is divided into three domains, α1, α2 and α3. The domains and regions are usually encoded by separate exons of the class I gene. The transmembrane region spans the lipid bilayer of the plasma membrane. It consists of 23 usually hydrophobic amino acid residues which are arranged in an α helix. The cytoplasmic region, i.e. the part which faces the cytoplasm and which is connected to the transmembrane region, typically has a length of 32 amino acid residues and is able to interact with the elements of the cytoskeleton. The α chain interacts with β2-microglobulin and thus forms α-β2 dimers on the cell surface.

The term "MHC class II" or "class II" relates to the major histocompatibility complex class II proteins or genes. Within the human MHC class II region there are the DP, DQ and DR subregions for class II a chain genes and β chain genes (i.e. DPα, DPβ, DQα, DQβ, DRα and DRβ).

Class II molecules are heterodimers each consisting of an α chain and a β chain. Both chains are glycoproteins having a molecular weight of 31-34 kDa (α) or 26-29 kDA (β). The total length of the α chains varies from 229 to 233 amino acid residues, and that of the β chains from 225 to 238 residues. Both α and β chains consist of an external region, a connecting peptide, a transmembrane region and a cytoplasmic tail. The external region consists of two domains, α1 and α2 or β1 and β2. The connecting peptide is respectively 13 and 9 residues long in α and β chains. It connects the two domains to the transmembrane region which consists of 23 amino acid residues both in α chains and in β chains. The length of the cytoplasmic region, i.e. the part which faces the cytoplasm and which is connected to the transmembrane region, varies from 3 to 16 residues in α chains and from 8 to 20 residues in β chains.

The term "chain of an MHC molecule" relates according to the invention to the α chain of an MHC class I molecule or to the α and β chains of an MHC class II molecule. The α chains of an MHC class I molecule, from which the fusion molecules of the invention can be derived, comprise the HLA-A, -B and -C α chains. The α chains of an MHC class II molecule, from which the fusion molecules of the invention may be derived, comprise HLA-DR, -DP and -DQ α chains, in particular HLA-DR1, HLA-DR2, HLA-DR4, HLA-DQ1, HLA-DQ2 and HLA-DQ8 α chains and, in particular, α chains encoded by DRA*0101, DRA*0102, DQA1*0301 or DQA1*0501 alleles. The β chains of an MHC class II molecule, from which the fusion molecules of the invention may be derived, comprise HLA-DR, -DP and -DQ β chains, in particular HLA-DR1, HLA-DR2, HLA-DR4, HLA-DQ1, HLA-DQ2 and HLA-DQ8 β chains and, in particular, β chains encoded by DRB1*01, DRB1*15, DRB1*16, DRB5*01, DQB1*03 and DQB1*02 alleles.

The term "MHC binding domain" relates to the "MHC class I binding domain" and "MHC class II binding domain".

The term "MHC class I binding domain" relates to the region of an MHC class I molecule or of an MHC class I chain which is necessary for binding to an antigenic peptide. An MHC class I binding domain is formed mainly by the α1 and α2 domains of the MHC class I α chain. Although the α3 domain of the α chain and β2-microglobulin do not represent essential parts of the binding domain, they are presumably important for stabilizing the overall structure of the MHC class I molecule and therefore the term "MHC class I binding domain" preferably includes these regions. An MHC class I binding domain can also be essentially defined as the extracellular domain of an MHC class I molecule, distinguishing it from the transmembrane and cytoplasmic regions.

The term "MHC class II binding domain" relates to the region of an MHC class II molecule or of an MHC class II chain which is necessary for binding to an antigenic peptide. An MHC class II binding domain is mainly formed by the β1 and β1 domains of the MHC class II α and β chains. The α2 and β2 domains of these proteins are, however, presumably also important for stabilizing the overall structure of the MHC binding groove, and therefore the term "MHC class II binding domain" according to the invention preferably includes these regions. An MHC class II binding domain can also be defined essentially as the extracellular domain of an MHC class II molecule, distinguishing it from the transmembrane and cytoplasmic domains.

The exact number of amino acids in the various MHC molecule domains or regions varies depending on the mammalian species and between gene classes within a species. When selecting the amino acid sequence of a particular domain or region, maintenance of the function of the domain or region is much more important than the exact structural definition, which is based on the number of amino acids. The skilled worker is also aware that the function can also be maintained if rather less than the complete amino acid sequence of the selected domain or region is used.

The term "antigen" relates to an agent against which an immune response is to be generated. The term "antigen" includes in particular proteins, peptides, polysaccharides, nucleic acids, especially RNA and DNA, and nucleotides. The term "antigen" also includes derivatized antigens as secondary substance which becomes antigenic—and sensitizing—only through transformation (e.g. intermediately in the molecule, by completion with body protein), and conjugated antigens which, through artificial incorporation of atomic groups (e.g. isocyanates, diazonium salts), display a new constitutive specificity. In a preferred embodiment, the antigen is a tumor antigen, i.e. a constituent of cancer cells which may be derived from the cytoplasm, the cell surface and the cell nucleus, in particular those antigens which are produced, preferably in large quantity, intracellularly or as surface antigens on tumor cells. Examples are carcinoembryonic antigen, α1-fetoprotein, isoferritin and fetal sulfoglycoprotein, α2-H-ferroprotein and γ-fetoprotein and various viral tumor antigens. In a further embodiment, the antigen is a viral antigen such as viral ribonucleoproteins or envelope proteins. In particular, the antigen or peptides thereof should be presented by MHC molecules and thus be able to modulate, in particular, activate, cells of the immune system, preferably $CD4^+$ and $CD8^+$ lymphocytes, in particular by modulating the activity of a T-cell receptor, and thus preferably induce T cell proliferation.

The term "MHC/peptide complex" relates to a non-covalent complex of the binding domain of an MHC class I or MHC class II molecule and of an MHC class I or MHC class II binding peptide.

The term "MHC binding peptide" or "binding peptide" relates to a peptide which binds to an MHC class I and/or an MHC class II molecule. In the case of class I MHC/peptide complexes, the binding peptides typically have a length of 8-10 amino acids, although longer or shorter peptides may be active. In the case of class II MHC/peptide complexes, the binding peptides typically have a length of 10-25 amino acids and in particular of 13-18 amino acids, although longer and shorter peptides may be active.

Fusion molecules of the invention and the nucleic acids coding therefor can generally be prepared by recombinant DNA techniques such as preparation of plasmid DNA, cleavage of DNA with restriction enzymes, ligation of DNA, transformation or transfection of a host, cultivation of the host and isolation and purification of the expressed fusion molecule. Such methods are known and described for example in Sambrook et al., Molecular Cloning (2nd edition, 1989).

DNA coding for the antigen can be obtained by isolating DNA from natural sources or by known synthetic methods such as the phosphate triester method; cf., for example, Oligonucleotide Synthesis, IRL Press (M. J. Gait, editor, 1984). Synthetic oligonucleotides can also be prepared with the aid of commercially available automatic oligonucleotide synthesizers.

The proportions of MHC molecules in the fusion molecules of the invention suitably correspond, in relation to the amino acid sequence, to naturally occurring MHC molecules from humans, mice or other rodents or other mammals or are derivatives thereof.

DNA sources coding for MHC proteins are known, such as human lymphoblastoid cells. After isolation, the gene coding for the MHC molecule, or an interesting part thereof, can be amplified by polymerase chain reaction (PCR) or other known methods. Suitable PCR primers for amplifying the gene for the MHC peptide can attach restriction sites to the PCR product.

It is preferred according to the invention to prepare DNA constructs which comprise nucleic acid sequences coding for the leader sequence, the transmembrane region and the cytoplasmic region, and which comprise a restriction cleavage site between the leader sequence and the transmembrane region, so that essentially any nucleotide sequence coding for an interesting antigen can be incorporated into the construct.

In a preferred method for preparing fusion molecules of the invention, DNA sequences are disposed in such a way that the C-terminal end of the leader sequence is linked to the N-terminal end of the antigen, the C-terminal end of the antigen is linked to the N-terminal end of the transmembrane region, and the C-terminal end of the transmembrane region is linked to the N-terminal end of the cytoplasmic region. As discussed above, restriction cleavage sites are preferably incorporated between the end of the leader sequence and the start of the transmembrane region, so that essentially any nucleic acid which codes for an interesting antigen can be linked to the nucleic acid sequence for the transmembrane region.

An expressed fusion molecule of the invention may be isolated and purified in a manner known per se. Typically, the culture medium will be centrifuged and the supernatant will then be purified by affinity or immunoaffinity methods comprising the use of monoclonal antibodies which bind to the expressed fusion molecule. The fusion molecule may also comprise a sequence which assists purification, e.g. a 6×His tag.

The ability of a fusion molecule of the invention to modulate the activity of a T-cell receptor (including inactivation of T-cell responses) can easily be determined by an in vitro assay. Typically, T cells are provided for the assays by transformed T-cell lines, such as T-cell hybridomas or T cells which are isolated from a mammal such as a human or a rodent such as a mouse. Suitable T-cell hybridomas are freely available or can be prepared in a manner known per se. T cells can be isolated in a manner known per se from a mammal; cf., for example, Shimonkevitz, R. et al., 1983, J. Exp. Med. 158: 303.

A suitable assay for determining whether a fusion molecule of the invention is able to modulate the activity of T cells takes place as follows by steps 1-4 hereinafter. T cells suitably express a marker which can be assayed and indicates the T-cell activation or modulation of T-cell activity after activation. Thus, the mouse T-cell hybridoma DO11.10, which expresses interleukin-2 (IL-2) on activation, can be used. IL-2 concentrations can be measured in order to determine whether a specific presenting peptide is able to modulate the activity of this T-cell hybridoma. A suitable assay of this type is carried out by the following steps:

1. T cells are obtained for example from an interesting T-cell hybridoma or by isolation from a mammal.
2. The T cells are cultivated under conditions which permit proliferation.
3. The growing T cells are brought into contact with antigen-presenting cells which in turn have been brought into contact with a fusion molecule of the invention or with a nucleic acid coding therefor.
4. The T cells are assayed for a marker, e.g. IL-2 production is measured.

The T cells used in the assays are incubated under conditions suitable for proliferation. For example, a DO11.10 T-cell hybridoma is suitably incubated in complete medium (RPMI 1640, supplemented with 10% FBS, penicillin/streptomycin, L-glutamine and $5×10^{-5}$ M 2-mercaptoethanol) at about 37° C. with 5% $CO_2$. Serial dilutions of the fusion molecule of the invention can be assayed. T-cell activation signals are provided by antigen-presenting cells which have been loaded with the suitable antigenic peptide.

As an alternative to measuring an expressed protein such as IL-2, it is possible to determine the modulation of T-cell activation suitably by changes in the proliferation of antigen-dependent T cells, as measured by known radiolabeling methods. For example, a labeled (such as tritiated) nucleotide can be introduced into an assay culture medium. The introduction of such a labeled nucleotide into the DNA serves as measurand for T-cell proliferation. This assay is unsuitable for T cells not requiring antigen presentation for growth, such as T-cell hybridomas. The assay is suitable for measuring the modulation of T-cell activation by fusion molecules in the case of untransformed T cells isolated from mammals.

The ability of a fusion molecule of the invention to induce an immune response, including making it possible to vaccinate against a target disease, can be determined simply by an in vivo assay. For example, a fusion molecule of the invention or a nucleic acid coding therefor can be administered to a mammal such as a mouse, and blood samples be taken from the mammal at the time of the first administration and several times at periodic intervals thereafter (such as 1, 2, 5 and 8 weeks after administration of the fusion molecule or of the nucleic acid coding therefor). Serum is obtained from the blood samples and assayed for the appearance of antibodies resulting from the immunization. Antibody concentrations can be determined. In addition, T lymphocytes can be isolated from the blood or from lymphatic organs and be functionally assayed for reactivity to the antigen or epitopes derived from the antigen. All the readout systems known to the skilled worker, inter alia proliferation assay, cytokine secretion, cytotoxic activity, tetramer analysis, can be used in this connection.

Methods of the invention for inducing an immune response, including vaccination of a living creature against a target disease, can be used in combination with known methods for inducing an immune response. For example, a fusion molecule of the invention or a nucleic acid coding therefor can be administered to a living creature in an arrangement or combination with administration of a vaccine composition in order to enhance or prolong the desired effect of such a vaccine composition.

The term "derived" means according to the invention that a particular entity, in particular a particular sequence, is present in the object from which it is derived, in particular an organism or molecule. In the case of nucleic acid and amino acid sequences, especially particular sequence regions, "derived" additionally means that the relevant nucleic acid or amino acid sequence is derived, consistent with the definitions hereinafter, from a nucleic acid or amino acid sequence which is present in the object. Thus, the expression "sequence or region derived from an MHC molecule" means that the sequence or region is present in an MHC molecule or is derived, consistent with the definitions hereinafter, from a sequence or region which is present in an MHC molecule.

A nucleic acid is according to the invention preferably deoxyribonucleic acid (DNA) or ribonucleic acid (RNA). Nucleic acids include according to the invention genomic DNA, cDNA, mRNA, recombinantly prepared and chemically synthesized molecules. A nucleic acid may according to the invention be in the form of a molecule which is single stranded or double stranded and linear or closed covalently to form a circle.

A sequence derived from a nucleic acid sequence or the expression "sequence derived from a nucleic acid sequence" relates according to the invention to homologous sequences and derivatives of the former sequence.

Homologous nucleic acid sequences display according to the invention at least 40%, in particular at least 50%, at least 60%, at least 70%, at least 80%, at least 90% and preferably at least 95%, at least 98 or at least 99% identity of the nucleotides.

A nucleic acid is "homologous" to another nucleic acid in particular when the two sequences of the complementary strands are able to hybridize with one another and enter into a stable duplex, the hybridization preferably taking place under conditions which permit specific hybridization between polynucleotides (stringent conditions). Stringent conditions are described for example in Molecular Cloning: A Laboratory Manual, J. Sambrook et al., editors, 2nd edition, Cold Spring Harbor Laboratory Press, Cold Spring Harbor, N.Y., 1989 or Current Protocols in Molecular Biology, F. M. Ausubel et al., editors, John Wiley & Sons, Inc., New York, and relate for example to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After the hybridization, the membrane onto which the DNA has been transferred is for example washed in 2×SSC at room temperature and then in 0.1-0.5×SSC/0.1× SDS at temperatures of up to 68° C.

"Derivative" of a nucleic acid means according to the invention that single or multiple nucleotide substitutions, deletions and/or additions are present in the nucleic acid. The term "derivative" also includes in addition chemical derivatization of a nucleic acid on a base, a sugar or phosphate of a nucleotide. The term "derivative" also includes nucleic acids which comprise non-naturally occurring nucleotides and nucleotide analogs.

The nucleic acids described by the invention are preferably isolated. The term "isolated nucleic acid" means according to the invention that the nucleic acid (i) has been amplified in vitro, for example by polymerase chain reaction (PCR), (ii) has been produced recombinantly by cloning, (iii) has been purified, for example by cleavage and fractionation by gel electrophoresis, or (iv) has been synthesized, for example by chemical synthesis. An isolated nucleic acid is a nucleic acid which is available for manipulation by recombinant DNA techniques.

Nucleic acids which code for fusion molecules can according to the invention be alone or in combination with other nucleic acids, especially heterologous nucleic acids. In preferred embodiments, a nucleic acid is functionally connected to expression control sequences or regulatory sequences which may be homologous or heterologous in relation to the nucleic acid. A coding sequence and a regulatory sequence are "functionally" connected together if they are linked together covalently in such a way that expression or transcription of the coding sequence is under the control or under the influence of the regulatory sequence. If the coding sequence is to be translated into a functional protein and where there is a functional connection of a regulatory sequence to the coding sequence, induction of the regulatory sequence leads to transcription of the coding sequence without the occurrence of a shift in reading frame in the coding sequence or of an inability of the coding sequence to be translated into the desired protein or peptide.

The term "expression control sequence" or "regulatory sequence" includes according to the invention promoters, enhancers and other control elements which control the expression of a gene. In particular embodiments of the invention, the expression control sequences can be regulated. The exact structure of regulatory sequences may vary species-dependently or cell type-dependently, but generally includes 5'-non-transcribed and 5'-non-translated sequences which are involved in initiating transcription and translation, respectively, such as TATA box, capping sequence, CAAT sequence and the like. In particular, 5'-non-transcribed regulatory sequences include a promoter region which includes a promoter sequence for transcriptional control of the functionally connected gene. Regulatory sequences may also include enhancer sequences or activator sequences located upstream.

In a preferred embodiment, the nucleic acid is according to the invention a vector, where appropriate having a promoter which controls the expression of a nucleic acid, e.g. of a nucleic acid which codes for a fusion molecule of the invention. In a preferred embodiment, the promoter is a T7, T3 or SP6 promoter.

The term "vector" is used in this connection in its most general meaning and includes any of the intermediate vehicles for a nucleic acid which make it possible, for example, for the nucleic acid to be introduced into prokaryotic and/or into eukaryotic cells and, where appropriate, be integrated into a genome. Such vectors are preferably replicated and/or expressed in the cell. An intermediate vehicle may be adapted for example for use in electroporation, in microprojectile bombardment, in liposomal administration, in transfer with the aid of *agrobacteria* or in insertion via DNA or RNA viruses. Vectors include plasmids, phagemids, bacteriophages or viral genomes.

The nucleic acids which code for a fusion molecule of the invention can be employed for transfection of host cells. Nucleic acids mean in this connection both recombinant DNA and RNA. Recombinant RNA can be prepared by in vitro transcription from a DNA template. It can moreover be modified before application by stabilizing sequences, capping and polyadenylation.

The term "host cell" relates according to the invention to any cell which can be transformed or transfected with an exogenous nucleic acid. The term "host cells" includes according to the invention prokaryotic (e.g. *E. coli*) or eukaryotic (e.g. dendritic cells, B cells, CHO cells, COS cells, K562 cells, yeast cells and insect cells). Mammalian cells are particularly preferred, such as cells from humans, mice, hamsters, pigs, goats and primates. The cells may be derived from a large number of tissue types and include primary cells and cell lines. Specific examples include keratinocytes, peripheral blood leukocytes, bone marrow stem cells and embryonic stem cells. In further embodiments, the host cell is an antigen-presenting cell, in particular a dendritic cell, a monocyte or macrophage. A nucleic acid may be present in the host cell in a single or in multiple copies and is, in one embodiment, expressed in the host cell.

The term "expression" is used according to the invention in its most general meaning and includes the production of RNA or of RNA and protein. It also includes partial expression of nucleic acids. In addition, the expression may be transient or stable. Preferred expression systems in mammalian cells include pcDNA3.1 and pRc/CMV (Invitrogen, Carlsbad, Calif.), which comprise a selectable marker such as a gene which confers resistance to G418 (and thus makes selection of stably transfected cell lines possible), and the enhancer-promoter sequences of cytomegalovirus (CMV).

A nucleic acid coding for a fusion molecule of the invention may also include a nucleic acid sequence which codes for an MHC molecule, preferably for an HLA molecule. The nucleic acid sequence which codes for an MHC molecule may be present on the same expression vector as the nucleic acid which codes for the fusion molecule, or the two nucleic acids may be present on different expression vectors. In the latter case, the two expression vectors can be cotransfected into a cell.

A sequence derived from an amino acid sequence or the expression "sequence derived from an amino acid sequence" relates according to the invention to homologous sequences and derivatives of the former sequence.

Homologous amino acid sequences exhibit according to the invention at least 40%, in particular at least 50%, at least 60%, at least 70%, at least 80%, at least 90% and preferably at least 95%, at least 98 or at least 99% identity of the amino acid residues.

"Derivatives" of a protein or polypeptide or of an amino acid sequence in the sense of this invention include amino acid insertion variants, amino acid deletion variants and/or amino acid substitution variants.

Amino acid insertion variants include amino- and/or carboxy-terminal fusions, and insertions of single or multiple amino acids in a particular amino acid sequence. In amino acid sequence variants with an insertion, one or more amino acid residues are introduced into a predetermined site in an amino acid sequence, although random insertion with suitable screening of the resulting product is also possible. Amino acid deletion variants are characterized by deletion of one or more amino acids from the sequence. Amino acid substitution variants are distinguished by at least one residue in the sequence being deleted and another residue being inserted in its stead. The modifications are preferably present at positions in the amino acid sequence which are not conserved between homologous proteins or polypeptides. Amino acids are preferably replaced by others having similar properties, such as hydrophobicity, hydrophilicity, electronegativity, volume of the side chain and the like (conservative substitution). Conservative substitutions relate for example to replacement of one amino acid by another, with both amino acids being listed in the same group hereinafter:
1. small aliphatic, nonpolar or slightly polar residues: Ala, Ser, Thr (Pro, Gly)
2. negatively charged residues and their amides: Asn, Asp, Glu, Gln
3. positively charged residues: His, Arg, Lys
4. large aliphatic, nonpolar residues: Met, Leu, Ile, Val (Cys)
5. large aromatic residues: Phe, Tyr, Trp.

Three residues are put in parentheses because of their particular role in protein architecture. Gly is the only residue without a side chain and thus confers flexibility on the chain. Pro has an unusual geometry which greatly restricts the chain. Cys can form a disulfide bridge.

The amino acid variants described above can easily be prepared with the aid of known peptide synthesis techniques such as, for example, by solid phase synthesis (Merrifield, 1964) and similar methods or by recombinant DNA manipulation. Techniques for introducing substitution mutations at predetermined sites in DNA which has a known or partially known sequence are well known and include, for example, M13 mutagenesis. Manipulation of DNA sequences to prepare proteins having substitutions, insertions or deletions and the general recombinant methods for expression of proteins for example in a biological system (such as mammalian, insect, plant and viral systems) are described in detail for example in Sambrook et al. (1989).

"Derivatives" of proteins or polypeptides also include according to the invention single or multiple substitutions, deletions and/or additions of any molecules which are associated with the protein or polypeptide, such as carbohydrates, lipids and/or proteins or polypeptides.

In one embodiment, "derivatives" of proteins or polypeptides include those modified analogs resulting from glycosylation, acetylation, phosphorylation, amidation, palmitoylation, myristoylation, isoprenylation, lipidation, alkylation, derivatization, introduction of protective/blocking groups, proteolytic cleavage or binding to an antibody or to another cellular ligand. Derivatives of proteins or polypeptides may also be prepared by other methods such as, for example, by chemical cleavage with cyanogen bromide, trypsin, chymotrypsin, papain, V8 protease, $NaBH_2$, acetylation, formylation, oxidation, reduction or by metabolic synthesis in the presence of tunicamycin.

The term "derivative" also extends to all functional chemical equivalents of proteins or polypeptides.

The derivatives, described above, of proteins and polypeptides are encompassed according to the invention by the term "fusion molecule", even if no express reference is made thereto.

The pharmaceutical compositions described according to the invention can be employed therapeutically for the treatment of a pre-existing disease or prophylactically as vaccines for immunization.

The term "vaccine" relates according to the invention to an antigenic preparation which comprises for example a protein, a peptide, a nucleic acid or a polysaccharide, and which is administered to a recipient in order to stimulate its humoral and/or cellular immune system against one or more antigens which are present in the vaccine preparation. The terms "vaccination" or "immunization" relate to the process of administering a vaccine and of stimulating an immune response against an antigen. The term "immune response" relates to the activities of the immune system, including activation and proliferation of specific cytotoxic T cells after contact with an antigen.

Animal models can be employed for testing an immunizing effect, e.g. against cancer on use of a tumor-associated antigen as antigen. It is moreover possible for example, for human cancer cells to be introduced into a mouse to create a tumor, and for a nucleic acid of the invention, which codes for a fusion molecule of the invention comprising the tumor-associated antigen, to be administered. The effect on the cancer cells (for example reduction in tumor size) can be measured as criterion for the efficacy of an immunization by the nucleic acid.

As part of the composition for immunization, one or more fusion molecules are administered with one or more adjuvants to induce an immune response or increase an immune response. An adjuvant is a substance which is incorporated into an antigen or is administered together therewith and enhances the immune response. Adjuvants are able to enhance the immune response by providing an antigen reservoir (extracellularly or in macrophages), activating macrophages and stimulating certain lymphocytes. Adjuvants are known and include in a nonrestrictive manner monophosphoryl-lipid A (MPL, SmithKline Beecham), saponins such as QS21 (SmithKline Beecham), DQS21 (SmithKline Beecham; WO 96/33739), QS7, QS17, QS18 and QS-L1 (So et al., Mol. Cells. 7:178-186, 1997), incomplete Freund's adjuvant, complete Freund's adjuvant, vitamin E, Montanide, alum, CpG oligonucleotides (cf. Krieg et al., Nature 374:546-9, 1995) and various water-in-oil emulsions which are prepared from biodegradable oils such as squalene and/or tocopherol. The fusion molecules are preferably administered in a mixture with DQS21/MPL. The ratio of DQS21 to MPL is typically about 1:10 to 10:1, preferably about 1:5 to 5:1 and in particular about 1:1. In a vaccine formulation for administration to humans, DQS21 and MPL are typically present in a range from about 1 µg to about 100 µg.

Other substances which stimulate an immune response in the patient may also be administered. For example, cytokines can be used for a vaccination because of their regulatory properties on lymphocytes. Such cytokines include for example interleukin-12 (IL-12) which has been shown to enhance the protective effects of vaccines (cf. Science 268: 1432-1434, 1995), GM-CSF and IL-18.

The method of the invention for inducing an immune response in a mammal generally comprises the administration of an effective amount of a fusion molecule of the invention and/or of a nucleic acid coding therefor, in particular in the form of a vector. DNA or RNA which codes for a fusion molecule of the invention is preferably administered to a mammal together with a DNA sequence which codes for a T cell-costimulating factor, such as a gene coding for B7-1 or B7-2.

The expression "T cell-costimulating factor" relates herein to a molecule, in particular a peptide, which is able to provide a costimulating signal and thus enhances an immune response, in particular activates the proliferation of T cells in the presence of one or more fusion molecules of the invention. Such an activation of T-cell proliferation can be determined by generally known assays.

These factors include costimulating molecules which are provided in the form of proteins or nucleic acids. Examples of such costimulating molecules are B7-1 and B7-2 (CD80 and CD86, respectively) which are expressed on dendritic cells (DC) and interact with the CD28 molecule expressed on T cells. This interaction provides a costimulation (signal 2) for an antigen/MHC/TCR-stimulated (signal 1) T cell, thus enhancing the proliferation of the T cell and the effector function. B7 also interacts with CTLA4 (CD152) on T cells and investigations including CTLA4 ligands and B7 ligands show that the B7-CTLA4 interaction can enhance an antitumor immunity and CTL proliferation (Zheng, P. et al., Proc. Natl. Acad. Sci. USA 95(11):6284-6289 (1998)).

B7 is typically not expressed on tumor cells, so that they are not effective antigen-presenting cells (APCs) for T cells. Induction of B7 expression would make it possible for tumor cells more effectively to stimulate proliferation of cytotoxic T lymphocytes and an effector function. Costimulation by a B7/IL-6/IL-12 combination showed an induction of the IFN-gamma and Th1 cytokine profile in a T cell population, leading to a further enhancement of T-cell activity (Gajewski et al., J. Immunol. 154:5637-5648 (1995)).

Complete activation of cytotoxic T lymphocytes and a complete effector function requires cooperation of T-helper cells through the interaction between the CD40 ligand on the T-helper cells and the CD40 molecule which is expressed by dendritic cells (Ridge et al., Nature 393:474 (1998), Bennett et al., Nature 393:478 (1998), Schönberger et al., Nature 393:480 (1998)). The mechanism of this costimulating signal probably relates to increasing the B7 and associated IL-6/IL-12 production by the dendritic cells (antigen-presenting cells). The CD40-CD40L interaction thus complements the interactions of signal 1 (antigen/MHC-TCR) and signal 2 (B7-CD28).

The invention provides for administration of nucleic acids, polypeptides or proteins and/or cells. Administration of DNA and RNA is preferred.

It was possible to show in the experiments that, compared with the unmodified antigen, according to the invention a 100-fold lower dose of the vaccine is sufficient to induce equivalent or stronger immune responses. One problem on direct injection of nucleic acid vaccines is that the dose necessary to induce immune responses is very high. In the case of DNA vaccines, the reason is presumably mainly based on the fact that only a fraction of the cells take up injected DNA into the nucleus. In the case of RNA vaccines, the problem is presumably that in particular injected RNA is very rapidly degraded by RNAses.

It is to be expected on use of the vaccines modified according to the invention that greatly increased immune responses will be obtained on direct injection of nucleic acids, in particular RNA, compared with unmodified nucleic acids.

In a preferred embodiment, a viral vector for administering a nucleic acid which codes for a fusion molecule of the invention is selected from the group consisting of adenoviruses, adeno-associated viruses, poxviruses, including vacciniavirus and attenuated poxviruses, Semliki forest virus, retroviruses, Sindbis virus and Ty virus-like particles. Adenoviruses and retroviruses are particularly preferred. The retroviruses are normally replication-deficient (i.e. they are unable to produce infectious particles).

Various methods can be employed according to the invention to introduce nucleic acids into cells in vitro or in vivo. Such methods include transfection of nucleic acid-calcium phosphate precipitates, transfection of nucleic acids associated with DEAE, transfection or infection with the above viruses carrying the nucleic acids of interest, liposome-mediated transfection and the like. In particular embodiments, guiding of the nucleic acid to particular cells is preferred. In such embodiments, a carrier employed for administering a nucleic acid to a cell (e.g. a retrovirus or a liposome) may have a bound targeting molecule. For example, a molecule such as an antibody which is specific for a surface membrane protein on the target cell, or a ligand for a receptor on the target cell, can be incorporated into the nucleic acid carrier or bound thereto. If administration of a nucleic acid by liposomes is desired, it is possible to incorporate proteins which bind to a surface membrane protein which is associated with endocytosis into the liposome formulation in order to make targeting and/or uptake possible. Such proteins include capsid proteins or fragments thereof, which are specific for a particular cell type, antibodies against proteins which are internalized, proteins which target for an intracellular site, and the like.

The nucleic acids are preferably administered together with stabilizing substances such as RNA-stabilizing substances.

In one embodiment, the nucleic acids are administered by ex vivo methods, i.e. by removing cells from a patient, genetically modifying the cells, and reintroducing the modified cells into the patient. This generally includes the introduction of a functional copy of a gene into the cells of a patient in vitro and returning the genetically modified cells to the patient. The functional copy of the gene is under the functional control of regulatory elements which permit expression of the gene in the genetically modified cells. Transfection and transduction methods are known to the skilled worker. The invention also provides for administration of nucleic acids in vivo through the use of vectors such as viruses and targeted liposomes.

Administration of polypeptides and peptides can take place in a manner known per se.

The term "patient", "individual" or "living creature" means according to the invention a human, non-human primate or another animal, in particular mammal such as cow, horse, pig, sheep, goat, dog, cat, birds such as chicken or rodent such as mouse and rat. In a particularly preferred embodiment, the patient, the individual or the living creature is a human.

The therapeutic compositions of the invention can be administered in pharmaceutically acceptable preparations. Such preparations can comprise usually pharmaceutically acceptable concentrations of salts, buffering substances, preservatives, carriers, supplementary immunity-increasing substances such as adjuvants (e.g. CpG oligonucleotides) and cytokines and, where appropriate, other therapeutic agents.

The therapeutic agents of the invention can be administered in any conventional way, including by injection or by infusion. The administration can take place, for example, orally, intravenously, intraperitoneally, intramuscularly, subcutaneously, intracutaneously, transdermally, intralymphatically, preferably by injection into lymph nodes, especially inguinal lymph nodes, lymphatic vessels and/or into the spleen.

The compositions of the invention are administered in effective amounts. An "effective amount" relates to the amount which, alone or together with further doses, achieves a desired response or a desired effect. In the case of treatment of a particular disease or of a particular condition, the desired response relates to inhibition of the progress of the disease. This includes slowing down the progression of the disease and in particular stopping the progression of the disease. The desired response on treatment of a disease or of a condition may also be delaying the onset or preventing the onset of the disease or of the condition.

An effective amount of a composition of the invention depends on the condition to be treated, the severity of the disease, the individual patient's parameters, including age, physiological condition, height and weight, the duration of the treatment, the nature of a concomitant therapy (if present), the specific administration route and similar factors.

The pharmaceutical compositions of the invention are preferably sterile and comprise an effective amount of the therapeutically active substance to generate the desired response or the desired effect.

The doses of the compositions of the invention which are administered may depend on various parameters such as the mode of administration, the patient's condition, the desired administration period etc. In the case where a patient's response is inadequate with an initial dose, it is possible to employ higher doses (or effectively higher doses which are achieved by a different, more localized administration route).

In general, doses of from 1 ng to 1 mg, preferably from 10 ng to 100 μg, of the tumor-associated antigen are formulated and administered for a treatment or for generating or enhancing an immune response. If it is desired to administer nucleic acids (DNA and RNA), doses of from 1 ng to 0.1 mg are formulated and administered.

The pharmaceutical compositions of the invention are generally administered in pharmaceutically acceptable amounts and in pharmaceutically acceptable compositions. The term "pharmaceutically acceptable" relates to a non-toxic material which does not interact with the effect of the active ingredient of the pharmaceutical composition. Such preparations may usually comprise salts, buffering substances, preservatives, carriers and, where appropriate, other therapeutic agents. When used in medicine, the salts should be pharmaceutically acceptable. Non-pharmaceutically acceptable salts can, however, be used to prepare pharmaceutically acceptable salts thereof and are encompassed by the invention. Such pharmacologically and pharmaceutically acceptable salts include in a non-limiting manner those prepared from the following acids: hydrochloric, hydrobromic, sulfuric, nitric, phosphoric, maleic, acetic, salicylic, citric, formic, malonic, succinic acids and the like. Pharmaceutically acceptable salts can also be prepared as alkali metal or alkaline earth metal salts such as sodium, potassium or calcium salts.

A pharmaceutical composition of the invention may comprise a pharmaceutically acceptable carrier. The term "pharmaceutically acceptable carrier" relates according to the invention to one or more compatible solid or liquid fillers, diluents or capsule substances which are suitable for administration to a human. The term "carrier" relates to an organic or inorganic ingredient, natural or synthetic in nature, in which the active ingredient is combined in order to facilitate use. The ingredients of the pharmaceutical composition of the invention are usually such that no interaction which substantially impairs the desired pharmaceutical activity occurs.

The carriers are preferably sterile liquids such as water or oils, including those derived from petroleum, animals or plants, or being of synthetic origin, such as, for example, peanut oil, soybean oil, mineral oil, sesame oil, sunflower oil and the like. Saline solutions and aqueous dextrose and glycerol solutions can also be used as aqueous carriers.

Examples of excipients and carriers are acrylic and methacrylic derivatives, alginic acid, sorbic acid derivatives such as α-octadecyl-ω-hydroxypoly(oxy-ethylene)-5-sorbic acid, amino acids and their derivatives, especially amine compounds such as choline, lecithin and phosphatidylcholine, gum arabic, aromas, ascorbic acid, carbonates such as, for example, sodium, potassium, magnesium and calcium carbonates and bicarbonates, hydrogen phosphates and phosphates of sodium, potassium, calcium and magnesium, carmellose sodium, dimethicone, colors, flavorings, buffering substances, preservatives, thickeners, plasticizers, gelatin, glucose syrups, malt, colloidal silicon dioxide, hydromellose, benzoates, especially sodium and potassium benzoates, macrogol, skim milk powder, magnesium oxide, fatty acids and their derivatives and salts such as stearic acid and stearates, especially magnesium and calcium stearates, fatty acid esters and mono- and diglycerides of edible fatty acids, natural and synthetic waxes such as beeswax, yellow wax and montan glycol wax, chlorides, especially sodium chloride, polyvidone, polyethylene glycols, polyvinyl-pyrrolidone, povidone, oils such as castor oil, soybean oil, coconut oil, palm kernel oil, sugars and sugar derivatives, especially mono- and disaccharides such as glucose, fructose, mannose, galactose, lactose, maltose, xylose, sucrose, dextrose and cellulose and their derivatives, shellac, starch and starch derivatives, especially corn starch, tallow, talc, titanium dioxide, tartaric acid, sugar alcohols such as glycerol, mannitol, sorbitol and xylitol and their derivatives, glycol, ethanol and mixtures thereof.

The pharmaceutical compositions may preferably also comprise in addition wetting agents, emulsifiers and/or pH-buffering agents.

In a further embodiment, the pharmaceutical compositions may comprise an absorption enhancer. These absorption enhancers may if desired replace an equimolar amount of the carrier in the composition. Examples of such absorption enhancers include in a non-limiting manner eucalyptol, N,N-diethyl-m-toluamide, polyoxyalkylene alcohols (such as propylene glycol and polyethylene glycol), N-methyl-2-pyrrolidone, isopropyl myristate, dimethylformamide (DMF), dimethyl sulfoxide (DMSO), dimethylacetamide (DMA), urea, diethanolamine, triethanolamine and the like (see, for example, Percutaneous Penetration Enhancers, edited by Smith et al. (CRC Press, 1995)). The amount of absorption enhancer in the composition may depend on the desired effects to be achieved.

A protease inhibitor can be incorporated into the composition of the invention in order to prevent degradation of a peptide or protein agent and thus to increase the bioavailability. Examples of protease inhibitors include in a non-limiting manner aprotinin, leupepsin, pepstatin, α2-macroglobulin and trypsin inhibitor. These inhibitors can be used alone or in combination.

The pharmaceutical compositions of the invention can be provided with one or more coatings. The solid oral dosage forms are preferably provided with a coating resistant to gastric juice or are in the form of a hardened soft gelatin capsule resistant to gastric juice.

The pharmaceutical compositions of the invention may comprise suitable buffering substances such as acetic acid in a salt, citric acid in a salt, boric acid in a salt and phosphoric acid in a salt.

The pharmaceutical compositions may also comprise where appropriate suitable preservatives such as benzalkonium chloride, chlorobutanol, parabens and thimerosal.

The pharmaceutical compositions are usually presented in a unit dose form and can be produced in a manner known per se. Pharmaceutical compositions of the invention may be for example in the form of capsules, tablets, lozenges, solutions, suspensions, syrups, elixirs or as emulsion.

Compositions suitable for parenteral administration usually comprise a sterile aqueous or nonaqueous preparation of the active agent, which is preferably isotonic with the recipient's blood. Examples of suitable carriers and solvents are Ringer's solution and isotonic sodium chloride solution. In addition, sterile, fixed oils are usually employed as dissolving or suspending medium.

The present invention is described in detail by the following examples and figures which serve exclusively for illustration and are not to be understood as limiting. Further embodiments which do not go beyond the bounds of the invention and the scope of the annexed claims are accessible to the skilled worker on the basis of the description and the examples.

BRIEF DESCRIPTION OF THE DRAWINGS

FIG. 2: Diagrammatic representation of the cassettes for expression of fusion proteins. SP: signal peptide; MCS: multiple cloning site; TM: transmembrane domain; MHC tail: cytoplasmic tail of an MHC molecule; antigen: sequence coding for an antigen against which immune responses are to be induced.

FIG. 7: Diagrammatic representation of the cassettes for expressing fusion proteins. CS: cloning site; TM: transmembrane domain; SNARE: SNARE protein or motif; antigen: sequence coding for an antigen against which immune responses are to be induced.

FIGS. 8A-8E: Sequences used in the examples HLA class I TM-CM: transmembrane-cytoplasmic region of an HLA class I molecule; HLA class II TM-CM: transmembrane-cytoplasmic region of an HLA class II molecule.

FIG. 9: Sequences of transmembrane-cytoplasmic regions and cytoplasmic regions of MHC molecules. The sequences show the transmembrane-cytoplasmic region or only the cytoplasmic region of various HLA molecules. The transmembrane region is underlined and bold.

FIG. 10A-10C: Sequences of SNARE proteins. These sequences are suitable for constructing the SNARE-antigen fusion molecules (N-SNARE-antigen) of the invention.

EXAMPLES

Example 1

Preparation of the Modified Vaccines

Figure 1:
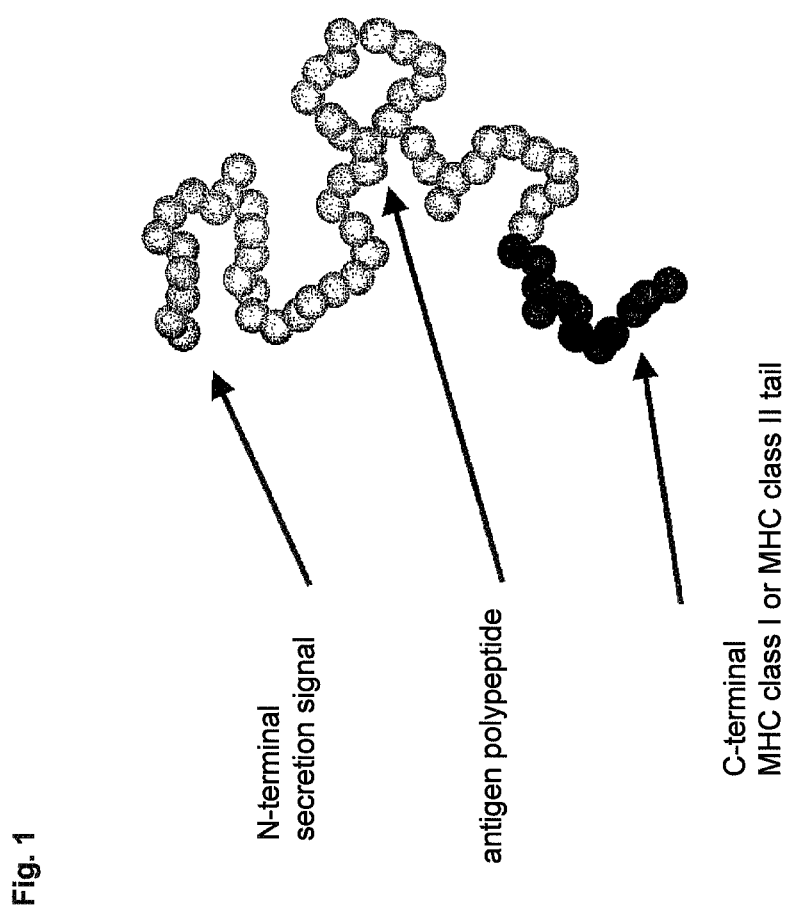
FIG. 1: Diagrammatic representation of a fusion protein of the invention. The fusion protein consists of an N-terminally placed secretion signal, of a C-terminally located transmembrane and cytoplasmic domain of a histocompatibility antigen, and of an integrated complete or partial sequence of an antigen.

To prepare the modified vaccines, firstly a cassette which permits expression of fusion genes was prepared in an expression vector which permits transcription of RNA. For this purpose, initially the nucleic acid which codes for a signal peptide of an HLA molecule was amplified from human lymphocytes, and the fragment was cloned as cDNA into a vector (SEQ ID NO: 1 and 2). The cloning was carried out in such a way that various restriction enzyme cleavage sites were located behind the cDNA of the signal peptide, and further fragments can be cloned in-frame in the expression cassette. The selected vectors were plasmids which permit in vitro expression of RNA via a 5'-located RNA polymerase promoter T3, T7 or SP6. The next fragment cloned into this vector was a cDNA which encodes a transmembrane domain and the cytoplasmic domain of an HLA class I (SEQ ID NO: 3 and 4) or class II (SEQ ID NO: 5 and 6) molecule, including stop codon. The cloning was carried out in such a way that the resulting plasmid still has restriction enzyme cleavage sites for cloning antigens between the two fragments (SEQ ID NO: 7 and 8 and FIG. 1). The sequence (SEQ ID NO: 9 and 10) coding for the human cytomegalovirus phosphoprotein 65 (pp 65) was cloned into these expression cassettes as model antigen in such a way that a continuous ORF composed of HLA signal sequence, pp 65 and HLA transmembrane and cytoplasmic domain (SEQ ID NO: 11 and 12) resulted. A vector which comprised the pp 65 sequence with a stop codon in the same initial vector without said fragments was prepared for control experiments. The following nucleic acids were used for further experiments:

CMVpp65standard: unmodified CMVpp65 sequence, standard immunogen

CMVpp65-TM1: fusion nucleic acid composed of the following fragments: HLA class I secretion signal, pp 65 ORF and HLA class I transmembrane and cytoplasmic domain (modified immunogen).

CMVpp65-TM2: fusion nucleic acid composed of the following fragments: HLA class I secretion signal, pp 65 ORF and HLA class II transmembrane and cytoplasmic domain (modified immunogen).

Example 2

Testing of the Modified Vaccines

Figure 3:
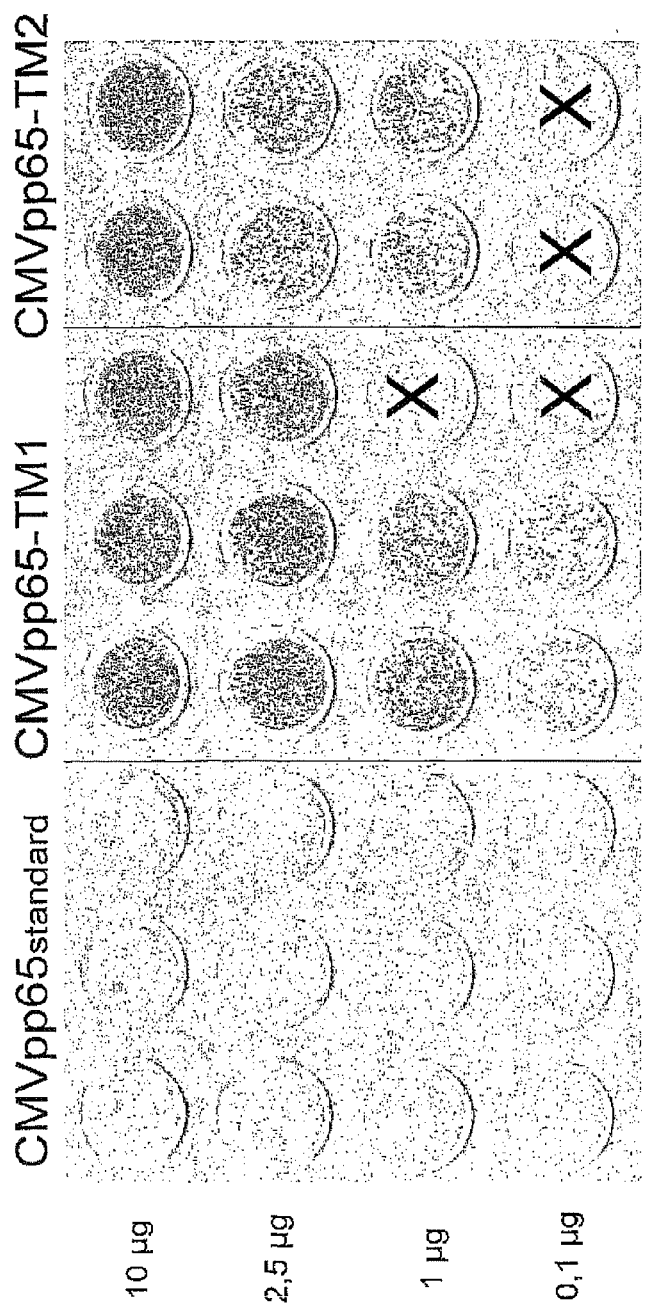
FIG. 3: Testing of the effect of various RNA doses on the frequency of antigen-specific CD4+ T lymphocytes. $1 \times 10^6$ purified CD4+ lymphocytes were cocultivated for 1 week with $2 \times 10^5$ DC which had been transfected with RNA in the stated amounts (0.1-10 μg RNA) by electro-poration. On day 7 after stimulation, an ELISPOT was carried out under standard conditions to detect interferon-γ-secreting T lymphocytes. The antigen-presenting cells used were DC from the same donor which had been loaded with overlapping pp 65 peptides (1.75 μg/ml) or an irrelevant control peptide. For the test, $3 \times 10^4$ effectors were coincubated with $2 \times 10^4$ DC for 16 h. After standard development, the number of IFN-gamma-secreting T lymphocytes was determined by means of a software-based video analysis. Compared with the CMVpp65standard RNA, there is seen to be a massive expansion of CD4+ lymphocytes both by the CMVpp65-TM1 construct and by the CMVpp65-TM2 construct.

The three nucleic acids (CMVpp65standard, CMVpp65TM1, CMVpp65TM2) were employed as immunogen in stimulation tests with autologous DCs from antigen-positive donors. In order to test CD4 and CD8 immune responses separately, purified CD4+ and CD8+ lymphocytes were used. The readout employed was the enzyme-linked immunospot assay (ELISPOT), which is acknowledged to be the standard assay for quantifying IFN-2-secreting T cells. A standard chromium release assay was used to assay the effector function of CD8+ T lymphocytes. Autologous monocytes or DCs were transfected with pp 65 RNA, CMVpp65-TM1 and CMVpp65-TM2 immunogens. DCs were loaded with overlapping peptides for pp 65 and with control peptide as maximum stimulation control. The DCs treated in this way were coincubated with CD4+ or CD8+ lymphocytes overnight or for 7 days. The readout took place against autologous monocytes or DCs which had been pulsed with pp 65 overlapping peptides or with a CMV fibroblast lysate. The investigation of CD4+ immune responses surprisingly revealed that both modified immunogens (CMVpp65-TM1 and CMVpp65-TM2) not only induced an enhanced immune response to the CMVpp65standard immunogen, but also induced a maximum level of antigen-specified IFN-gamma secretion in CD4+ lymphocytes (FIG. 3). The percentage of antigen-specific CD4+ cells after stimulation by the modified pp 65 constructs was moreover equal to or even higher than after stimulation with pp 65 overlapping peptides. As expected, the CMVpp65standard immunogen showed no relevant stimulation of CD4+ lymphocytes.

Figure 4:
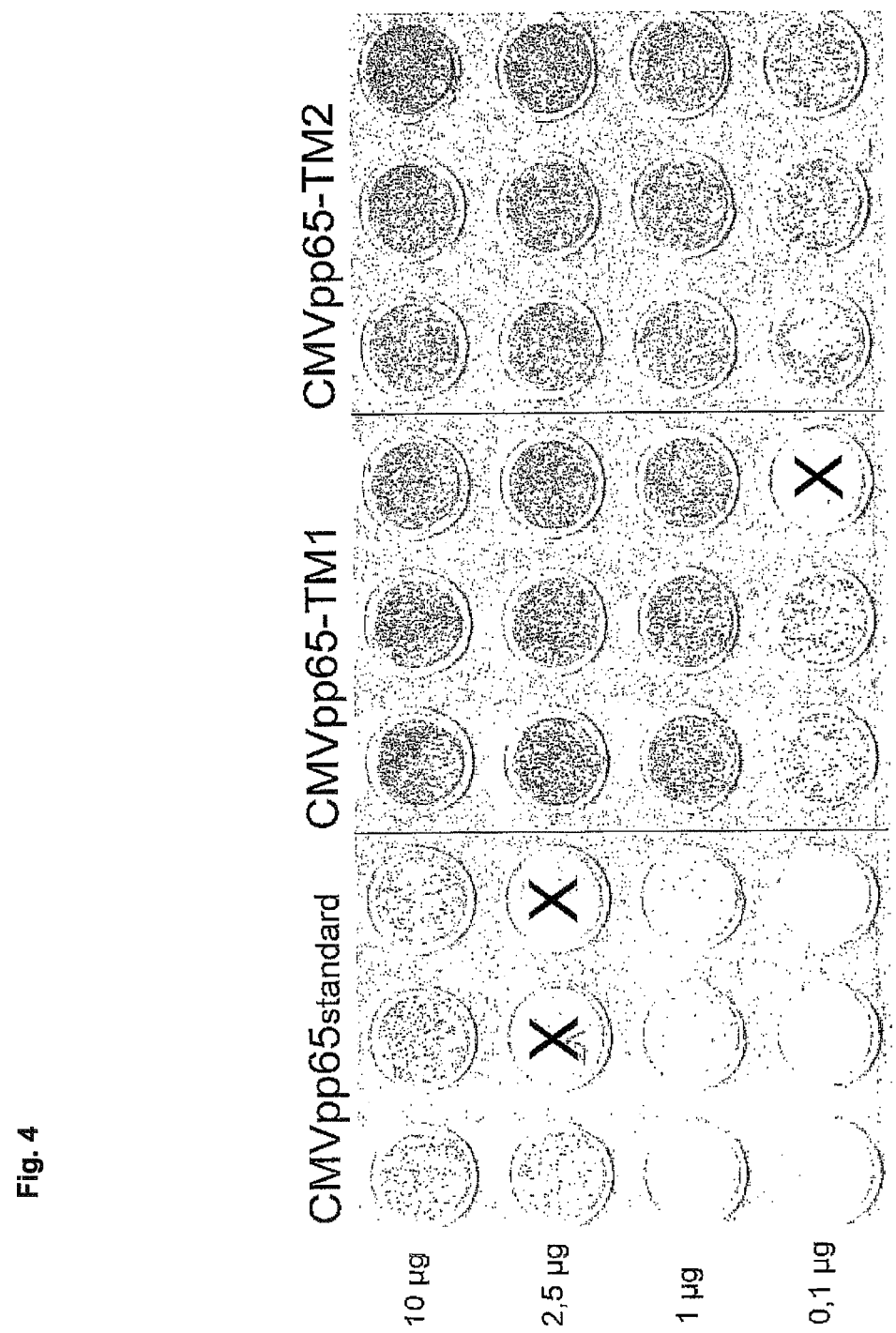
FIG. 4: Testing of the effect of various RNA doses on the frequency of interferon-gamma-secreting CD8+ T lymphocytes. $1 \times 10^6$ purified CD8+ lymphocytes were cocultivated for 1 week with $2 \times 10^5$ DC which had been transfected with RNA in the stated amounts (0.1-10 μg RNA) by electroporation. On day 7, a standard ELISPOT was carried out to detect IFN-gamma-secreting T lymphocytes against DC of the same donor which had been loaded with overlapping pp 65 peptides (1.75 μg/ml) or an irrelevant control peptide. $3 \times 10^4$ effectors were coincubated with $2 \times 10^4$ DC for 16 h. After standard development, the number of IFN-gamma-secreting T lymphocytes was determined by means of a software-based video analysis. There was seen to be a massive expansion of CD8+ lymphocytes by the CMVpp65-TM1 construct and the CMVpp65-TM2 construct. Even on use of 100× lower doses (0.1 μg RNA), the frequency of the pp 65-specific CD8+ lymphocytes was still above the background after stimulation by DC transfected with NYESO-RNA (data not shown). Stimulation by the CMVpp65standard construct showed an expansion of pp 65-specific lymphocytes above the background level only with 2.5 μg and above.
Figure 5:
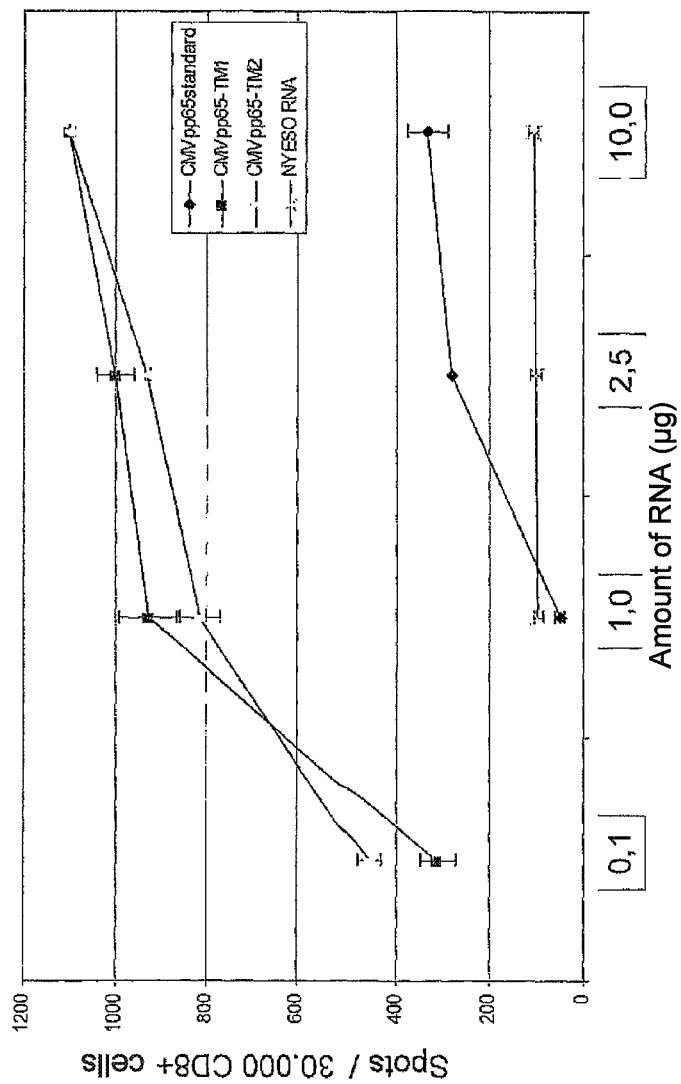
FIG. 5: Dose/effect profile for the expansion capacity of various immunogens on antigen-specific lymphocytes. The immunogens modified according to the invention exhibit a distinctly increased potency (>100×) and a higher maximum effect.
Figure 6:
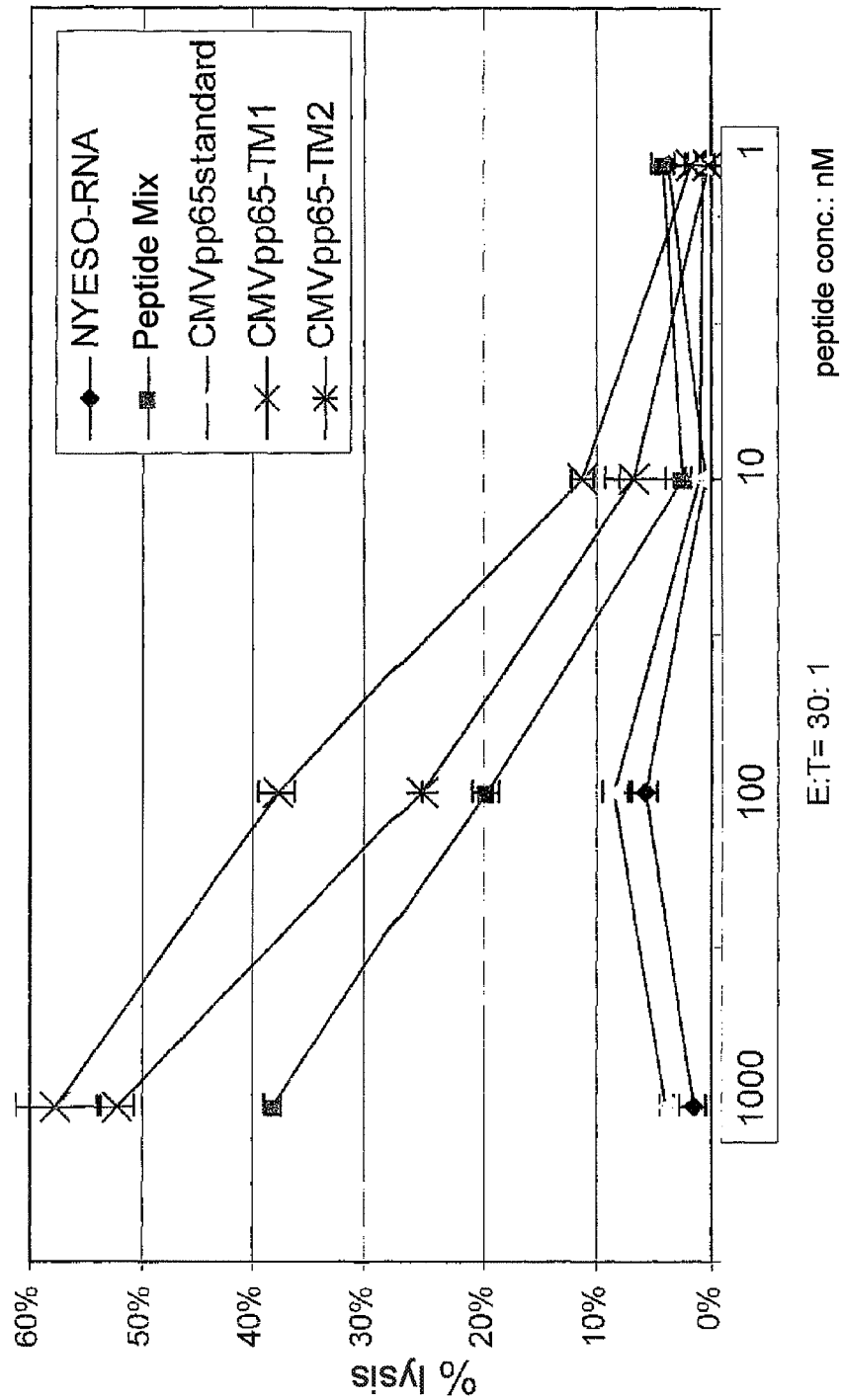
FIG. 6: Comparative test of the effect of immunogens modified according to the invention and standard immunogens on the generation of cytotoxic immune responses. $1 \times 10^6$ purified CD8+ lymphocytes were cocultivated for 1 week with $2 \times 10^5$ DC which had been transfected with 10 μg of RNA by electroporation. On day 7, a standard cytochrome cytotoxicity assay against DC of the same donor which had been loaded with various concentrations of overlapping pp 65 peptides or an irrelevant control peptide was carried out. $15 \times 10^4$ effectors were coincubated with $0.5 \times 10^4$ DC for 4 h. After measurement of the supernatant in a counter, the specific lysis was calculated according to the formula: There was seen to be extensive lysis by CD8+ lymphocytes which had been stimulated with CMVpp65-TM1 and CMVpp65-TM2 constructs, which was above the value for the control peptide as far as a concentration of 10 nM of the pp 65 peptide mixture (data not shown). CD8+ lymphocytes were likewise expanded by the pp 65 peptide mixture and showed a marked specific lysis, but did not reach the level of CMVpp65-TM1 and -TM2. Only a weak stimulation of pp 65-specific cytotoxic T cells was achievable by the CMVpp65standard construct.

An even more surprising result emerged on investigation of CD8 immune responses after stimulation with the immunogens. It was possible to show that the use of the modified expression cassettes for stimulating CD8+ lymphocytes likewise led to a proportion of specifically IFN-λ-secreting cells which is comparable to that after stimulation with pp 65 overlapping peptides. Surprisingly, the modified RNA constructs were far superior to the unmodified CMVpp65standard immunogens in this case too (FIGS. 4 and 5). The results in the cytotoxicity assay showed that both modifications led to a not previously described drastic increase in cytotoxicity compared with CMVpp65standard RNA (FIG. 6). In this case too there was surprisingly seen to be a superiority of the modified immunogens over the overlapping pp 65 peptides.

Example 3

Stimulation of Naive CD8+ T Lymphocytes by HLA Fusion Antigens

Figure 11:
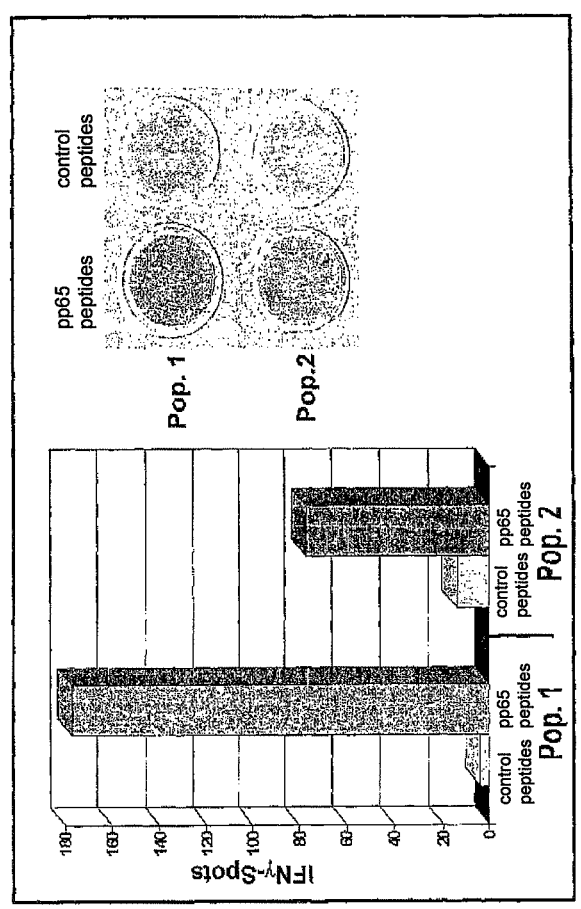
FIG. 11: Stimulation of naive CD8+ T lymphocytes by fusion constructs of the invention. In microtiter plates, $1 \times 10^5$ CD8+ lymphocytes per well were stimulated against $2 \times 10^4$ DC which were transfected with 20 μg of CMVpp65-TM1 or control RNA. The medium was supplemented with IL-6 (1000 U/ml) and IL-12 (10 ng/ml). On day +7 and +14, thawed transfected DC ($2 \times 10^4$/well) were used for restimulation, the medium containing IL-2 (10 U/ml) and IL-7 (5 ng/ml). On day +21, all the populations were assayed in an ELISPOT against control peptides (1.75 μg/ml) and against pp 65-overlapping peptides (1.75 μg/ml). Two of the populations stimulated against CMVpp65-TM1 (Pop.1, Pop.2) showed a marked pp 65 reactivity.

In order to attest the possibility of priming and subsequent expansion of naive CD8+ lymphocytes by the fusion constructs of the invention, dendritic cells of a CMV-negative donor were transfected with RNA of the unmodified CMVpp65 or with CMVpp65-TM1 RNA or with a control RNA (NY-Eso-1). The transfected dendritic cells were employed to stimulate autologous CD8+ lymphocytes. 2 restimulations were carried out with frozen transfected dendritic cells at weekly intervals. For the readout, on day +21 after the first stimulation, all cell populations were assayed in an IFNγ, ELISpot assay against autologous dendritic cells which were loaded either with pp 65 overlapping peptides or, as control, with irrelevant overlapping peptides. It was found in this case that pp 65-reactive CD8+ T lymphocyte populations were generated by stimulation with CMVpp65-TM1 RNA in two cases (FIG. 11). Stimulations with the dendritic cells transfected with the unmodified CMVpp65 RNA or with control RNA by contrast showed no significant pp 65 reactivity.

Example 4

Use of HLA Fusion Antigens for Stimulating Tumor Cell-Reactive T Lymphocytes

In order to be able to expand CD8+ and CD4+ T lymphocytes against defined tumor antigens, the following antigen sequences were cloned as inserts into fusion constructs of the invention: the tumor antigen TPTE (Koslowski et al., 2004, PMID 15342378), the tumor antigen PRAME (Ikeda et al., 1997, PMID 9047241) in variant 1 (SEQ ID NO: 64), the tumor antigen WT1 as variant C (SEQ ID NO: 65) and the tumor antigen p53 (SEQ ID NO: 66). For the functional validation, human dendritic cells of an HLA*A 0201-positive donor were transfected either with WT1-HLA-TM1-RNA, with unmodified WT1-RNA or irrelevant control RNA and used as target cells. After coincubation with WT1-reactive CD8+ T-cell clones for 8 or 16 hours, IFNγ was quantified in the supernatant. It was seen that secretion was a factor of 6-9 higher after coincubation with WT1-HLA-TM1 transfected dendritic cells by comparison with coincubation after transfection with unmodified WT1.

In a series of experiments, the following results were achieved in summary and confirmed several times:

The modified immunogens lead to a distinctly enhanced stimulation and expansion of antigen-specific CD4+ lymphocytes (increased proliferation of CD4+ lymphocytes)

The modified immunogens lead to a distinctly enhanced stimulation and expansion of antigen-specific CD8+ lymphocytes (increased proliferation of CD8+ lymphocytes)

The modified immunogens lead to a distinctly enhanced cytokine release from antigen-specific CD4+ lymphocytes and CD8+ lymphocytes (increased cytokine release=increased activation)

The modified immunogens lead to a distinctly enhanced cytotoxic reactivity of antigen-specific CD8+ lymphocytes (increased cytotoxic effect)

The modified immunogens are 100× more potent in relation to the expansion of antigen-specific CD8+ lymphocytes The modified immunogens have, even at a 100× lower dose, a stronger effect on the expansion of antigen-specific CD4+ lymphocytes than standard immunogens In summary, therefore, it can be said that the modifications according to the invention of an antigen result in a more than 100-fold increased potency (leftward shift in the dose-effect curve) and a drastically increased biological activity. Compared with the unmodified antigen sequences customary to date, it is possible to generate an immunogen which has a quantitatively and qualitatively greater efficacy as vaccine.

An important result of the invention is that antigen-specific CD4+ and CD8+ lymphocytes are optimally stimulated and expanded simultaneously. Stimulation of CD8+ and CD4+ lymphocytes is crucially important for the efficacy in particular of therapeutic vaccines.

The invention claimed is:

1. A nucleic acid molecule which codes for a fusion protein comprising an antigen, and a transmembrane region and a cytoplasmic region of a chain of a MHC molecule or CD1a, CD1b or CD1c but free from (i) α1, α2 and α3 domains of the α chain of a MHC Class I molecule or CD1a, CD1b or CD1c, (ii) β2-microglobulin of a MHC Class I molecule or CD1a, CD1b or CD1c, (iii) α1 and α2 domains of the α chain of a MHC Class II molecule, and (iv) β1 and β2 domains of the β chain of a MHC Class II molecule.

2. An isolated host cell which comprises the nucleic acid molecule as claimed in claim 1.

3. A composition which comprises the nucleic acid molecule of claim 1 in a pharmaceutically acceptable carrier.

4. The nucleic acid molecule of claim 1 wherein the nucleic acid molecule encodes a fusion protein that includes an amino acid residue sequence selected from the group consisting of SEQ ID NO: 2, 4, 12, 14, 15, 16, 17, 18, 19, 20, 21, 22, 23, 24, 25, 26, 27, 28, 29, 30, 31, 32, 33, 34, 35, 36, 37, 38, 39, 40, 41, and 42.

5. The nucleic acid molecule of claim 1 wherein the nucleic acid molecule comprises the nucleotide sequence of SEQ ID NO: 11 or SEQ ID NO: 13.

6. The nucleic acid molecule of claim 1 wherein the nucleic acid molecule encodes the amino acid residue sequence of SEQ ID NO: 12.

7. The nucleic acid molecule of claim 1 wherein the nucleic acid molecule comprises the nucleotide sequence of SEQ ID NO: 11.

8. The nucleic acid molecule of claim 1 wherein the nucleic acid molecule comprises the nucleotide sequence of SEQ ID NO: 13.

9. The nucleic acid molecule of claim 1 wherein the nucleic acid molecule encodes the amino acid residue sequence of SEQ ID NO: 14.

10. A composition which comprises isolated the host cell of claim 2.

* * * * *